United States Patent
Li et al.

(10) Patent No.: US 12,318,381 B2
(45) Date of Patent: Jun. 3, 2025

(54) TREATMENT FOR NON-ALCOHOLIC FATTY LIVER DISEASE

(71) Applicants: 1GLOBE BIOMEDICAL CO., LTD., Beijing (CN); 1GLOBE HEALTH INSTITUTE LLC, Norwood, MA (US)

(72) Inventors: Chiang J. Li, Cambridge, MA (US); Zoltan Derdak, Attleboro, MA (US); Jifeng Liu, Winchester, MA (US)

(73) Assignees: 1GLOBE BIOMEDICAL CO., LTD., Beijing (CN); 1GLOBE HEALTH INSTITUTE LLC, Norwood, MA (US)

( * ) Notice: Subject to any disclaimer, the term of this patent is extended or adjusted under 35 U.S.C. 154(b) by 1009 days.

(21) Appl. No.: 17/276,482

(22) PCT Filed: Sep. 18, 2019

(86) PCT No.: PCT/US2019/051790
§ 371 (c)(1),
(2) Date: Mar. 15, 2021

(87) PCT Pub. No.: WO2020/061232
PCT Pub. Date: Mar. 26, 2020

(65) Prior Publication Data
US 2022/0040172 A1 Feb. 10, 2022

Related U.S. Application Data

(60) Provisional application No. 62/732,644, filed on Sep. 18, 2018.

(51) Int. Cl.
| | | |
|---|---|---|
| A61K 31/496 | (2006.01) | |
| A61K 31/355 | (2006.01) | |
| A61K 31/427 | (2006.01) | |
| A61K 31/4439 | (2006.01) | |
| A61K 31/593 | (2006.01) | |
| A61K 45/06 | (2006.01) | |
| A61P 1/16 | (2006.01) | |

(52) U.S. Cl.
CPC .......... *A61K 31/496* (2013.01); *A61K 31/355* (2013.01); *A61K 31/427* (2013.01); *A61K 31/4439* (2013.01); *A61K 31/593* (2013.01); *A61K 45/06* (2013.01); *A61P 1/16* (2018.01)

(58) Field of Classification Search
CPC ........ A61K 31/496; A61K 31/355; A61P 1/16
See application file for complete search history.

(56) References Cited

U.S. PATENT DOCUMENTS

| | | |
|---|---|---|
| 2013/0267493 A1 | 10/2013 | Bhattacharya et al. |
| 2016/0031888 A1 | 2/2016 | Li et al. |
| 2017/0105996 A1 | 4/2017 | Ilan et al. |
| 2017/0172954 A1 | 6/2017 | Bisgaier et al. |
| 2018/0022743 A1 | 1/2018 | Li et al. |
| 2018/0230141 A1 | 8/2018 | Nonoyama et al. |

FOREIGN PATENT DOCUMENTS

| | | |
|---|---|---|
| WO | WO2008100977 A2 | 8/2008 |
| WO | WO2014202528 A1 | 12/2014 |
| WO | WO2015091937 A1 | 6/2015 |
| WO | WO2015112941 | 7/2015 |
| WO | WO2018005444 A2 | 1/2018 |
| WO | WO2020061231 A1 | 3/2020 |

OTHER PUBLICATIONS

Rospatent, office action in equivalent Russian Patent Application No. 2021107147/04, mailed Mar. 13, 2023.
Rospatent, English translation of C11.
Taiwan IP Bureau, first Examiner report in equivalent Taiwan Patent application No. 108133698, mailed Jun. 2, 2023.
IP India, first Office action in equivalent Indian Patent Application No. 202117017104, office action mailed Sep. 4, 2023.
IP Office of Singapore, first Office action in equivalent Singaporian applictaion No. 11202102684V, Sep. 5, 2022.
Canadian IP Office, first Written Opinion in equivalent Canadian applictaion No. 3113016, mailed Mar. 26, 2024.
ISA(US), International Search Report and Written Opinion for PCT/CN2019/051790, Mar. 2, 2020, USA.
Pacifico et al. "The Impact of Nonalcoholic Fatty Liver Disease on Renal Function in Children with Overweight/besity", Intl J of Mol Sci, Jul. 27, 2016.
Liang, D. et al. "Inhibition of EGFR attenuates fibrosis and stellate cell activation . . . " BBA—Mol Basis of Dis., 1864 (2018) 133-142, Oct. 2017.
Mitomo, S et al. "Sunitinib treatment enabling resection of massive liver metastasis: a case report" J. Med. Case Reports, 7(1), pp. 1-5(234) 2013.
Chinese Patent Office, Search Report in equivalent Chinese applictaion No. 201980061364.1, mailed Apr. 19, 2022.
Chinese Patent Office, first Office action in equivalent Chinese applictaion No. 201980061364.1, mailed Apr. 19, 2022.
EPO, extended European search report in equivalent European Patent Application No. 19861804.3, mailed May 11, 2022.
Japanese Patent Office, first Office action in equivalent Japanese Application No. 2021-539501, including cited reference, Sep. 26, 2023.

(Continued)

*Primary Examiner* — Kamal A Saeed
(74) *Attorney, Agent, or Firm* — Milstein Zhang & Wu LLC; Duan Wu, Esq.

(57) ABSTRACT

The invention provides novel methods of treating or preventing nonalcoholic fatty liver disease (NAFLD) including non-alcoholic steatohepatitis (NASH) in a mammal including a human.

18 Claims, 14 Drawing Sheets

(56) References Cited

OTHER PUBLICATIONS

IP Australia, first Office action in equivalent Australian Application No. 2019345297, mailed Nov. 22, 2023.
New Zealand IP Office, first Office action in equivalent NZ Application No. 774401, mailed Feb. 12, 2024.
Cameron, K. O. et al., Discovery and Preclinical Characterization of 6-Chloro-5-[4-(1-hydroxycyclobutyl)phenyl]-1H-indole-3-carboxylic Acid . . . , J. Med. Chem. 2016, 39, 8068-8081.
Friedman, S. L. et al., "Mechanisms of NAFLD development and therapeutic strategies" Nat Med, 2018, 24(7):908-922.

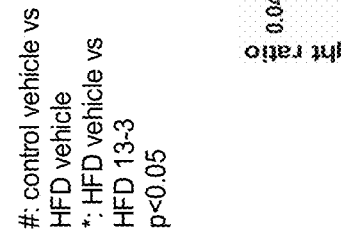
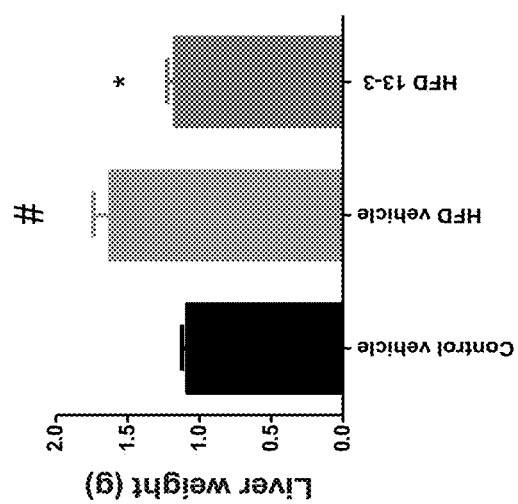
FIG. 3B
FIG. 3C

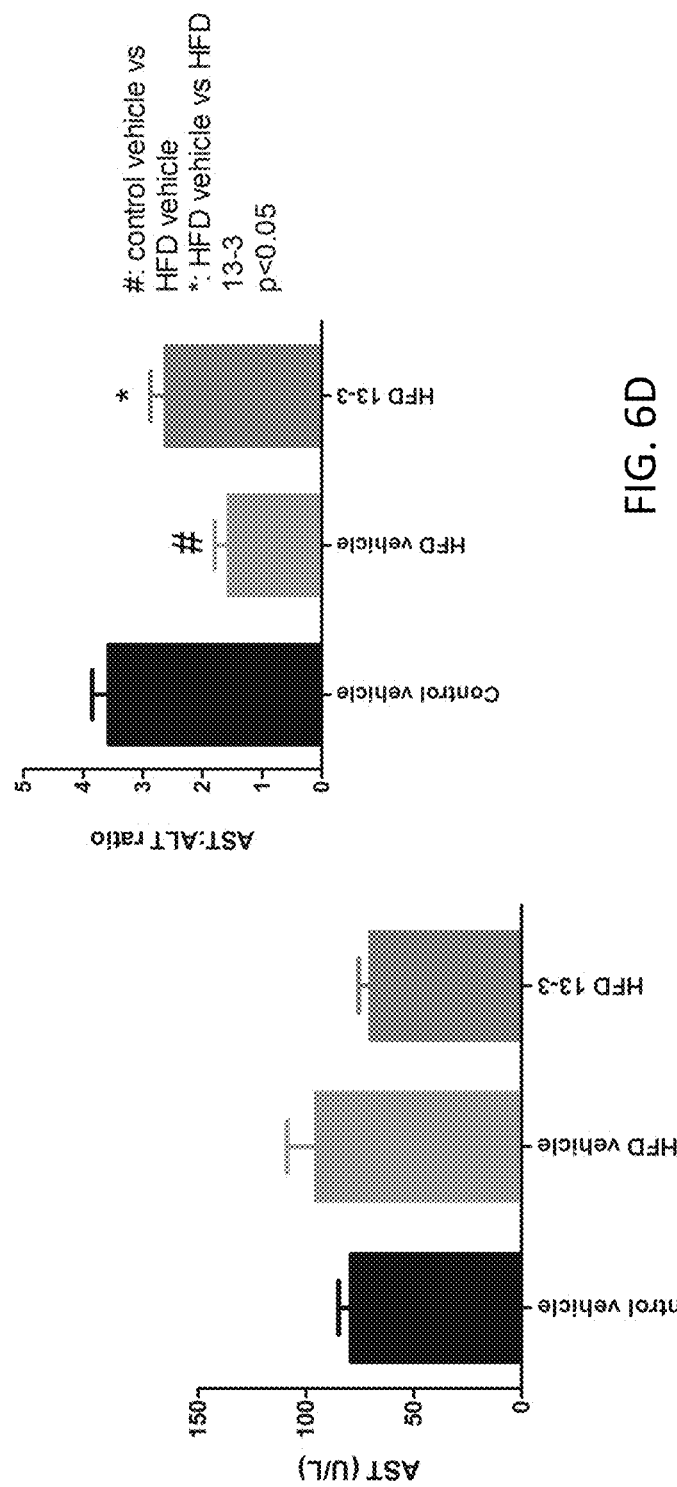

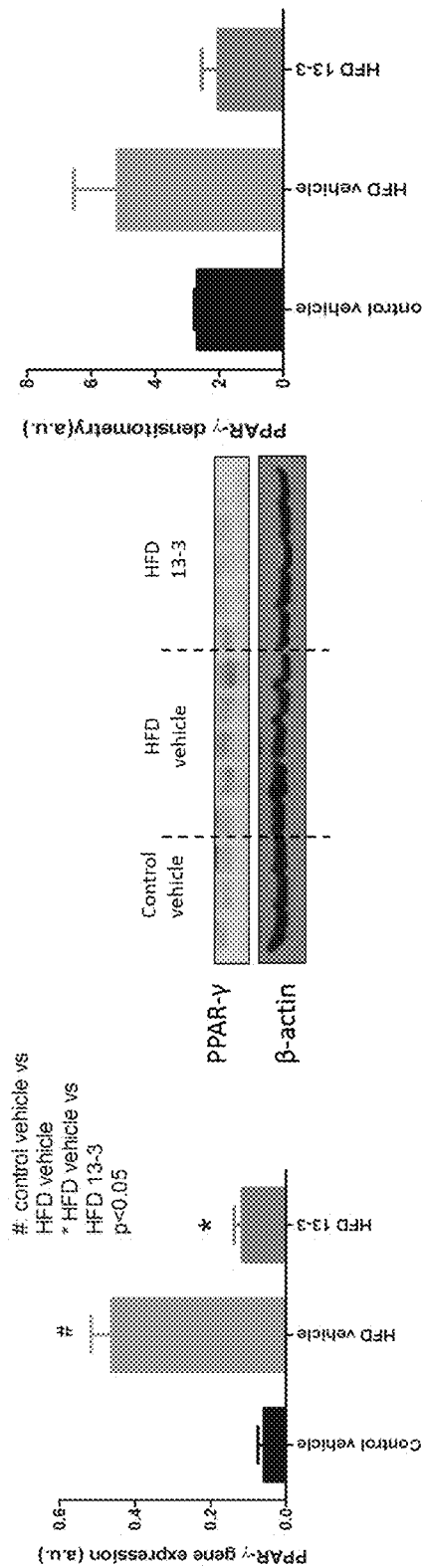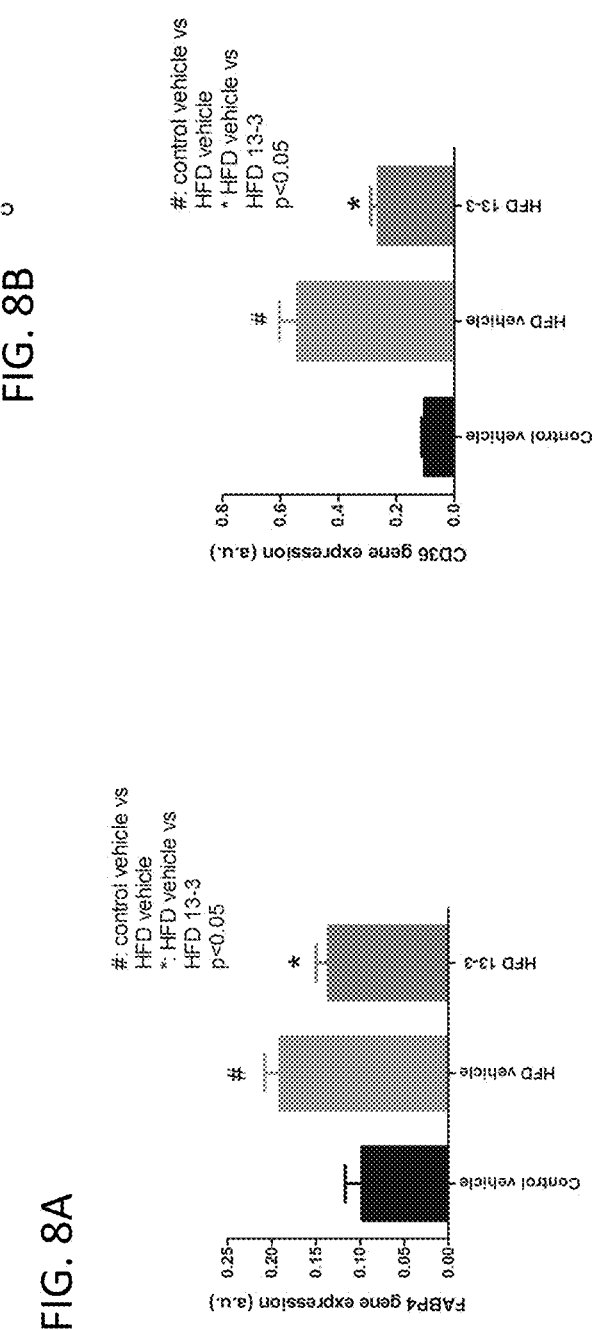
FIG. 8A
FIG. 8B
FIG. 8C
FIG. 8D

TREATMENT FOR NON-ALCOHOLIC FATTY LIVER DISEASE

CROSS-REFERENCE TO RELATED APPLICATIONS

This application is a national phase application under 35 U.S.C. 371 of international application PCT/US19/51790, filed Sep. 18, 2019 which claims priority to and the benefit of co-pending U.S. provisional patent application Ser. No. 62/732,644, filed Sep. 18, 2018, which application is incorporated herein by reference in its entirety.

TECHNICAL FIELD

The invention generally relates to methods of treating non-alcoholic fatty liver disease (NAFLD) especially non-alcoholic steatohepatitis (NASH) in a subject and related compositions thereof.

BACKGROUND OF INVENTION

Non-alcoholic fatty liver disease (NAFLD), the hepatic manifestation of the metabolic syndrome, is the most common chronic liver disease in the U.S., affecting 75-100 million Americans (Rinella M E. JAMA 2015; 313(22): 2263-2273). With increased caloric intake through richer diets and more sedentary lifestyles, more people in growing parts of the world are now facing NAFLD as a serious threat to their health. While it is closely linked to obesity, type II diabetes mellitus and metabolic syndrome, the public health impact of NAFLD is significant due to associated morbidity and mortality.

NAFLD as an emerging global epidemic has become the most common cause of abnormal liver function tests in the clinical practice. NAFLD is present when >5% of liver cells harbor excessive amount of fat in the livers of people who drink little or no alcohol (<20 g/day for women and <30 g/day for men). NAFLD has been traditionally viewed as a spectrum of diseases that starts with clinically benign steatosis (non-alcoholic fatty liver or NAFL) that may progress into more serious conditions such as non-alcoholic steatohepatitis (NASH). Patients with NASH are at great risk to develop fibrosis, cirrhosis and other complications including hepatocellular carcinoma (HCC) (Sanyal A J. Nat Clin Pract Gastroenterol Hepatol 2005; 2(1):46-53). It has been believed that cirrhosis develops in 15-25% of patients with NASH (Matteoni C A et al. Gastroenterology 1999; 116(6): 1413-1419. Bacon B R et al. Gastroenterology 1994; 107 (4):1103-1109. Powell E E et al. Hepatology 1990; 11(1): 74-80. Lee R G. Hum Pathol 1989; 20(6):594-598.) and 30-40% of those patients with cirrhosis succumb to liver-related death (Rinella M E. JAMA 2015; 313(22):2263-2273). NASH is, therefore, now considered the progressive subtype of NAFLD since hepatic steatosis with accompanying inflammation and hepatocellular injury has a more progressive natural history than isolated steatosis.

Currently, there are no medications approved by the Federal Drug Administration (FDA) or European Medicines Agency (EMA) for the treatment of NAFLD or NASH, although there are many pharmacologic agents (e.g., obeticholic acid, elafibranor, cenicriviroc, selonsertib) involved in ongoing clinical trials. The cornerstone of all therapeutic efforts remains lifestyle intervention with weight loss. There are multiple studies demonstrating that the degree of liver histological improvement is directly proportional to the amount of weight loss (Harrison S A et al. Hepatology 2009; 49(1):80-86. Wong V W et al. J Hepatol 2013; 59(3):536-542). Current pharmacological agents that have demonstrated efficacy in randomized clinical trials include vitamin E, pioglitazone, and pentoxifylline. Vitamin E is the most commonly used medication in clinical practice; current AASLD and EASL guidelines recommend its use in non-diabetic, non-cirrhotic patients with NASH, based on data generated in the PIVENS trial (Chalasani N et al. Hepatology 2017; 67(1):328-357. European Association for the Study of the L et al. J Hepatol 2016; 64(6):1388-1402. Sanyal A J et al. N Engl J Med 2010; 362(18):1675-1685). Nonetheless, safety concerns have been raised related to the use of vitamin E, since it has been linked to increased risk of mortality, prostate cancer and hemorrhagic stroke (Bjelakovic G et al. JAMA 2007; 297(8):842-857. Klein E A et al. JAMA 2011; 306(14):1549-1556. Miller E R et al. Ann Intern Med 2005; 142(1):37-46). The insulin sensitizer pioglitazone has also been prescribed in patients with NASH with or without diabetes with fairly consistent improvements in various features of NASH. Nevertheless, a major downside of the use of this agent is the 3-5 kg weight gain that occurs in 60-70% of patients (Sanyal A J et al. N Engl J Med 2010; 362(18):1675-1685. Musso G et al. Hepatology 2010; 52(1):79-104). Pioglitazone also should not be used in patients with clinically evident heart failure (Nesto R W et al. Diabetes Care 2004; 27(1):256-263). In addition, this agent has been associated with postmenopausal bone loss (Lecka-Czernik B. Curr Osteoporos Rep 2010; 8(4):178-184). Pentoxifylline has been studied in two randomized clinical trials (Van Wagner L B et al. Ann Hepatol 2011; 10(3):277-286. Zein C O et al. Hepatology 2011; 54(5): 1610-1619) that suggest histological benefit in NASH (including the decrease of hepatic fibrosis); however, these trials were small and their conclusion requires further confirmation in larger trials. While there is a lack of complete understanding of the causes for NASH, insulin resistance and accumulation of toxic lipid metabolites are believed to play a key role in its development (Filozof et al. Drugs 2015; 75:1373-1392).

Clearly, there are continued unmet needs for effective treatment and/or prophylaxis for NASH and other NAFLD-associated conditions.

SUMMARY OF THE INVENTION

The present invention addresses these needs. The invention provides for novel method of using a compound of the invention (embodiments described in detail below). In one aspect, the invention provides methods for treating or preventing nonalcoholic fatty liver disease (NAFLD) in a mammal including a human, comprising administering to a mammalian subject in need thereof: a therapeutically effective amount of a pharmaceutical composition comprising the compound of the invention, or an enantiomer, diastereomer, tautomer, or pharmaceutically acceptable salt, solvate, ester or pro-drug thereof that is effective in the treatment or prevention of NAFLD thereof in a mammal including a human, and a pharmaceutically acceptable excipient, carrier, or diluent.

In one feature, the NAFLD is non-alcoholic steatohepatitis (NASH). In another feature, the NAFLD is simple steatosis or fatty liver.

In one aspect, the invention provides a method for reducing, ameliorating, or eliminating mortality or morbidity, including at least a symptom or indication, that is known to be associated with NAFLD (e.g., NASH) in a mammal including a human, comprising administering to a mammalian subject in need thereof: a therapeutically effective amount of a pharmaceutical composition comprising the compound of the invention, or an enantiomer, diastereomer, tautomer, or pharmaceutically acceptable salt, solvate, ester or pro-drug thereof that is effective in reducing, ameliorating, or eliminating at least a symptom or indication of NAFLD in a mammal including a human, and a pharmaceutically acceptable excipient, carrier, or diluent.

In various embodiments, the symptom or indication known to be associated with NAFLD or NASH that is being reduced, ameliorated, or eliminated is selected from the group consisting of: accumulation of liver fat, elevated level of hepatic triglyceride, heptic fibrosis, lobular inflammation, hepatocyte ballooning, elevated levels of liver enzymes aspartate aminotransferase (AST) and/or alanine aminotransferase (ALT), and an NAFLD Activity Score (NAS) greater than 3.

In one feature, the methods of the invention further include an additional step of administering an additional agent selected from the group consisting of: a vitamin, a lipid-lowering medication, an insulin-sensitizing medication, an anti-inflammation medication, a cholesterol-lowering medication, a diabetes medication, an experimental anti-NASH agent, and a weight-loss medication. The anti-inflammation medication can be an anti-oxidant medication, anti-apoptotic medication, or anti-cytokine medication. The vitamin can be, e.g., vitamin D or E. The experimental anti-NASH agent can be, e.g.: farnesoid x receptor agonists, PPAR agonists, Acetyl-CoA carboxylase (ACC), C—C chemokine ligands type 2 and type 5 antagonists, apoptosis signal-regulating kinase (ASK1) inhibitors, lysyl oxidase-like 2 antibody, an anti-hepatofibrotic agent, or galectin-3 inhibitors.

In various embodiments, the compound of the invention is one of Formulas I-X as described below in the detailed description of the invention.

In various embodiments, the compound of the invention is one of the following eight compounds as described in more detail hereinafter: compound 5, compound 7-1, compound 18-5, compound 18-2, compound 13-3, compound 9, compound 12 and compound 10-1.

In further embodiments, the compound of the invention is one of the following fifteen compounds as described in more detail hereinafter: compound 13-3-1, compound 13-3-2, compound 13-3-3, compound 13-3-5, compound 13-3-6, compound 13-3-7, compound 13-3-10, compound 13-3-11, compound 001, compound 004, compound 006, compound 013, compound 132, compound 133, and compound 134.

In yet another aspect, the invention generally relates to a pharmaceutical composition comprising a compound disclosed herein, or a pharmaceutically acceptable salt, solvate, ester or pro-drug thereof, and a pharmaceutically acceptable excipient, carrier, or diluent, as well as uses thereof.

In a feature, the invention generally relates to a method of treating NASH patient using one or more compositions disclosed herein such that at least one of the symptoms associated with NASH is improved. Treatment may further comprise the additional step of evaluating the success of the treatment by evaluating the subject/patient before and during treatment.

BRIEF DESCRIPTION OF THE DRAWINGS

FIGS. 1A-1C show quantification data on accumulation of intracellular triglycertide when various embodiments of the compound of the invention are each used in a given sample: Compound 13-3 (*: DMSO vs Compound 13-3 in corresponding culture media; #: control medium (left two columns) vs palmitoleic acid (POA) medium (right two columns); $p<0.05$) (FIG. 1A); effects from nine other embodiments in POA medium compared to that of Compound 13-3 (FIG. 1B); effects from seven different embodiments in POA medium compared to that of Compound 13-3 (FIG. 1C).

FIGS. 3A-3C present in vivo animal data on: (3A) macroscopic overview of the liver, (3B) decrease in liver weight, and (3C) liver/body weight ratio comparison at the time of euthanasia showing marked improvement in NAFLD/NASH pathology through Compound 13-3 treatment.

FIGS. 6A-6D present in vivo animal data on: (6A) Compound 13-3 decreases the hepatic triglyceride content; (6B) Compound 13-3 suppresses ALT elevation as a measure of liver injury; (6C) AST is not affected by HFD or Compound 13-3 treatment; and (6D) the decrease in AST:ALT ratio is prevented by Compound 13-3 treatment.

FIGS. 8A-8D present in vivo animal data on gene expression level of PPAR-γ (8A), protein expression of PPAR-γ in the liver (8B), gene expression levels of FABP4 (8C) and CD36 (8D).

DEFINITIONS

Figures 1A, 1B:
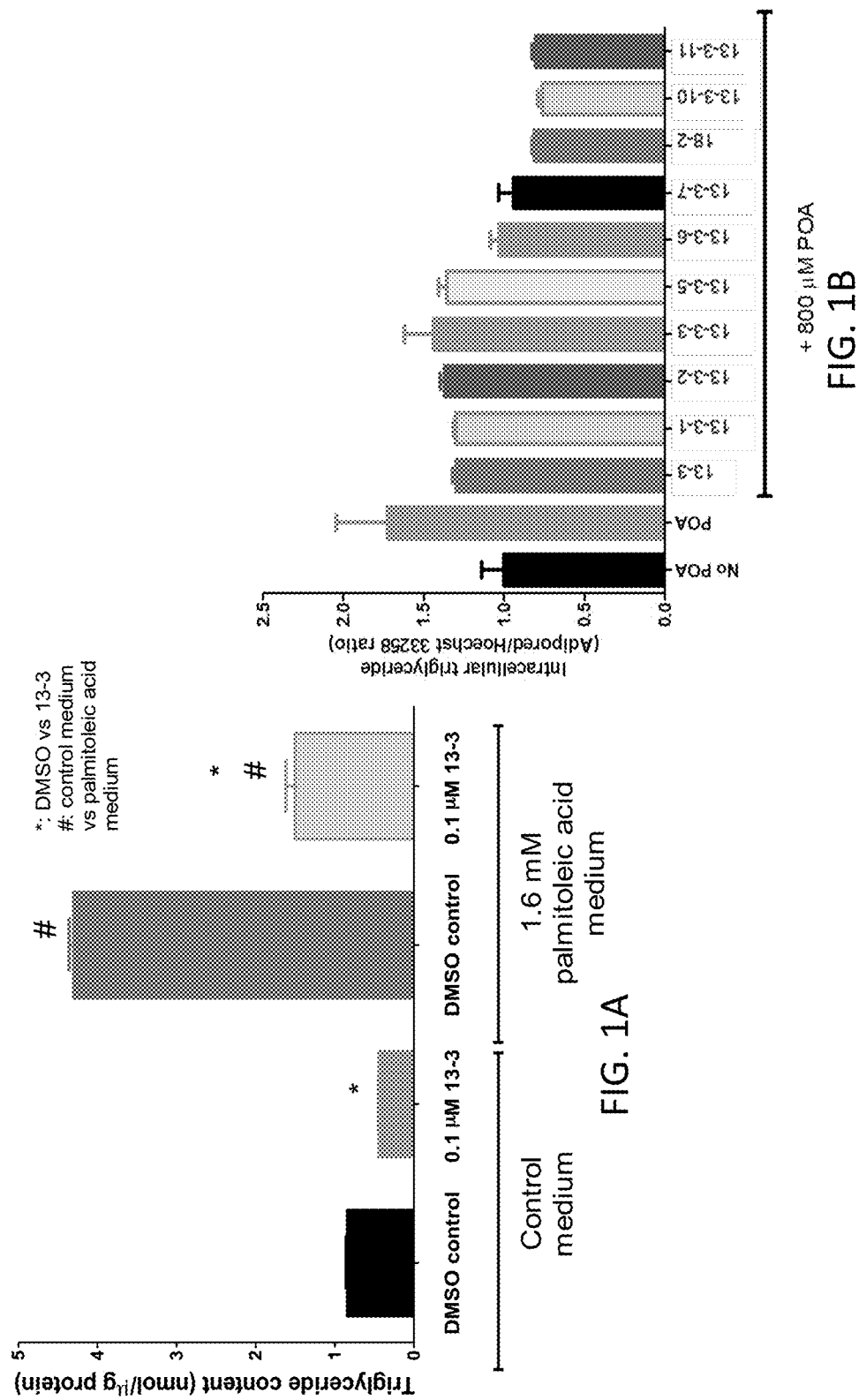
FIGS. 1A-1C present data on tests designed to see if compounds of the invention had any effect on triglycertide accumulation in human liver cell culture.

As used in the specification and claims, the singular form "a", "an", or "the" includes plural references unless the context clearly dictates otherwise. For example, the term "a cell" includes a plurality of cells including mixtures thereof.

As used herein, the term "about" or "approximately" when used in conjunction with a number refers to any number within 5, 10 or 15% of the referenced number.

As used herein, the term "subject" refers to any animal (e.g., a mammal), including, but not limited to humans, non-human primates, rodents, canines, and the like, which is to be the recipient of a particular treatment. Typically, the terms "subject" and "patient" are used interchangeably herein in reference to a human subject.

As used herein, "nonalcoholic fatty liver," "fatty liver," "steatosis" or "NAFL," refers to the presence of hepatic steatosis with no evidence of hepatocellular injury in the form of ballooning of the hepatocytes.

As used herein, "nonalcoholic steatohepatitis" or "NASH" is defined as the presence of hepatic steatosis and inflammation (steatohepatitis) with hepatocyte injury (ballooning) with or without fibrosis. Nonalcoholic steatohepatitis can progress to cirrhosis, liver failure, and even liver cancer. Currently, NASH is diagnosed after imaging tests (such as ultrasound, CT scan, or magnetic resonance imaging [MM]) that reveal fat accumulation in the liver, and blood or liver function tests showing elevated levels of two liver enzymes (aspartate aminotransferase [AST] and alanine aminotransferase [ALT]). Multiple biomarkers have been evaluated for non-invasive diagnosis of NASH. However, a percutaneous liver biopsy is still the gold standard for confirm a diagnosis; the minimal diagnostic criteria include: the presence of >5% macrovesicular steatosis, inflammation, and liver cell ballooning. In some cases, fibroscan is used as a noninvasive alterntive to liver biopsy for diagnosing NASH. Fibroscan uses ultrasound to determine how "stiff" the liver is and hence how much scarring there is in the liver and if cirrhosis has developed.

The composite NAS score is frequently used to describe the severity or to characterize pathological changes seen in NAFLD (Kleiner D E et al. *Hepatology.* 2005 41(6):1313-21). The NAS score includes scoring on steatosis, lobular inflammation, and hepatocellular ballooning/damage. A NAS score of 5-8 is largely considered diagnostic for NASH, while a score of 3-4 is often considered borderline and a score of 0-2 is considered negative for NASH.

As used herein, the terms "treat", "treating", and "treatment" have their ordinary and customary meanings, and include one or more of: blocking, ameliorating, or decreasing in severity, frequency and/or progression of a symptom of a disease or condition (e.g., NAFLD) or inducing regression or stasis of the disorder or disease in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 95%, 90%, 80%, 70%, 60%, 50%, 40%, 30%, 20%, 10%, or 5% versus a subject in which the methods of the present invention have not been practiced. Treatment can be for an existing condition or prophylactically for future conditions.

As used herein, the terms "inhibiting", "to inhibit" and their grammatical equivalents, when used in the context of a bioactivity, refer to a down-regulation of the bioactivity, which may reduce or eliminate the targeted function, such as the production of a protein or the phosphorylation of a molecule. In particular embodiments, inhibition may refer to a reduction of about 20%, 30%, 40%, 50%, 60%, 70%, 80%, 90% or 95% of the targeted activity. When used in the context of a disorder or disease, the terms refer to success at preventing or significantly delaying the onset of symptoms, alleviating symptoms, or eliminating the disease, condition or disorder.

As used herein the terms "administration," "administering," or the like, when used in the context of providing a pharmaceutical composition to a subject generally refers to providing to the subject one or more pharmaceutical compositions comprising the compound of the invention in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intraperitoneal, transdermal, or buccal routes of delivery.

Definitions of specific functional groups and chemical terms are described in more detail below. General principles of organic chemistry, as well as specific functional moieties and reactivity, are described in "Organic Chemistry", by Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in "Protective Groups in Organic Synthesis", Third Ed. Greene, T. W. and Wuts, P. G., Eds., John Wiley & Sons, New York: 1999.

It will be appreciated that the compounds, as described herein, may be substituted with any number of substituents or functional moieties. Throughout the specifications, groups and substituents thereof may be chosen to provide stable moieties and compounds.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "pharmaceutically acceptable salt" refers to either a pharmaceutical acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

The compounds of the present invention may form salts that are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps that may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention that contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable ester," refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

As used herein, the term "prodrug" refers to a pharmacological derivative of a parent drug molecule that requires biotransformation, either spontaneous or enzymatic, within the organism to release the active drug. For example, prodrugs are variations or derivatives of the compounds of Formula I that have groups cleavable under certain metabolic conditions, which when cleaved, become the compounds of Formula I. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism (See, Bundgard, Design of Prodrugs, pp. 7-9,21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, "$C_x$-$C_y$" refers in general to groups that have from x to y (inclusive) carbon atoms. Therefore, for example, "$C_1$-$C_6$" refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the various combinations between 1 and 20 (inclusive) carbon atoms, such as $C_1$-$C_6$, $C_1$-$C_{12}$ and $C_3$-$C_{12}$.

As used herein, the terms "alkyl" refers to a straight or branched chain alkane (hydrocarbon) radical. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include, but are not limited to, one or more of the following groups: hydrogen, halogen (e.g., a single halogen substituent or multiple halo substituents forming, in the latter case, groups such as $CF_3$ or an alkyl group bearing $Cl_3$), cyano, nitro, $CF_3$, $OCF_3$, cycloalkyl, alkenyl, cycloalkenyl, alkynyl, heterocycle, aryl, $OR_a$, $SR_a$, $S(=O)_2R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and $R_e$ is alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted. As used herein, the term "$C_x$-$C_y$ alkyl" refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc. Of course, other $C_1$-$C_{20}$ alkyl groups will be readily apparent to those of skill in the art given the benefit of the present disclosure. The term "alkyl" is $C_1$-$C_{20}$, preferably $C_1$-$C_{10}$, more preferably $C_1$-$C_6$, further preferably $C_1$-$C_6$.

As used herein, the term "alkenyl" refers to a straight or branched chain hydrocarbon radical having at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substituents can themselves be optionally substituted. The term "alkenyl" is $C_2$-$C_{20}$, preferably $C_2$-$C_{10}$, more preferably $C_2$-$C_6$.

As used herein, the term "alkynyl" refers to a straight or branched chain hydrocarbon radical having at least one carbon-to-carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents. The exemplary substituents can themselves be optionally substituted. The term "alkynyl" is $C_2$-$C_{20}$, preferably $C_2$-$C_{10}$, more preferably $C_2$-$C_6$.

As used herein, the term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" or "Substituted phenyl" refers to an aryl or a phenyl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substituents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "cycloalkyl" refers to a fully saturated cyclic hydrocarbon group having from 1 to 4 rings and 3 to 10 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted. The term "cycloalkyl" is $C_3$-$C_{10}$, preferably $C_3$-$C_8$, more preferably $C_3$-$C_6$.

As used herein, the term "cycloalkenyl" refers to a partially unsaturated cyclic hydrocarbon group containing 1 to 4 rings and 3 to 10 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted. The term "cycloalkenyl" is $C_3$-$C_{10}$, preferably $C_3$-$C_8$, more preferably $C_3$-$C_6$.

As used herein, the terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) that have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

As used herein, "substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, heterocyclic or substituted heterocyclic, aryl or substituted aryl, as well as those groups recited above as exemplary alkyl substituents. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

As used herein, the term "halogen" refers to fluorine (F), chlorine (Cl), bromine (Br), or iodine (I).

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents. The exemplary substituents can themselves be optionally substituted.

Unless otherwise indicated, any heteroatom with unsatisfied valences is assumed to have hydrogen atoms sufficient to satisfy the valences.

Isotopically labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

The term "hydrogen" refers to all hydrogen isotopes including protium and deuterium. In a given composition, the hydrogen molecules can be all protium, all deuterium, or a mixture of both, unless specified otherwise.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, esters, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates of the compounds of the invention are also contemplated herein. Solvates of the compounds of the present invention include, for example, hydrates.

DETAILED DESCRIPTION OF THE INVENTION

The invention provides compounds as well as pharmaceutical compositions containing such compounds and uses thereof in the treatment and prevention of diseases and disorders resulting from excessive fat accumulation in liver, e.g., NAFLD including simple steatosis and NASH, in a mammal.

Specifically, the present invention provides a pharmaceutical composition comprising any compound of the invention, or a pharmaceutically acceptable salt, salvate, ester or pro-drug thereof, and a pharmaceutically acceptable excipient, carrier, or diluent.

The invention also provides method for treating or preventing nonalcoholic fatty liver disease (NAFLD), e.g., NASH and steatosis, in a mammalian subject including a human, comprising administering to a mammalian subject in need thereof: a therapeutically effective amount of a pharmaceutical composition comprising any of the compound of the invention described herein, or an enantiomer, diastereomer, tautomer, or pharmaceutically acceptable salt, solvate, ester or pro-drug thereof that is effective in the treatment or prevention of NAFLD thereof in a mammal including a human, and a pharmaceutically acceptable excipient, carrier, or diluent.

In one feature, the invention provides a method that produces one or more of the following health benefits from successfully treating or preventing NAFLD or NASH, and possibly their comorbidities: a decrease in body weight and BMI; an improvement in liver function; and a decrease in at least one of hepatic triglyceride content, hepatic steatosis, inflammation, fibrosis, and liver injury.

In some embodiments, the invention generally relates to the use of a compound of Formula I,

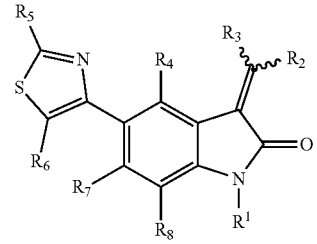

or an enantiomer, diastereomer, tautomer, or pharmaceutically acceptable salt or solvate thereof, for treating, therapeutically or prophylactically, NAFLD including NASH and simple steatosis, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_a$, $C(=O)R_a$, or $C(=O)NR_bR_c$;

$R_2$ is heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2O R_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ is hydrogen, halogen, cyano, nitro, $CF_3$, $OCF_3$, alkyl or substituted alkyl, heterocycle or substituted heterocycle, aryl or substituted aryl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula II,

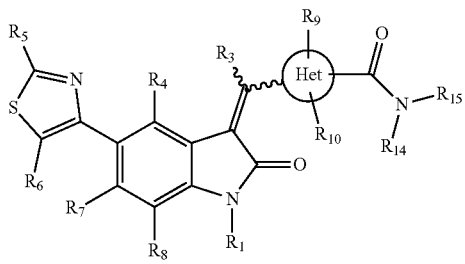

(II)

or an enantiomer, diastereomer, tautomer, or pharmaceutically acceptable salt or solvate thereof, for treating, therapeutically or prophylactically, NAFLD including NASH and simple steatosis, wherein the symbols have the following meanings and are, for each occurrence, independently selected:

Het is a 5- or 6-membered aromatic ring containing at least one heteroatom selected from N, O and S;

R1 is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

Ra is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula III,

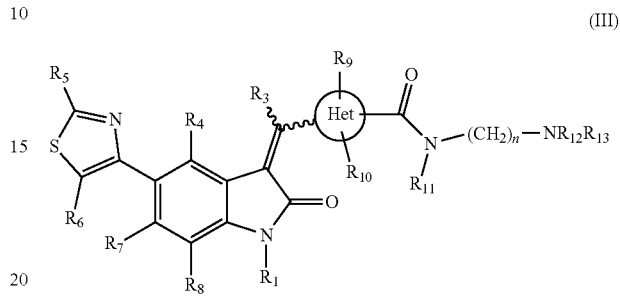

(III)

or an enantiomer, diastereomer, tautomer, or pharmaceutically acceptable salt or solvate thereof, for treating, therapeutically or prophylactically, NAFLD including NASH and simple steatosis, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{11}$ is hydrogen or $C_{1-4}$ alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle;

n is an integer selected from 2, 3, 4, 5 and 6;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula IV,

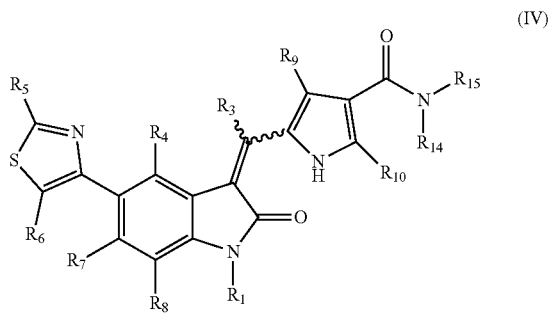

(IV)

or an enantiomer, diastereomer, tautomer, or pharmaceutically acceptable salt or solvate thereof, for treating, therapeutically or prophylactically, NAFLD including NASH and simple steatosis, wherein the symbols have the following meanings and are, for each occurrence, independently selected:

Het is a 5- or 6-membered aromatic ring containing at least one heteroatom selected from N, O and S;

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$;

$R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula V,

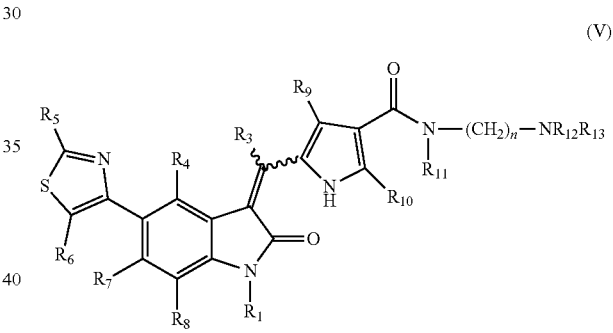

(V)

or an enantiomer, diastereomer, tautomer, or pharmaceutically acceptable salt or solvate thereof, for treating, therapeutically or prophylactically, NAFLD including NASH and simple steatosis, wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ and $R_{10}$ are each independently hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, P(=O)₂NR_bR_c, C(=O)OR_e, C(=O)R_a, C(=O)NR_bR_c, OC(=O)R_a, OC(=O)NR_bR_c, NR_bC(=O)OR_e, NR_dC(=O)NR_bR_c, NR_dS(=O)₂NR_bR_c, NR_dP(=O)₂NR_bR_c, NR_bC(=O)R_a, or NR_bP(=O)₂R_e;

R₅ is substituted alkyl, heterocycle or substituted heterocycle, aryl or substituted aryl, amino or substituted amino;

R₆ and R₉ are each independently hydrogen, halogen, cyano, nitro, CF₃, OCF₃, alkyl or substituted alkyl, heterocycle or substituted heterocycle, aryl or substituted aryl, or OR_a;

R₁₁ is hydrogen or C₁₋₄ alkyl;

R₁₂ and R₁₃ are independently hydrogen, alkyl or substituted alkyl, cycloalkyl or substituted cycloalkyl, heterocycle or substituted heterocycle, or aryl or substituted aryl, or said R₁₂ and R₁₃ together with the N to which they are bonded optionally form a heterocycle or substituted heterocycle;

n is an integer selected from 2, 3, 4, 5 and 6;

R_a is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R_b, R_c and R_d are independently hydrogen, alkyl or substituted alkyl, cycloalkyl or substituted cycloalkyl, heterocycle or substituted heterocycle, or aryl or substituted aryl, or said R_b and R_c together with the N to which they are bonded optionally form a heterocycle or substituted heterocycle; and R_e is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In various embodiments, the compound of the invention is one of the following eight compounds:

(5)

(7-1)

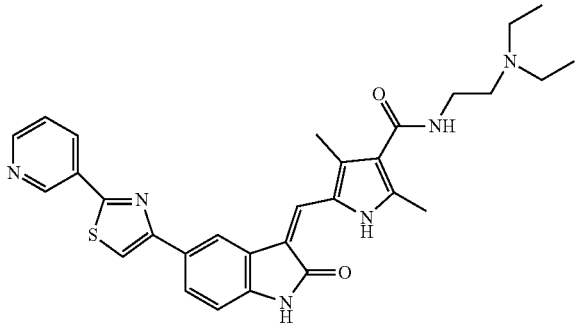
(18-5)

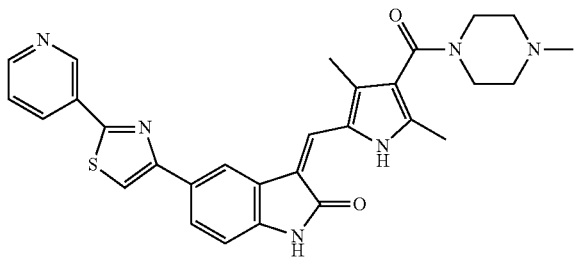
(18-2)

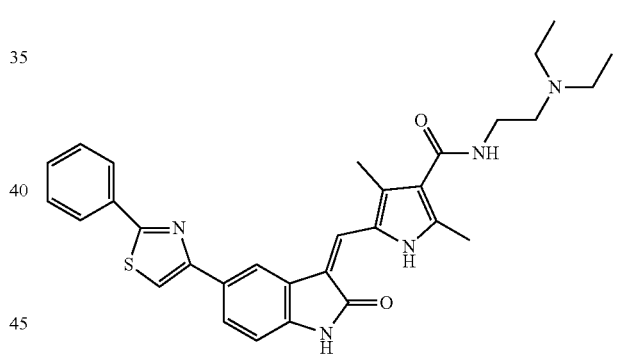
(13-3)

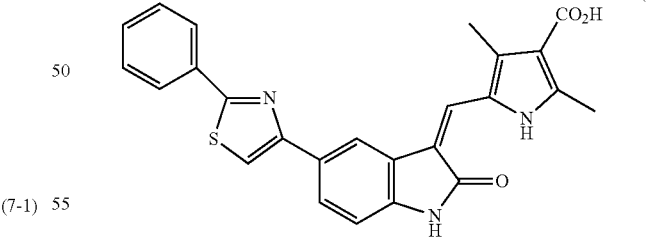
(9)

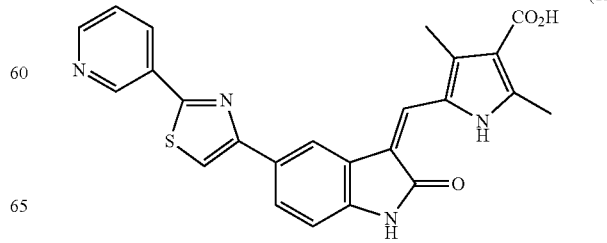
(12)

-continued (10-1)

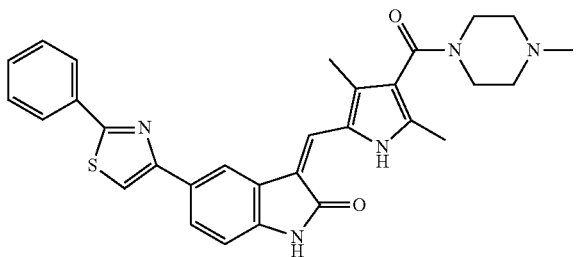

Item 1. In some embodiments, the invention generally relates to the use of a compound of Formula VI,

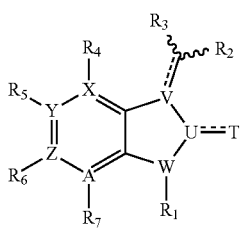

(VI)

or an enantiomer, diastereomer, tautomer, or pharmaceutically acceptable salt or solvate thereof, for treating, therapeutically or prophylactically, NAFLD including NASH and simple steatosis, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is monocyclic or bicyclic heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, or $S(O)_2NR_aR_b$;

$R_4$, $R_5$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

T is O, S or $R_a$;

U, V, and W are each independently a carbon, N, O, or S;

X, Y, Z, and A are each independently a carbon or N, with the proviso that the ring in which X, Y, Z, and A exist is aromatic;

with the provision that one of $R_4$, $R_5$, $R_6$, and $R_7$ is substituted heterocycle or substituted aryl, and $R_4$, $R_5$, $R_6$, or $R_7$ is absent if X, Y, Z, or A, respectively, is a heteroatom;

wherein substituted heterocycle and substituted aryl in $R_4$, $R_5$, $R_6$, and $R_7$ is the following group:

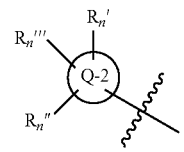

wherein

Q-2 is heterocycle, $C(=O)NR_bR_c$ or aryl;

$R_{n'}$, $R_{n''}$ and $R_{n'''}$ are each independently hydrogen, halogen, cyano, nitro, trihalomethyl, $OCF_3$, alkyl or substituted alkyl, $OR_a$, $SR_a$, $C(=O)R_a$, $C(=O)OR_a$, $NH_2$, $S(O)_2NH_2$, $NR_bR_c$, heterocycle or substituted heterocycle, or aryl or substituted aryl;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

Item 2. The compound of Item 1, wherein T is O or S,

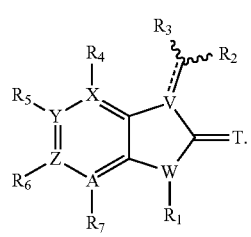

(VI-a)

Item 3. The compound of Item 2, wherein T is O,

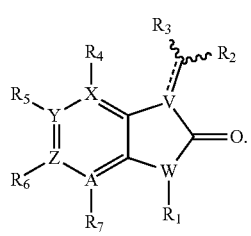

(VI-b)

Item 4. The compound of Item 2, wherein V is carbon,

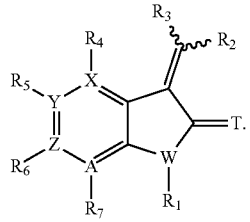
(VI-c)

Item 5. The compound of Item 2, wherein W is N,

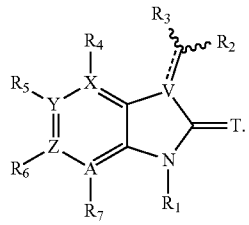
(VI-d)

Item 6. The compound of Item 5, wherein T is O and W is N,

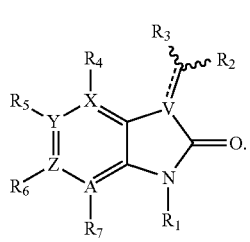
(VI-e)

Item 7. The compound of Item 4, wherein T is O and V is carbon,

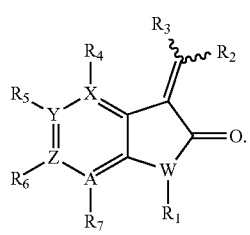
(VI-f)

Item 8. The compound of Item 1, wherein U is carbon, V is carbon, W is N, and T is O,

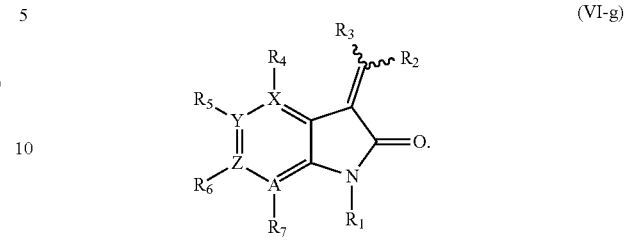
(VI-g)

Item 9. The compound of any one of Item 1 to Item 8, wherein each of X, Y, Z, and A is carbon.

Item 10. The compound of any one of Item 1 to Item 9, wherein $R_1$ is hydrogen.

Item 11. The compound of any one of Item 1 to Item 10, wherein $R_2$ is

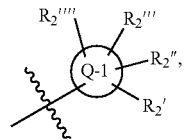

and wherein

Q-1 is heterocycle or aryl;

$R_{2'}$, $R_{2''}$, $R_{2'''}$, and $R_{2''''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$.

Item 12. The compound of Item 10 or Item 11, wherein at least one of X, Y, Z, and A is a heteroatom.

Item 13. The compound of any one of Items 10-12, wherein Q-1 is heteroaryl.

Item 13'. The compound of any one of Items 10-12, wherein Q-1 is phenyl.

Item 14. The compound of Item 13, wherein Q-1 is selected from the group consisting of pyrrole, furan, thiophene, pyridine, pyrimidine, pyrazine, pyridazine, imidazole, indole, pyrrolopyridinone, pyridone, pyrrolidine, piridinone, piperidine, and pyrroloazepinone.

Item 15. The compound of Item 14, wherein Q-1 is selected from the group consisting of pyrrole, furan, thiophene, pyridine, pyrimidine, pyrazine, pyridazine, imidazole, indole, pyrrolopyridinone.

Item 16. The compound of Item 15, wherein Q-1 is pyrrole.

Item 17. The compound of Item 13, wherein Q-1 is pyridone, pyrrolidine, pyridinone, or piperidine.

Item 18. The compound of Item 17, wherein Q-1 is pyridone or pyridinone.

Item 19. The compound of any one of items 11 to 18, wherein $R_{2'}$, $R_{2''}$, $R_{2'''}$, and $R_{2''''}$ are independently absent, hydrogen, alkyl, substituted alkyl, substituted heterocycle, substituted aryl, $C(=O)OR_e$, or $C(=O)NR_bR_c$, and wherein $R_b$ and $R_c$ are independently hydrogen, alkyl, substituted alkyl, substituted heterocycle, or said $R_b$ and $R_c$ together with the N to which they are bonded optionally form a heterocycle or substituted heterocycle, and $R_e$ is hydrogen.

Item 20. The compound of Item 19, wherein one of $R_{2'}$, $R_{2''}$, $R_{2'''}$, and $R_{2''''}$ is $C(=O)NR_bR_c$, and wherein $R_b$ is hydrogen, and $R_c$ is alkyl substituted with $NR_{bn}R_{cn}$ (wherein $R_{bn}$ and $R_{cn}$ are alkyl, or said $R_{bn}$ and $R_{cn}$ together with the N to which they are bonded optionally form a substituted heterocycle (wherein said heterocycle is piperidine, or morpholine)), or $R_b$ and $R_c$ together with the N to which they are bonded optionally form a substituted heterocycle (wherein said heterocycle is piperidine, or morpholine), and two of $R_{2'}$, $R_{2''}$, $R_{2'''}$, and $R_{2''''}$ are independently alkyl, and the other is hydrogen.

Item 21. The compound of Item 20, wherein one of $R_{2'}$, $R_{2''}$, $R_{2'''}$, and $R_{2''''}$ is $C(=O)NR_bR_c$, and wherein $NR_bR_c$ is 2-(di-ethyl amino) ethyl amino, 2-pyrrolidino ethyl amino, 4-methyl piperazinyl, or morpholino.

Item 21'. The compound of Item 16, wherein Q-1 is pyrrole, one of $R_{2'}$, $R_{2''}$, $R_{2'''}$, and $R_{2''''}$ is absent, two of $R_{2'}$, $R_{2''}$, $R_{2'''}$, and $R_{2''''}$ are alkyl (e.g., methyl), and one of $R_{2'}$, $R_{2''}$, $R_{2'''}$, and $R_{2''''}$ is $C(=O)NR_bR_c$.

Item 21''. The compound of Item 21', wherein $R_b$ is hydrogen, and $R_c$ is alkyl substituted with $NR_{bn}R_{cn}$ (wherein $R_{bn}$ and $R_{cn}$ are alkyl, or said $R_{bn}$ and $R_{cn}$ together with the N to which they are bonded optionally form a substituted heterocycle (wherein said heterocycle is piperidine, or morpholine)).

Item 21'''. The compound of Item 21'', wherein $NR_bR_c$ is 2-(di-ethyl amino) ethyl amino, or 2-pyrrolidino ethyl amino.

Item 21''''. The compound of Item 21', wherein $R_b$ and $R_c$ together with the N to which they are bonded optionally form a heterocycle or substituted heterocycle.

Item 21'''''. The compound of Item 21'''', wherein $NR_bR_c$ is 4-methyl piperazinyl, or morpholino.

Item 22. The compound of any one of Items 1 to 21, wherein $R_4$, $R_5$, $R_6$, and $R_7$ are each independently hydrogen, halogen, cyano, nitro, alkyl or substituted alkyl, $OR_a$, $NR_bR_c$, $C(=O)OR_e$, $C(=O)R_a$, $C(=O)NR_bR_c$, or

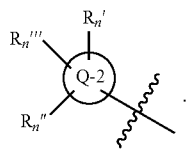

Item 23. The compound of any one of Items 1 to 22, wherein $R_4$, $R_5$, $R_6$, and $R_7$ are each independently hydrogen, halogen, cyano, nitro, alkyl, $OR_a$, $NR_bR_c$, $C(=O)OR_e$, $C(=O)R_a$, $C(=O)NR_bR_c$, and wherein $R_a$ is hydrogen, or alkyl or substituted alkyl, $R_b$ and $R_c$ are independently hydrogen, or alkyl or substituted alkyl, and $R_e$ is alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle.)), and

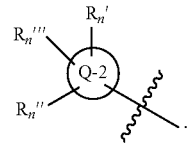

Item 24. The compound of Item 23, wherein one of $R_4$, $R_5$, $R_6$, and $R_7$ is

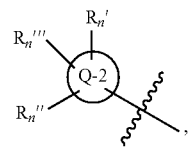

the others of $R_4$, $R_5$, $R_6$, and $R_7$ are each independently hydrogen.

Item 25. The compound of Item 24, wherein Q-2 is selected from the group consisting of pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, oxepane, indole, indolinone, indazole, benzothiazole, quinoline, quinazoline, quinoxaline, imidazopyridine, imidazopyridazine, pyrazolopyridine, pyrazolopyrimidine, phthalazinone, and phenyl.

Item 26. The compound of Item 25, wherein Q-2 is selected from the group consisting of pyrrole, furan, thiophene, imidazole, pyrazole, oxazole, isoxazole, thiazole, isothiazole, triazole, thiadiazole, oxadiazole, pyrrolidine, piperidine, azepane, tetrahydrofuran, oxane, oxepane, indole, indolinone, indazole, benzothiazole, quinoline, quinazoline, quinoxaline, imidazopyridine, imidazopyridazine, pyrazolopyridine, pyrazolopyrimidine, and phthalazinone.

Item 27. The compound of Item 26, wherein Q-2 is selected from the group consisting of thiophene, imidazole, oxazole, thiazole, thiadiazole, piperidine, and pyrazole.

Item 27'. The compound of Item 26, wherein Q-2 is selected from the group consisting of indole, indolinone, indazole, benzothiazole, quinoline, quinazoline, quinoxaline, imidazopyridine, imidazopyridazine, pyrazolopyridine, pyrazolopyrimidine, and phthalazinone.

Item 28. The compound of Item 27, wherein Q-2 is thiazole.

Item 29. The compound of Item 27, wherein Q-2 is imidazole.

Item 30. The compound of Item 27, wherein Q-2 is piperidine.

Item 31. The compound of Item 27, wherein Q-2 is pyrazole.

Item 32. The compound of any one of Items 22 to 25, wherein $R_{n'}$ is pyrrolidinyl, piperidinyl, azepanyl, tetrahydrofuranyl, oxanyl, oxepanyl, pyranyl, phenyl, thiophenyl, pyrazinyl, pyrimidinyl, pyridazinyl, or pyridyl (said piperidinyl, pyranyl, phenyl, thiophenyl, pyrazinyl, pyrimidinyl, pyridazinyl, and pyridyl are optionally substituted with halogen, cyano, nitro, alkyl or substituted alkyl, $OR_a$, $NR_bR_c$, $C(=O)OR_e$, $C(=O)R_a$, or $C(=O)NR_bR_c$ (wherein $R_a$ is hydrogen, or alkyl or substituted alkyl, $R_b$ and $R_c$ are independently hydrogen, or alkyl or substituted alkyl, and $R_e$ is alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle.)), and wherein $R_{n''}$ and $R_{n'''}$ are independently hydrogen, or alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle).

Item 32'. The compound of any one of Items 22 to 25, wherein $R_{n'}$, $R_{n''}$ and $R_{n'''}$ are independently hydrogen, alkyl, or methoxy.

Item 32". The compound of any one of Items 22 to 25, wherein $R_{n'}$, $R_{n''}$ and $R_{n'''}$ are each hydrogen.

Item 33. The compound of Item 32, wherein $R_{n'}$ is pyrrolidinyl, piperidinyl, tetrahydrofuranyl, pyranyl, phenyl, pyrazinyl, pyrimidinyl, or pyridyl (said piperidinyl, pyranyl, phenyl, pyrazinyl, pyrimidinyl, and pyridyl are optionally substituted with halogen, cyano, alkyl or substituted alkyl, $OR_a$, or $C(=O)OR_e$ (wherein $R_a$ is hydrogen, or alkyl or substituted alkyl, and $R_e$ is alkyl or substituted alkyl (substituted alkyl is optionally substituted with one or more substituent(s) selected from the group consisting of hydroxy, amino, nitro, cyano, halogen, alkoxy, alkylcarbonyl, alkoxycarbonyl, aminocarbonyl, aryl, cycloalkyl, and heterocycle.)), and wherein $R_{n''}$ and $R_{n'''}$ are independently hydrogen, alkyl, or amino.

Item 33'. The compound of Item 33, wherein $R_{n'}$ is phenyl or substituted phenyl, and $R_{n''}$ and $R_{n'''}$ are independently hydrogen, or alkyl or amino.

Item 34. The compound of Item 33, wherein $R_{n''}$ and $R_{n'''}$ are independently hydrogen or alkyl.

Item 35. The compound of Item 32 or 33, wherein Q-2 is selected from the group consisting of the following groups:

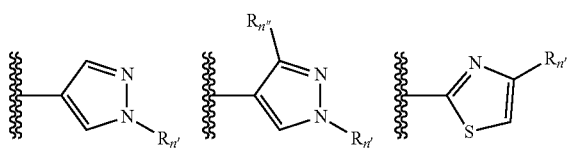

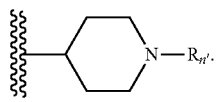

Item 36. The compound of Item 32 or 33, wherein Q-2 is selected from the group consisting of the following group:

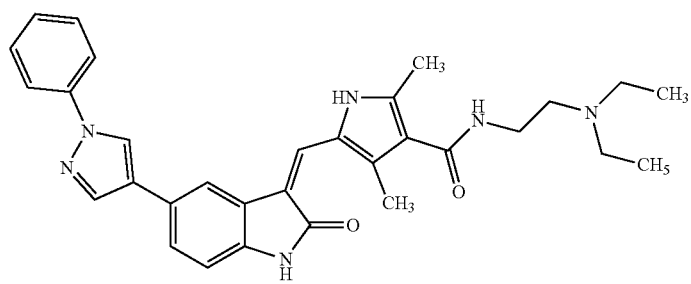

Item 37. The compound of any one of Item 1, selected from the group consisting of:

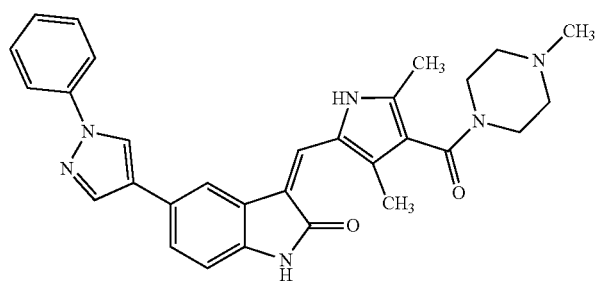

-continued
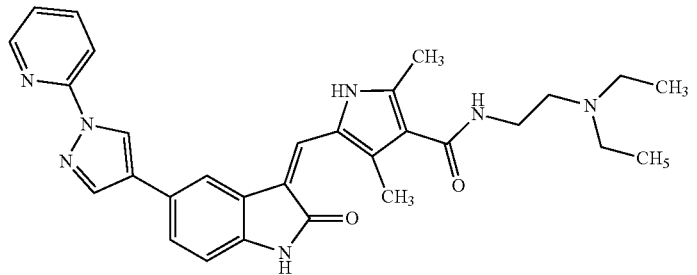
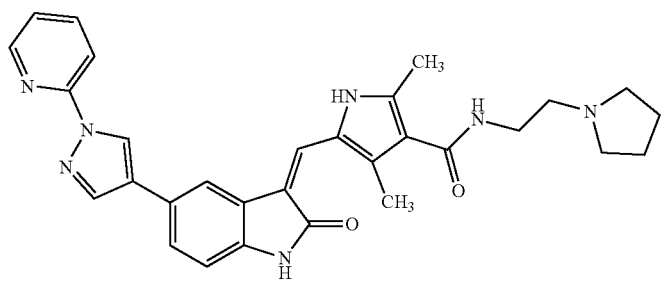
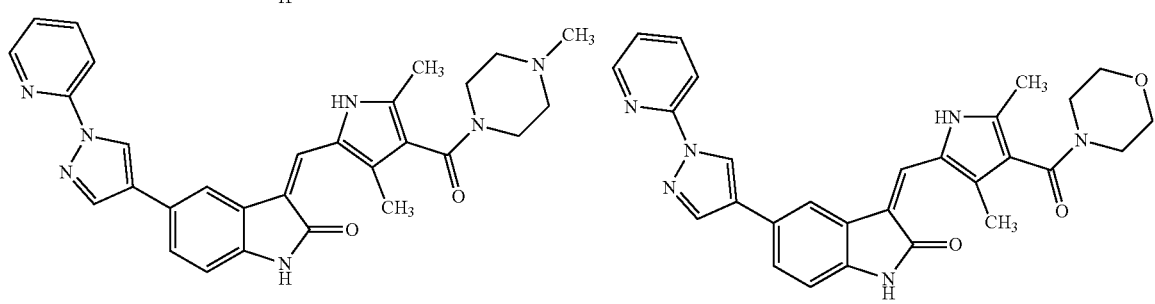
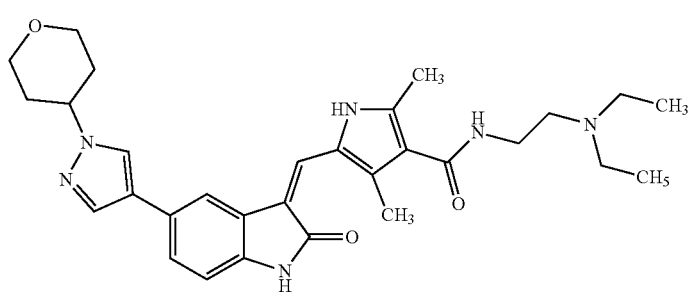
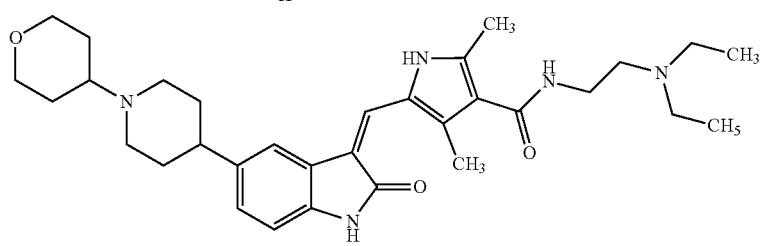
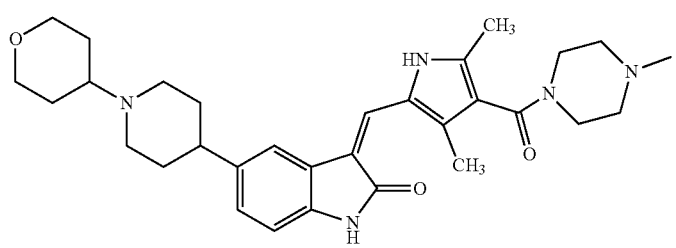

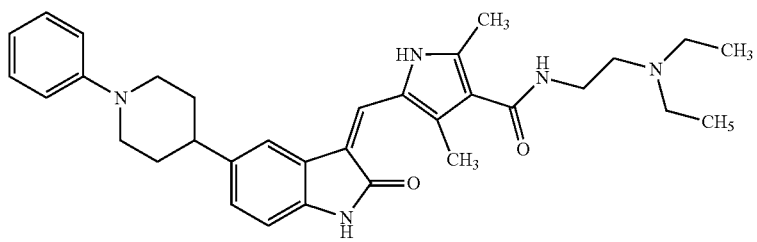
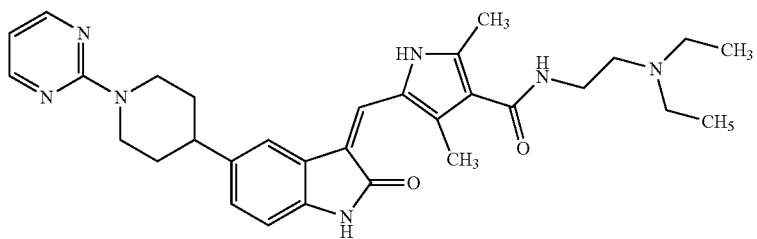
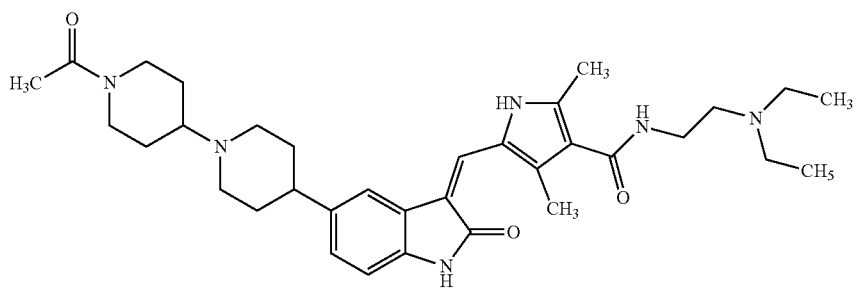
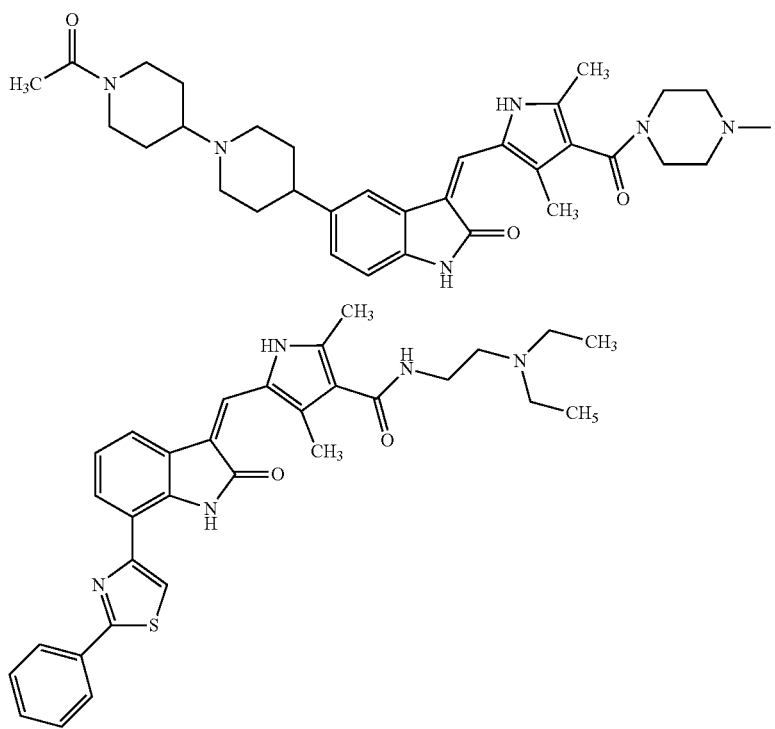

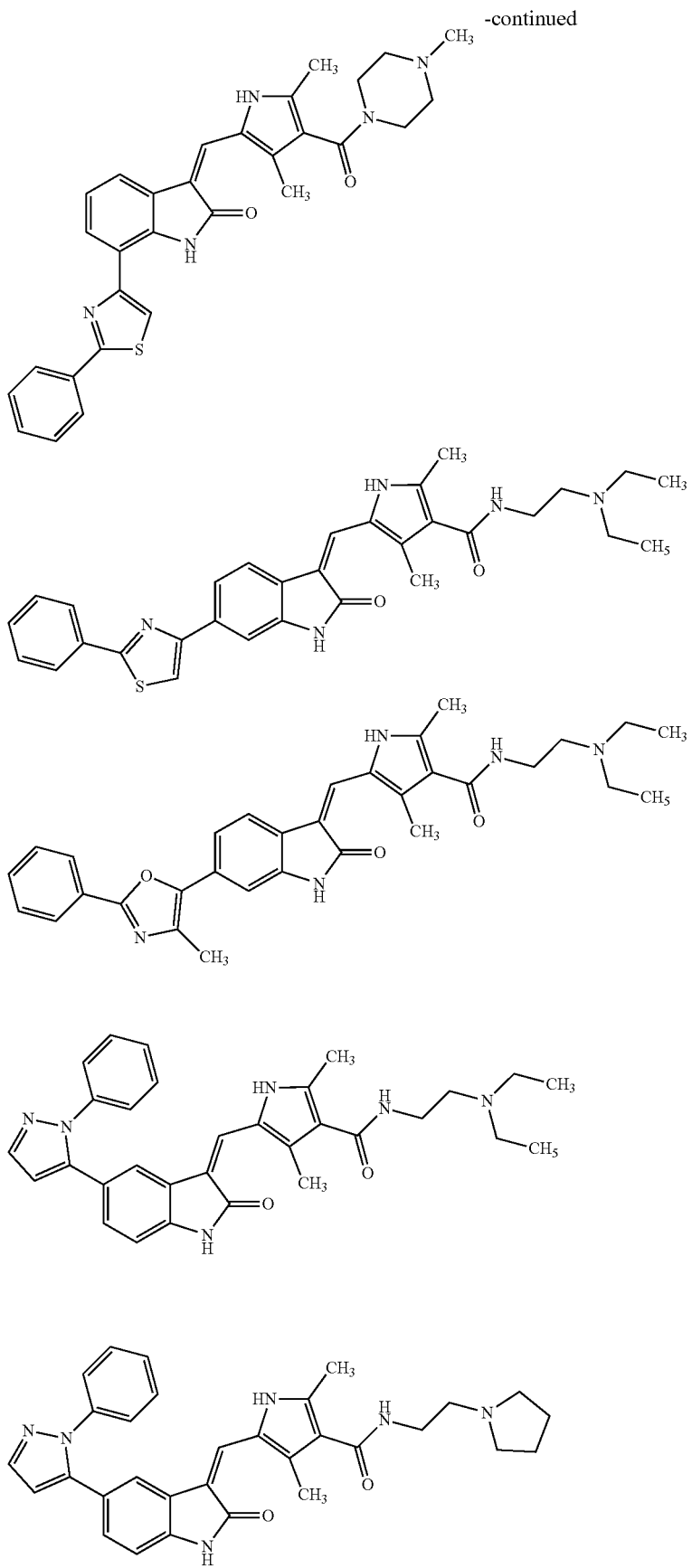

In some embodiments, the invention generally relates to the use of a compound of Formula VII,

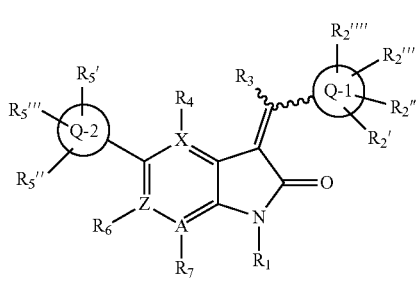
(VII)

or an enantiomer, diastereomer, tautomer, or pharmaceutically acceptable salt or solvate thereof, for treating, therapeutically or prophylactically, NAFLD including NASH and simple steatosis, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, $-OR_a$, $-C(O)R_a$, $-C(O)OR_a$, $-NR_aR_b$, or $S(O)_2NR_aR_b$;

$R_4$, $R_6$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Z, and A are each independently a carbon or N, with the proviso that the ring in which X, Z, and A exist is aromatic;

Q-1 and Q-2 are independently heterocycle, $C(=O)NR_bR_c$ or aryl;

$R_{2'}$, $R_{2''}$, $R_{2'''}$ and $R_{2''''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, $R_{5'}$, $R_{5''}$ and $R_{5'''}$ are each independently hydrogen, halogen, cyano, nitro, $CF_3$, $OCF_3$, alkyl or substituted alkyl, $OR_a$, $SR_a$, $C(=O)R_a$, $C(=O)OR_a$, $NH_2$, $S(O)_2NH_2$, $NR_bR_c$, heterocycle or substituted heterocycle, or aryl or substituted aryl;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the compound of formula (VII), wherein each of X, Z, and A is carbon. In some embodiments, the compound of formula (VII), wherein one of X, Z, and A is a heteroatom.

In some embodiments, the compound of formula (VII) has the formula (VII-a)

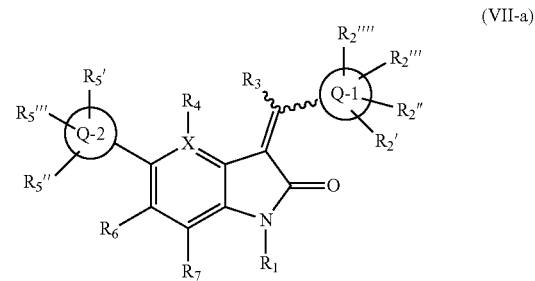
(VII-a)

wherein $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, $R_7$, X, Q-1, and Q-2 are the same as the above definitions.

In some embodiments, the compound of formula (VII) has the formula (VII-b)

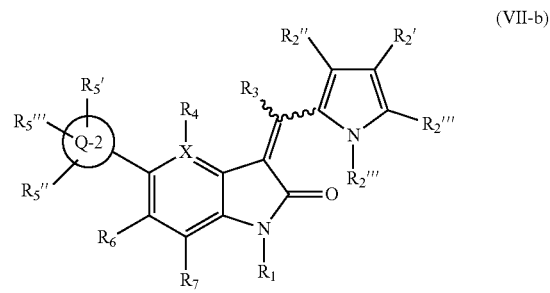
(VII-b)

wherein $R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, $R_1$, $R_3$, $R_4$, $R_{5'}$, $R_{5''}$, $R_{5'''}$, $R_6$, $R_7$, X, and Q-2 are the same as the above definitions.

In some embodiments, the compound of formula (VII-b), wherein X is C. In some embodiments, the compound of formula (VII-b), wherein X is N. In some embodiments, the compound of formula (VII-b), wherein $R_{2''''}$ is H. In some embodiments, the compound of formula (VII-b), wherein $R_{2''}$ and $R_{2'''}$ are each independently hydrogen. In some embodiments, the compound of formula (VII-b), wherein $R_{2''}$ and $R_{2'''}$ are each independently methyl.

In some embodiments, the compound of formula (VII) has the formula (VII-c)

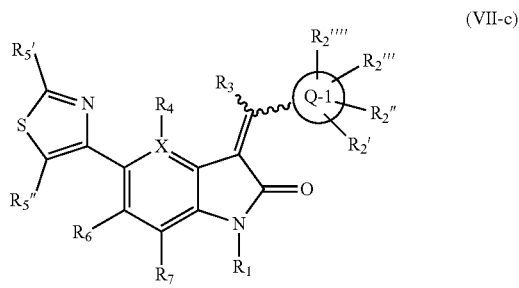

(VII-c)

wherein
$R_1$, $R_{2'}$, $R_{2''}$, $R_{2'''}$, $R_{2''''}$, $R_3$, $R_4$, $R_{5'}$, $R_{5''}$, $R_6$, $R_7$, X, and Q-1 are the same as the above definitions.

In some embodiments, the compound of formula (VII) has the formula (VII-d)

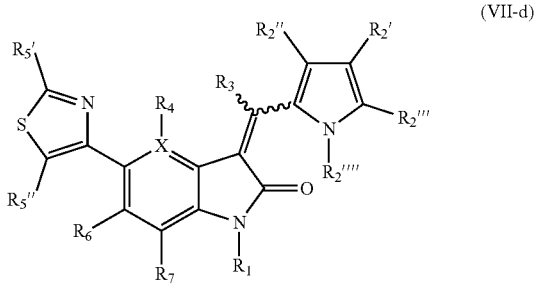

(VII-d)

wherein
X is C or N,
$R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_6$, and $R_7$, are the same as the above definitions.

In some embodiments, the compound of formula (VII) has the formula (VII-e)

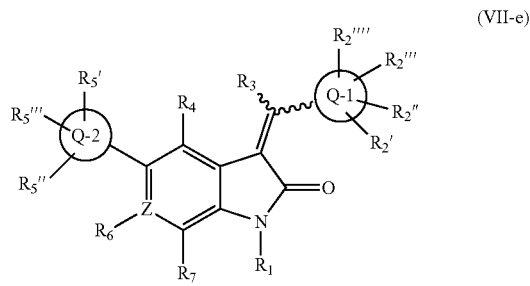

(VII-e)

wherein
Z is C or N,
$R_1$, $R_{2'}$, $R_{2''}$, $R_{2'''}$, $R_{2''''}$, $R_3$, $R_4$, $R_{5'}$, $R_{5''}$, $R_{5'''}$, $R_6$, $R_7$, Q-1, and Q-2 are the same as the above definitions.

In some embodiments, the compound of formula (VII) has the formula (VII-f)

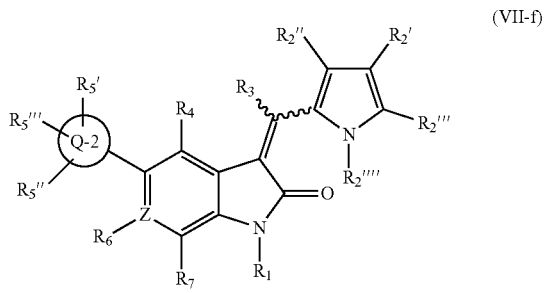

(VII-f)

wherein
Z is C or N,
$R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_{5'''}$, $R_6$, $R_7$, and Q-2 are the same as the above definitions.

In some embodiments, the compound of formula (VII-f), wherein Z is C. In some embodiments, the compound of formula (VII-f), wherein Z is N. In some embodiments, the compound of formula (VII-f), wherein $R_{2''''}$ is H. In some embodiments, the compound of formula (VII-f), wherein $R_{2''}$ and $R_{2'''}$ are each independently hydrogen. In some embodiments, the compound of formula (VII-f), wherein $R_{2''}$ and $R_{2'''}$ are each independently methyl.

In some embodiments, the compound of formula (VII) has the formula (VII-g)

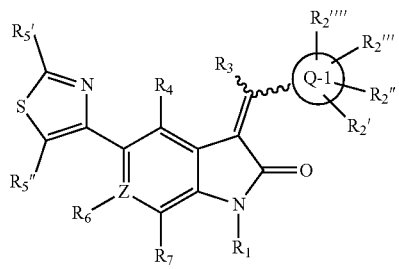

(VII-g)

wherein

Z is C or N, $R_1$, $R_{2'}$, $R_{2''}$, $R_{2'''}$, $R_{2''''}$, $R_3$, $R_4$, $R_{5'}$, $R_{5''}$, $R_6$, $R_7$, and Q-1 are the same as the above definitions.

In some embodiments, the compound of formula (VII) has the formula (VII-h)

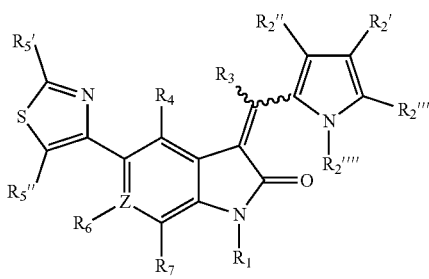

(VII-h)

wherein

Z is C or N, $R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_6$, and $R_7$, are the same as the above definitions.

In some embodiments, the compound of formula (VII) has the formula (VII-i)

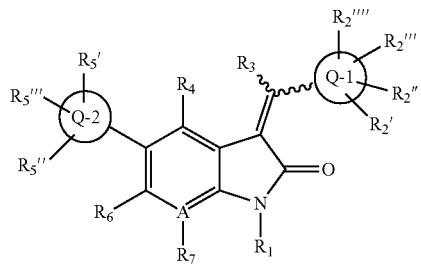

(VII-i)

wherein

A is C or N, $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, $R_7$, Q-1, and Q-2 are the same as the above definitions.

In some embodiments, the compound of formula (VII) has the formula (VII j)

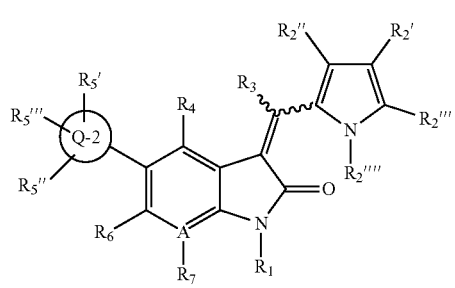

(VII-j)

wherein

A is C or N, $R_{2'}$, $R_{2''}$, $R_{2'''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_{5''''}$, $R_6$, $R_7$, and Q-2 are the same as the above definitions.

In some embodiments, the compound of formula (VII-j), wherein A is C. In some embodiments, the compound of formula (VII-j), wherein A is N. In some embodiments, the compound of formula (VII-j), wherein $R_{2''''}$ is H. In some embodiments, the compound of formula (VII-j), wherein $R_{2''}$ and $R_{2'''}$ are each independently hydrogen. In some embodiments, the compound of formula (VII-j), wherein $R_{2''}$ and $R_{2'''}$ are each independently methyl.

In some embodiments, the compound of formula (VII) has the formula (VII-k)

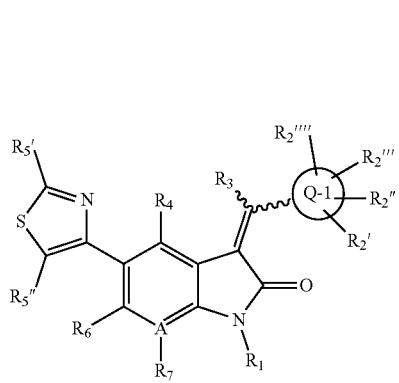

(VII-k)

wherein

A is C or N, $R_1$, $R_{2'}$, $R_{2''}$, $R_{2'''}$, $R_{2''''}$, $R_3$, $R_4$, $R_{5'}$, $R_{5''}$, $R_6$, $R_7$, and Q-1 are the same as the above definitions.

In some embodiments, the compound of formula (VII) has the formula (VII-l)

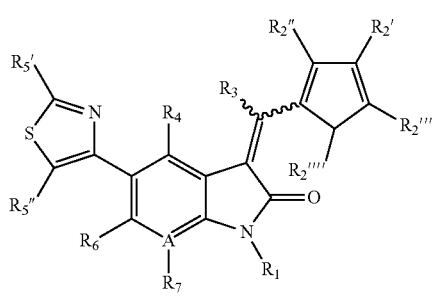

(VII-l)

wherein

A is C or N, $R_{2'}$, $R_2''$, $R_2'''$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, and $R_{2''''}$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, $C(=O)NR_bR_c$, and $R_1$, $R_3$, $R_4$, $R_{5'}$, $R_{5''}$, $R_6$, and $R_7$, are the same as the above definitions.

In some embodiments, the compound of formula (VII) has the formula (VII-m)

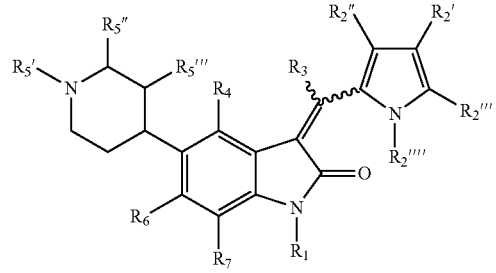

(VII-m)

wherein $R_1$, $R_{2'}$, $R_{2''}$, $R_{2'''}$, $R_{2''''}$, $R_3$, $R_4$, $R_{5'}$, $R_{5''}$, $R_{5'''}$, $R_6$, and $R_7$, are the same as the above definitions.

In some embodiments, the compound of formula (VII) has the formula (VII-n)

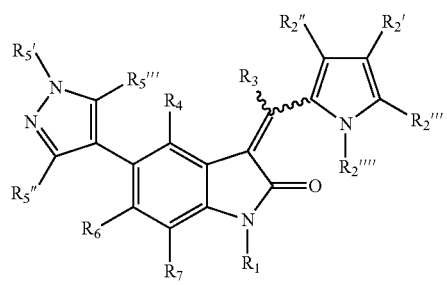

(VII-n)

wherein $R_1$, $R_{2'}$, $R_{2''}$, $R_{2'''}$, $R_{2''''}$, $R_3$, $R_4$, $R_{5'}$, $R_{5''}$, $R_{5'''}$, n, $R_6$, and $R_7$, are the same as the above definitions.

In some embodiments, the compound of formula (VII) has the formula (VII-o)

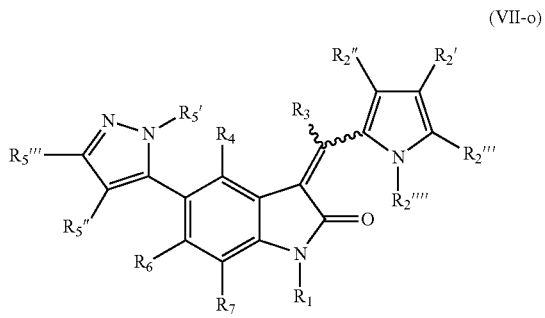

(VII-o)

wherein $R_1$, $R_{2'}$, $R_{2''}$, $R_{2'''}$, $R_{2''''}$, $R_3$, $R_4$, $R_{5'}$, $R_{5''}$, $R_{5'''}$, n, $R_6$, and $R_7$, are the same as the above definitions.

In some embodiments, the invention generally relates to the use of a compound of Formula VIII,

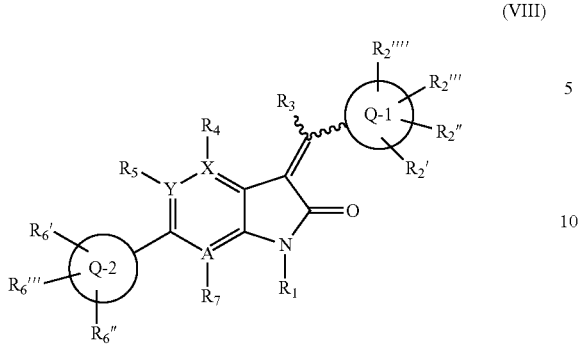

(VIII)

or an enantiomer, diastereomer, tautomer, or pharmaceutically acceptable salt or solvate thereof, for treating, therapeutically or prophylactically, NAFLD including NASH and simple steatosis, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, —$OR_a$, —$C(O)R_a$, —$C(O)OR_a$, —$NR_aR_b$, or $S(O)_2NR_aR_b$;

$R_4$, $R_5$, and $R_7$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Y, and A are each independently a carbon or N, with the proviso that the ring in which X, Y, and A exist is aromatic;

Q-1 and Q-2 are each independently heterocycle, $C(=O)NR_bR_c$ or aryl;

$R_{2'}$, $R_{2''}$, $R_{2'''}$ and $R_{2''''}$ are each independently absent, hydrogen, halogen, cyano, nitro, trihalomethyl, $OCF_3$, alkyl or substituted alkyl, cycloalkyl or substituted cycloalkyl, heterocycle or substituted heterocycle, aryl or substituted aryl, or $OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, $R_{6'}$, $R_{6''}$ and $R_{6'''}$ are each independently hydrogen, halogen, cyano, nitro, trihalomethyl, $OCF_3$, alkyl or substituted alkyl, $OR_a$, $SR_a$, $C(=O)R_a$, $C(=O)OR_a$, $NH_2$, $S(O)_2NH_2$, heterocycle or substituted heterocycle, or aryl or substituted aryl;

wherein $R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle; and $R_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula IX,

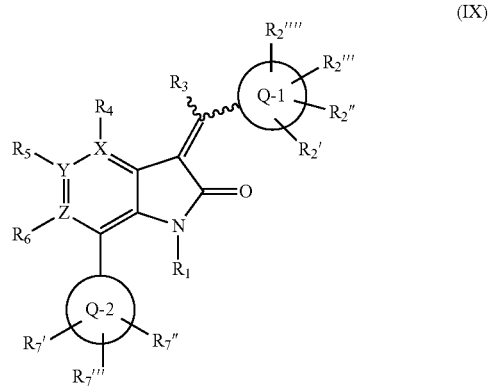

(IX)

or an enantiomer, diastereomer, tautomer, or pharmaceutically acceptable salt or solvate thereof, for treating, therapeutically or prophylactically, NAFLD including NASH and simple steatosis, wherein $R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_3$ is hydrogen, alkyl or substituted alkyl, cycloalkyl or substituted cycloalkyl, heterocycle or substituted heterocycle, aryl or substituted aryl, halogen, —$OR_a$, —$C(O)R_a$, —$C(O)OR_a$, —$NR_aR_b$, or $S(O)_2NR_aR_b$;

$R_4$, $R_5$, and $R_6$ are each independently hydrogen, halogen, cyano, nitro, trihalomethyl, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

X, Y, and Z are each independently a carbon or N, with the proviso that the ring in which X, Y, and Z exist is aromatic;

Q-1 and Q-2 are each independently heterocycle, C(=O)NR$_b$R$_c$ or aryl;

R$_{2'}$, R$_{2''}$, R$_{2'''}$ and R$_{2''''}$ are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, R$_{7'}$, R$_{7''}$ and R$_{7'''}$ are each independently hydrogen, halogen, cyano, nitro, trihalomethyl, OCF$_3$, alkyl or substituted alkyl, OR$_a$, SR$_a$, C(=O)R$_a$, C(=O)OR$_a$, NH$_2$, S(O)$_2$NH$_2$, heterocycle or substituted heterocycle, or aryl or substituted aryl;

wherein

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In some embodiments, the invention generally relates to the use of a compound of Formula X

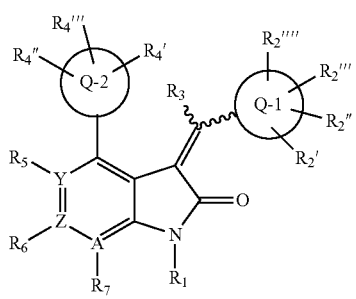

(X)

or an enantiomer, diastereomer, tautomer, or pharmaceutically acceptable salt or solvate thereof, for treating, therapeutically or prophylactically, NAFLD including NASH and simple steatosis, wherein R$_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)$_2$R$_e$, S(=O)$_2$OR$_e$, C(=O)OR$_d$, C(=O)R$_a$, or C(=O)NR$_b$R$_c$;

R$_3$ is hydrogen, alkyl or substituted alkyl, cycloalkyl or substituted cycloalkyl, heterocycle or substituted heterocycle, aryl or substituted aryl, halogen, —OR$_a$, —C(O)R$_a$, —C(O)OR$_a$, —NR$_a$R$_b$, or S(O)$_2$NR$_a$R$_b$;

R$_5$, R$_6$, and R$_7$ are each independently hydrogen, halogen, cyano, nitro, trihalomethyl, OCF$_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

Y, Z and A are each independently a carbon or N, with the proviso that the ring in which Y, Z and A exist is aromatic;

Q-1 and Q-2 are each independently heterocycle, C(=O)NR$_b$R$_c$ or aryl;

R$_{2'}$, R$_{2''}$, R$_{2'''}$, and R$_{2''''}$ are each independently absent, hydrogen, halogen, cyano, nitro, trihalomethyl, OCF$_3$, alkyl or substituted alkyl, cycloalkyl or substituted cycloalkyl, heterocycle or substituted heterocycle, aryl or substituted aryl, or OR$_a$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, R$_{4'}$, R$_{4''}$ and R$_{4'''}$ are each independently hydrogen, halogen, cyano, nitro, trihalomethyl, OCF$_3$, alkyl or substituted alkyl, OR$_a$, SR$_a$, C(=O)R$_a$, C(=O)OR$_a$, NH$_2$, S(O)$_2$NH$_2$, heterocycle or substituted heterocycle, or aryl or substituted aryl;

wherein

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle; and R$_e$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

In various embodiments, the compound of the invention is one of the following fifteen compounds:

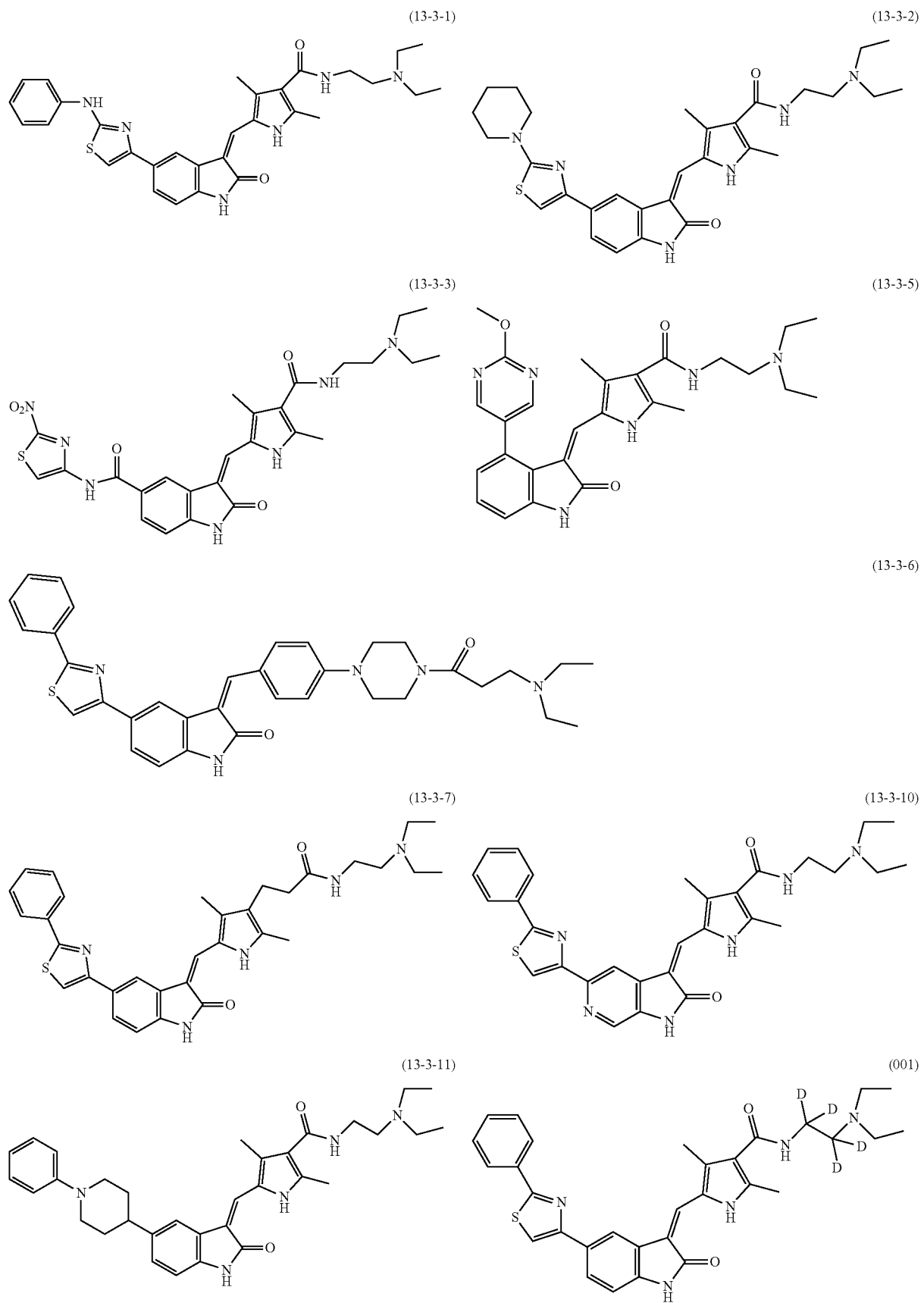

-continued (004)
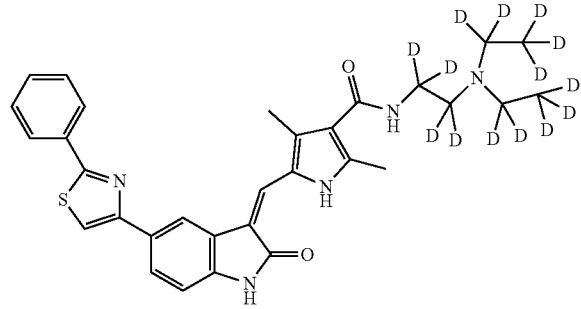

(006)
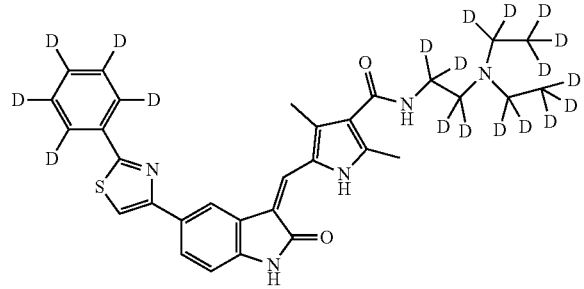

(013)
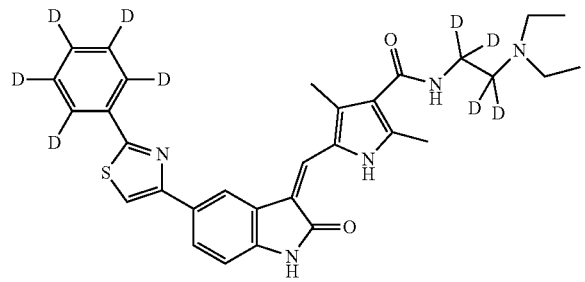

(132)
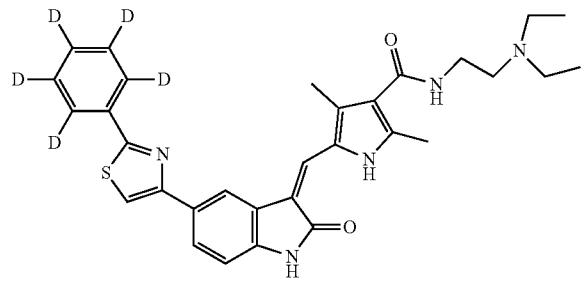

(133)
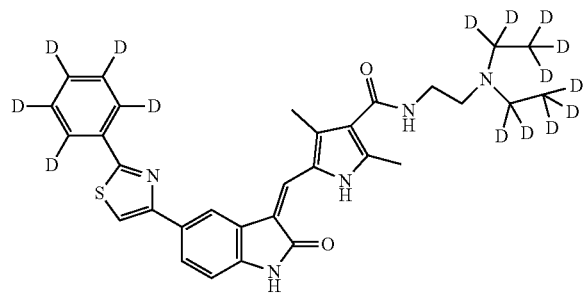

(134)
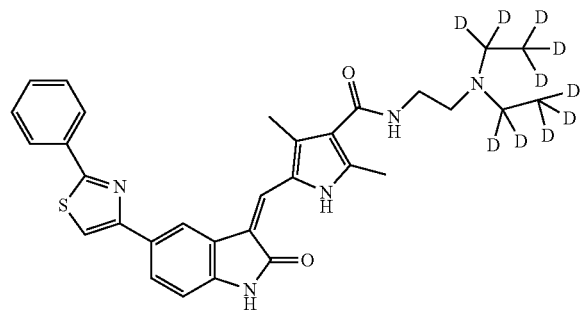

Synthesis

Exemplary methods for preparing compounds of the invention are provided in later sections, but the present invention is not intended to be limited thereto.

In the following exemplary methods for chemically synthesizing compounds of the invention, the starting materials and the intermediates of the reaction may be isolated and purified if desired using conventional techniques, including but not limited to filtration, distillation, crystallization, chromatography and the like.

The materials of invention can be characterized by using conventional means including but not limited to physical constants and spectral data. The reactions are performed in solvents appropriate to the reagents and materials employed and are suitable for transformations being effected. The representative examples include, but are not limited to, tetrahyrdofuran, dimethylforamide, methanol, ethanol, water, dimethylforamide, chloroform, dichloromethane, hexane, toluene, 1,4-dioxane or ethyl acetate.

Unless specified, the reactions described herein were performed at atmospheric pressure over a temperature range from about −78° C. to about 150° C.

For heating, any methods can be used which depends on reagent and target material. The representative examples include, but are not limited to, water bath, oil bath, water bath, or microwave reactor.

The compound of Formula VI in the present invention may be prepared from known compounds by optionally combining the method of the following Preparation methods I to II, similar methods to the following Preparation methods, or synthetic known to a skilled person.

Methods of Preparation

A compound of Formula VI may be synthesized by the following method:

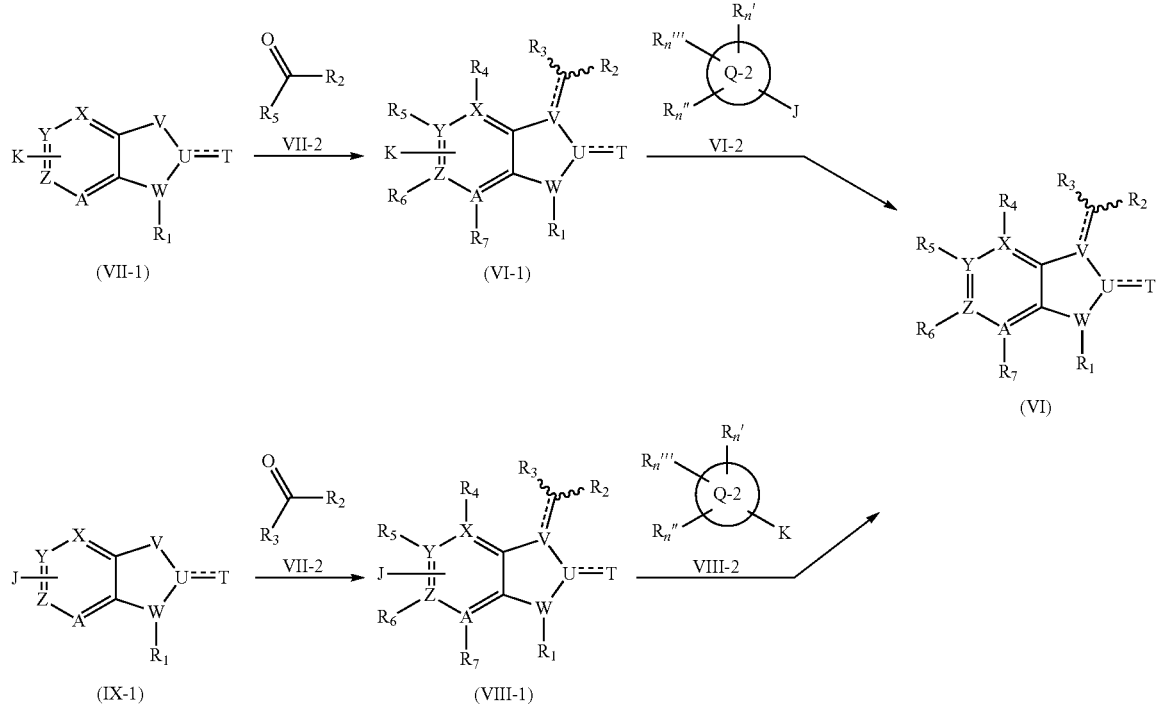

Scheme 1

In the scheme, $R_1$, $R_2$, $R_3$, $R_4$, $R_5$, $R_6$, $R_7$, T, U, V, W, X, Y, Z, A, $R_n'$, $R_n''$, $R_n'''$ and Q-2 are as defined in the above Formula VI, except that in VI-1 and VIII-1, $R_4$, $R_5$, $R_6$, and $R_7$ are not J is metal containing group such as boronic acid, boronic acid pinacol ester, trifluoro boran, organic tin, zinc halide, magnesium halide, organic silicon, and organic lithium. K is leaving group such as Cl, Br, I, and OTf.

Preparation Method I

A compound of the invention may be synthesized using the following method.

Among a compound of Formula VI, Compound VI-3 or a pharmaceutically acceptable salt thereof is prepared by the method as follows:

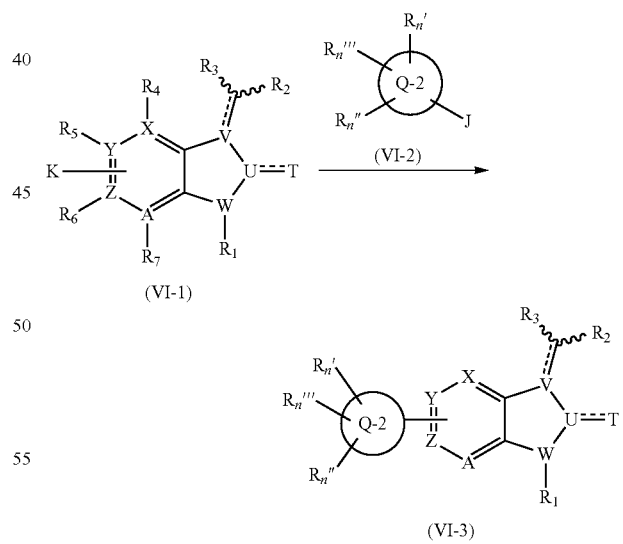

Scheme 2

In the scheme, the symbols have the same meaning as defined above.

A compound of formula VI-1 can react with a compound of formula VI-2 in the presence of transition metal catalyst (representative examples include, but are not limited to tetrakis(triphenylphosphine)palladium(0), [1, 1'-bis(diphenylphosphino)ferrocene] palladium(II) dichloride, palladium carbon, dichlorobis(triphenylphosphine)nickel(II), or bis(triphenylphosphine)palladium(II) dichloride.), alkali metal carbonate (representative examples include, but are not limited to potassium carbonate, sodium carbonate, or cesium carbonate.) or other alkali metal salt (sodium hydroxide, potassium hydroxide, sodium ethoxide, sodium methoxide, sodium tert-butoxide, potassium tert-butoxide, sodium hydride, sodium phosphate, potassium phosphate.) and appropriate solvent or without solvent to give a compound of formula VI-3.

Preparation method II

A compound VI-1 may be prepared from a compound VII-2.

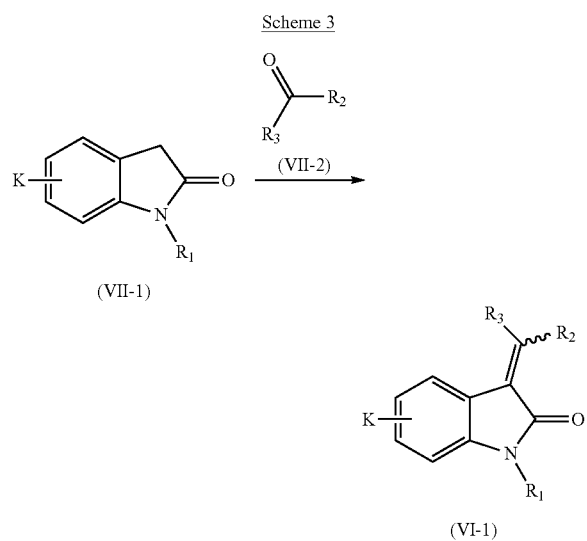

In the scheme, the symbols have the same meaning as defined above.

A compound of formula VII-1 can react with a compound of formula VII-2 in the presence of a base (representative examples include, but are not limited to pyrrolidine and piperidine) or an acid (representative examples include, but are not limited to hydrochloric acid, acetic acid, trifluoroacetic acid), and appropriate solvent or without solvent to give a compound of formula VI-1.

Presently disclosed pharmaceutical compositions can be used in an animal or human. A presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation. The compounds presently disclosed may also be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

The formulations may conveniently be presented in unit dosage form and may be prepared by any methods well known in the art of pharmacy. The amount of active ingredient that can be combined with a carrier material to produce a single dosage form will vary depending upon the mammal being treated and the particular mode of administration. The amount of active ingredient, which can be combined with a carrier material to produce a single dosage form, will generally be that amount of the compound that produces a therapeutic effect. Generally, out of 100%, this amount will range, for example, from about 0.1% to about 25% (e.g., 1%, 2%, 5%, 10%, 15%, 20%) of active ingredient.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the alcohol or inhibitor according to the invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to the alcohols or inhibitors according to the invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more alcohols or inhibitors according to the invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of an alcohol or other inhibitor according to the invention include powders, sprays, ointments, pastes, creams, lotions, gels, solutions, patches and inhalants. The active compound may be mixed under sterile conditions with a pharmaceutically acceptable excipient, carrier, or diluent, including any preservatives, buffers, or propellants which may be required.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dlchlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

The ointments, pastes, creams and gels may contain, in addition to an alcohol or other inhibitor according to the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more alcohols or inhibitors according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the alcohol or inhibitor according to the invention, it is desirable to slow the absorption of the alcohol or inhibitor from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered composition is accomplished by dissolving or suspending the alcohol or inhibitor in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone, or simultaneously, subsequently or sequentially with one or more active agents, other pharmaceutical agents, or with other agents commonly prescribed or used to treat a NAFLD/NASH symptoms or those of its comorbidities, as well as in combination with a pharmaceutically acceptable excipient, carrier, or diluent as described above.

The amount of pharmacological agent in the oral unit dosage form, with as a single or multiple dosage, is an amount that is effective for treating a neurological disorder. As one of skill in the art will recognize, the precise dose to be employed will depend on a variety of factors, examples of which include the condition itself, the seriousness of the condition being treated, the particular composition used, as well as various physical factors related to the individual being treated. In vitro or in vivo assays can optionally be employed to help identify optimal dosage ranges.

A proposed dose of a presently disclosed compound for oral, parenteral or buccal administration to the average adult human for the treatment or prevention of a disease state herein relevant is about 0.1 mg to about 2000 mg. In certain embodiments, the proposed dose is from about 0.1 mg to about 200 mg (e.g., 1 mg, 5 mg, 10 mg, 20 mg, 50 mg, 75 mg, 100 mg, 150 mg) of the active ingredient per unit dose. Irrespective of the amount of the proposed dose, administration of the compound can occur, for example, 1, 2, 3, or 4 times per day, or 1, 2, 3, 4 or 5 times a week.

Aerosol formulations for the treatment or prevention of the conditions referred to herein the average adult human are preferably arranged so that each metered dose or "puff" of aerosol contains about 20 µg to about 10,000 µg, preferably, about 20 µg to about 1000 µg (e.g., 25 µg, 50 µg, 100 µg, 200 µg, 500 µg, 750 µg) of a presently disclosed compound. The overall daily dose with an aerosol will be within the range from about 100 µg to about 100 mg (e.g., 200 µg, 500 µg, 1 mg, 2 mg, 5 mg, 10 mg, 25 mg, 50 mg, 75 mg). In certain embodiments, the overall daily dose with an aerosol generally will be within the range from about 100 µg to about 10 mg (e.g., 200 µg, 500 µg, 1 mg, 2 mg, 5 mg, 7.5 mg). Administration may be several times daily, for example 1, 2, 3, 4, 5 or 8 times, giving for example, 1, 2 or 3 doses each time.

The compounds of the present invention can be prepared using the methods described in present invention, together with synthetic methods known to one skilled in the art of organic synthesis, medicinal chemistry and related fields, or variations thereon. The reactions are performed in solvents where appropriate to the reagents and materials employed and are suitable for transformations being effected. The starting materials for the examples contained herein are either commercially available or are readily prepared by standard methods from known materials. For example, the following reactions are illustrations but not limitations of the preparation of some of the starting materials and examples used herein.

EXAMPLES

Synthesis Examples

Preparation of Compound 7-1

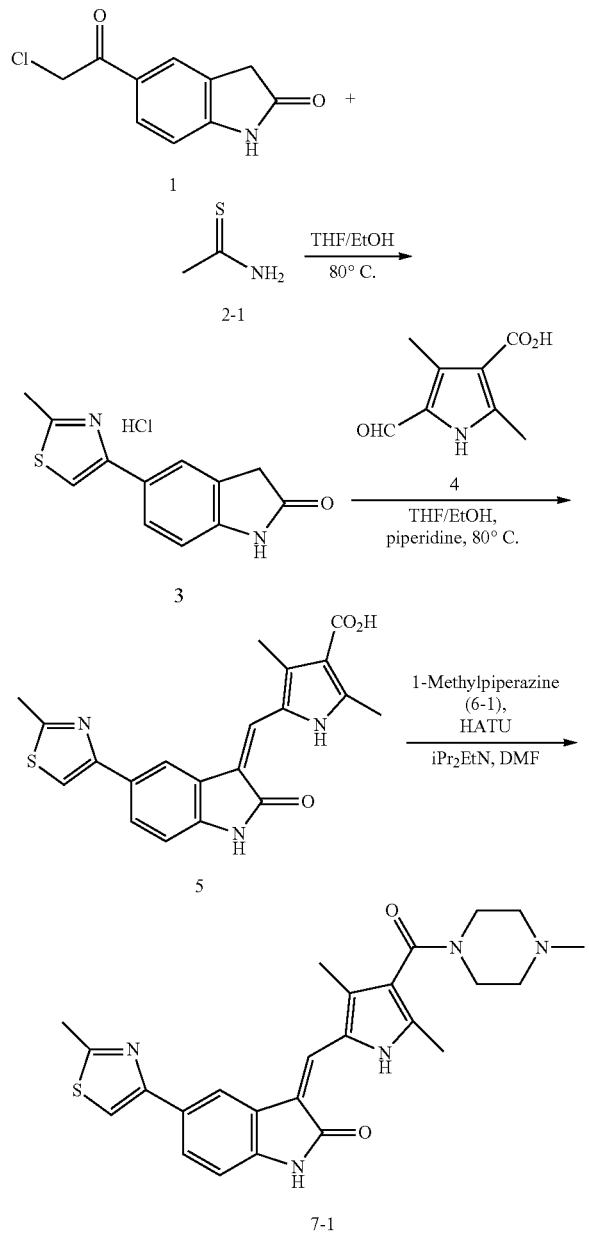

To a suspension of 5-chloroacetyloxindole 1 (42 mg, 0.2 mmol) in EtOH/THF (2 mL/1 mL) was added thioacetamide 2-1 (15 mg, 0.2 mmol). The mixture was heated at 80° C. for 16 h before cooled down. The solution was concentrated in vacuo to get an orange solid 3. $^1$H NMR (300 MHz, DMSO-d6) δ 10.50 (br. S, 1H), 7.72-7.80 (m, 2H), 7.33 (s, 1H), 7.16 (s, 1H), 6.86 (d, 1H, J=8.63 Hz), 3.42-4.54 (m, 2H); MS m/z 231.10 (M+H).

To a solution of 3 (53 mg, 0.2 mmol) in EtOH/THF (2 mL/1 mL) (or use the above reaction mixture in EtOH/THF (2 mL/1 mL) solution) was added 5-formyl-2,4-dimethyl-1H-pyrrole-3-carboxylic acid 4 (33.4 mg, 0.2 mmol) and piperidine (21.8 μL). The mixture was heated at 80° C. for 2 hours. After cooled down to room temperature, the reaction mixture was filtrated and washed with EtOH (1 mL) to get the reddish solid 5. $^1$H NMR (300 MHz, DMSO-d6) δ 13.80 (s, 1H), 12.10 (br.s, 1H), 11.08 (s, 1H), 8.35 (s, 1H), 7.85 (s, 1H), 7.78-7.81 (m, 2H), 6.94 (d, 1H, J=8.11 Hz), 2.74 (s, 3H), 2.56 (s, 3H), 2.52 (s, 3H); MS m/z 380.21 (M+H).

To a solution of 5 (20 mg, 0.052 mmol) in DMF (1.5 mL) was added HATU (24 mg, 0.063 mmol), diisopropylethylamine (30 μL, 0.168 mmol), and 1-methylpiperazine 6-1 (10 μL, 0.090 mmol). The mixture was stirred at room temperature for 16 hours then concentrated in vacuo. The residue was added CH$_2$Cl$_2$ (2 mL) and extracted with H$_2$O (3×1.5 mL). The organic layer was dried over Na$_2$SO$_4$ and concentrated in vacuo. The residue was purified by column chromatography (CH$_2$Cl$_2$/MeOH/Et$_3$N) to get a yellow solid 7-1. $^1$H NMR (300 MHz, DMSO-d6) δ 11.00 (s, 1H), 8.30 (s, 1H), 7.83 (s, 1H), 7.65-7.78 (m, 2H), 6.94 (d, 1H, J=8.18 Hz), 3.02-3.20 (m, 4H), 2.74 (s, 3H), 2.5-2.58 (m, 4H), 2.5 (s, 6H), 2.3 (s, 3H); MS m/z 462.20 (M+H).

Preparation of Compound 10-1

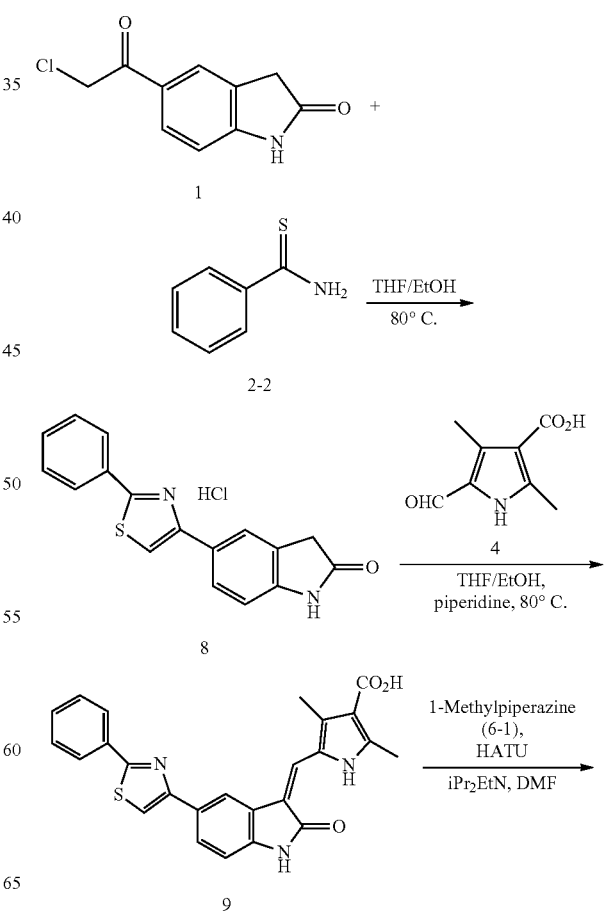

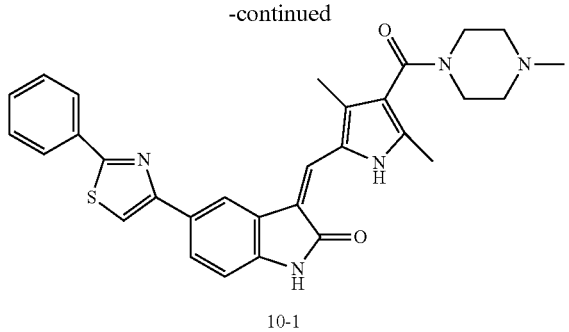

10-1

To a suspension of 5-chloroacetyloxindole 1 (820 mg, 4 mmol) in EtOH/THF (20 mL/20 mL) was added thiobenzamide 2-2 (550 mg, 4 mmol). The mixture was heated at 80° C. for 16 h before cooled down. The solution was concentrated in vacuo to get an orange solid 8. MS m/z 293.20 (M+H).

To this solid 8 was added EtOH/THF (20 mL/20 mL) (or use the above reaction mixture), 5-formyl-2,4-dimethyl-1H-pyrrole-3-carboxylic acid 4 (668 mg, 4 mmol) and piperidine (400 µL). The mixture was heated at 80° C. for 5 hours. After cooled down to room temperature, the reaction mixture was filtrated and washed with EtOH (1 mL) to get the orange solid 9. $^1$H NMR (300 MHz, DMSO-d6) δ 13.80 (s, 1H), 12.40 (s, 1H), 11.10 (s, 1H), 8.47 (s, 1H), 8.07-8.12 (m, 3H), 7.94 (d, 1H, J=8.00 Hz), 7.86 (s, 1H), 7.55-7.6 (m, 3H), 7.01 (d, 1H, J=8.10 Hz), 2.59 (s, 3H), 2.57 (s, 3H); MS m/z 442.20 (M+H).

To a solution of 9 (34 mg, 0.077 mmol) in DMF (1.5 mL) was added HATU (35 mg, 0.092 mmol), diisopropylethylamine (30 µL, 0.168 mmol), and 1-methylpiperazine 6-1 (15 µL, 0.13 mmol). The mixture was stirred at room temperature for 16 hours then concentrated in vacuo. The residue was added CH$_2$Cl$_2$ (2 mL) and extracted with H$_2$O (3×1.5 mL). The organic layer was dried over Na$_2$SO$_4$ and concentrated in vacuo. The residue was purified by column chromatography (CH$_2$Cl$_2$/MeOH/Et$_3$N) to get a yellow solid 10-1. $^1$H NMR (300 MHz, DMSO-d6) δ 13.68 (s, 1H), 11.10 (s, 1H), 8.44 (s, 1H), 8.07-8.10 (m, 3H), 7.91 (d, 1H, J=8.00 Hz), 7.80 (s, 1H), 7.68-7.76 (m, 2H), 7.52-7.58 (m, 1H), 7.01 (d, 1H, J=8.10 Hz), 3.02-3.15 (m, 4H), 2.52-2.58 (m, 4H), 2.5 (s, 3H), 2.35 (s, 3H), 2.33 (s, 3H); MS m/z 524.20 (M+H).

Preparation of Compound 13-3

Scheme 6

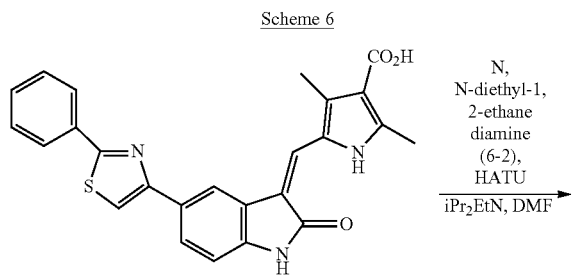

9

N,N-diethyl-1,2-ethane diamine (6-2), HATU
iPr$_2$EtN, DMF
→

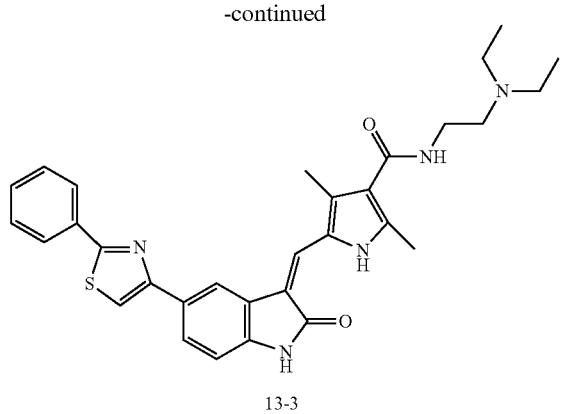

13-3

To a solution of 9 (1.55 g, 3.5 mmol) in DMF (130 mL) was added HATU (1.6 g, 4.2 mmol), diisopropylethylamine (1.6 mL, 9.2 mmol), and N,N-diethyl-1,2-ethanediamine 6-2 (0.6 mL, 4.2 mmol). The mixture was stirred at room temperature for 16 hours then concentrated in vacuo. The residue was added CH$_2$Cl$_2$ (800 mL) and extracted with H$_2$O (200 mL), saturated NaHCO$_3$ (200 mL), H$_2$O (2×200 mL), and brine (200 mL). The organic layer was dried over Na$_2$SO$_4$ and concentrated in vacuo. The residue was added small amount of MeOH and filtration to get a yellow solid 13-3. $^1$H NMR (300 MHz, DMSO-d6) δ 13.70 (s, 1H), 11.10 (s, 1H), 8.44 (s, 1H), 8.07-8.10 (m, 3H), 7.92 (d, 1H, J=8.10 Hz), 7.81 (s, 1H), 7.3-7.6 (m, 3H), 7.00 (d, 1H, J=8.10 Hz), 3.2-3.3 (m, 2H), 2.5-2.6 (m, 6H), 2.51 (s, 3H), 2.48 (s, 3H), 1.00 (t, 6H, J=6.90 Hz); MS m/z 540.20 (M+H).

Preparation of Compound 18-5

Scheme 7

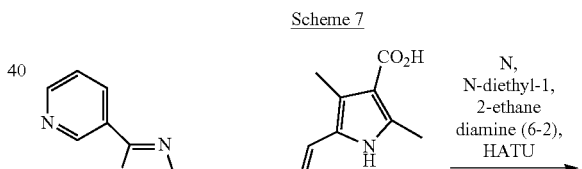

12

N,N-diethyl-1,2-ethane diamine (6-2), HATU
iPr$_2$EtN·DMF
→

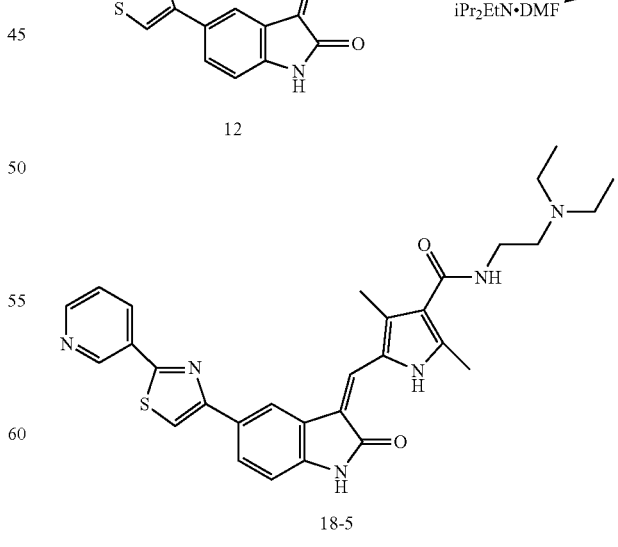

18-5

To a solution of the solid 12 (44 mg, 0.10 mmol) in DMF (1.5 mL) was added HATU (35 mg, 0.12 mmol), diisopropylethylamine (50 μL, 0.33 mmol), and N,N-diethyl-1,2-ethanediamine 6-2 (23 μL, 0.2 mmol). The mixture was stirred at room temperature for 16 hours then concentrated in vacuo. The residue was added CH$_2$Cl$_2$ (2 mL) and extracted with H$_2$O (1.5 mL). The organic layer was dried over Na$_2$SO$_4$ and concentrated in vacuo. The residue was purified by column chromatography (CH$_2$Cl$_2$/MeOH/Et$_3$N) to get a yellow solid 18-5. $^1$H NMR (400 MHz, DMSO-d6) δ 13.60 (s, 1H), 11.00 (s, 1H), 9.18 (d, 1H, J=1.60 Hz), 8.64 (dd, 1H, J=4.80, 1.60 Hz), 8.33-8.37 (m, 2H), 8.09 (s, 1H), 7.83 (dd, 1H, J=8.00, 1.60 Hz), 7.71 (s, 1H), 7.50 (dd, J=8.00, 4.80 Hz, 1H), 7.36-7.39 (m, 1H), 6.91 (d, 1H, J=8.00 Hz), 3.20 (q, J=7.10 Hz, 4H), 2.4-2.6 (m, 4H), 0.90 (t, J=7.10 Hz, 6H); MS m/z 525.20 (M+H). MS m/z 541.20 (M+H).

Compound 18-5 can be prepared from compound 12 and N,N-diethyl-1,2-ethanediamine 6-2 using a method analogous to that used for the preparation of compound 18-2 shown in the next example.

Preparation of Compound 18-2

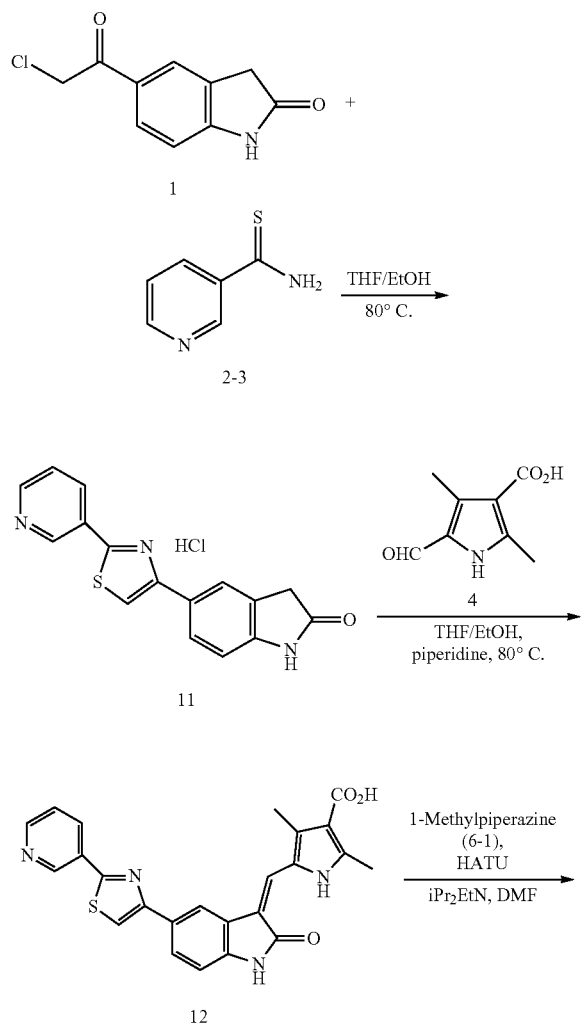

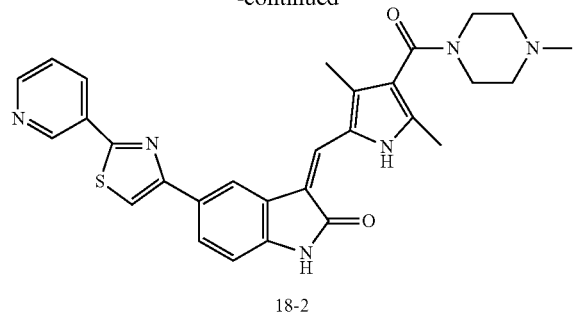

18-2

To a suspension of 5-chloroacetyloxindole 1 (42 mg, 0.2 mmol) in EtOH/THF (1 mL/1 mL) was added thionicotinamide 2-3 (27.8 mg, 0.2 mmol). The mixture was heated at 80° C. for 16 h before cooled down. The solution was concentrated in vacuo to get an orange solid 11. MS m/z 294.20 (M+H).

To this solid 11 was added EtOH/THF (1 mL/1 mL), 5-formyl-2,4-dimethyl-1H-pyrrole-3-carboxylic acid (33.4 mg, 0.2 mmol) and piperidine (21.8 μL). The mixture was heated at 80° C. for 2 hours. After cooled down to room temperature, the reaction mixture was concentrated and filtrated to get the orange solid 12. MS m/z 443.20 (M+H).

To a solution of the solid 12 (44 mg, 0.10 mmol) in DMF (1.5 mL) was added HATU (35 mg, 0.12 mmol), diisopropylethylamine (50 μL, 0.33 mmol), and 1-methylpiperazine 6-1 (30 μL, 0.26 mmol). The mixture was stirred at room temperature for 16 hours then concentrated in vacuo. The residue was added CH$_2$Cl$_2$ (2 mL) and extracted with H$_2$O (1.5 mL). The organic layer was dried over Na$_2$SO$_4$ and concentrated in vacuo. The residue was purified by column chromatography (CH$_2$Cl$_2$MeOH/Et$_3$N) to get a yellow solid 18-2. $^1$H NMR (400 MHz, DMSO-d6) δ 13.55 (s, 1H), 11.00 (s, 1H), 9.20 (d, 1H, J=1.60 Hz), 8.64 (dd, 1H, J=4.70, 1.60 Hz), 8.35-8.37 (m, 2H), 8.10 (s, 1H), 7.84 (dd, 1H, J=8.00, 1.60 Hz), 7.71 (s, 1H), 7.52 (ddd, J=8.00, 4.70, 0.70 Hz, 1H), 6.92 (d, 1H, J=8.00 Hz), 3.07-3.2 (m, 4H), 2.26 (s, 3H), 2.24 (s, 3H), 2.24-2.3 (m, 4H), 2.13 (s, 3H); MS m/z 525.20 (M+H).

Biomedical Assays

Example 1: Compounds of the Invention Prevent Excess Triglyceride Accumulation in Human Liver Cells Preferred embodiments of the compounds of the invention were evaluated for their ability to inhibit fat buildup, here in cell culture, in order to see if they can be used in treatment of non-alcoholic fatty liver disease (NAFLD) including its more extreme form NASH.

A series of in vitro experiments were first carried out with various human hepatocyte cultures. For example, human HepG2 liver cells were incubated with 1.6 mM palmitoleic acid in EMEM medium for 48 hours in the presence of 0.1 μM Compound 13-3 or control vehicle, DMSO. After 48 hours, cells were collected and the intracellular triglyceride content was measured by a biochemical kit (Biovision, Mountain View, Calif.) as described in Derdak et al. *J Hepatol.* 2013; 58(4):785-91. As shown in the figure (FIG. 1A), the palmitoleic acid treatment substantially increased the intracellular triglyceride content in the HepG2 cells, yet this event was markedly suppressed by Compound 13-3, showing a strong inhibitory effect on fat accumulation in human liver cells.

The effects on triglyceride accumulation from Compound 13-3-1, Compound 13-3-2, Compound 13-3-3, Compound 13-3-5, Compound 13-3-6, Compound 13-3-7, Compound 18-2, Compound 13-3-10 and Compound 13-3-11, as exemplary compounds of the invention, were tested. Human HepG2 liver cells were incubated with 0.8 mM palmitoleic acid in EMEM medium for 24 hours in the presence of 0.1 µM compounds of the invention or control vehicle, DMSO. Subsequently, the cells were washed with PBS and the intracellular fat content was measured by AdipoRed/Hoechst 33258 double staining, which was assessed by flourometry. As shown in the figure (FIG. 1B), the palmitoleic acid treatment substantially increased the intracellular triglyceride content in the HepG2 cells, yet this event was markedly suppressed by each of the nine compounds respectively, showing a comparable or greater inhibitory effect on fat accumulation in human liver cells as compared to Compound 13-3.

Figure 1C:
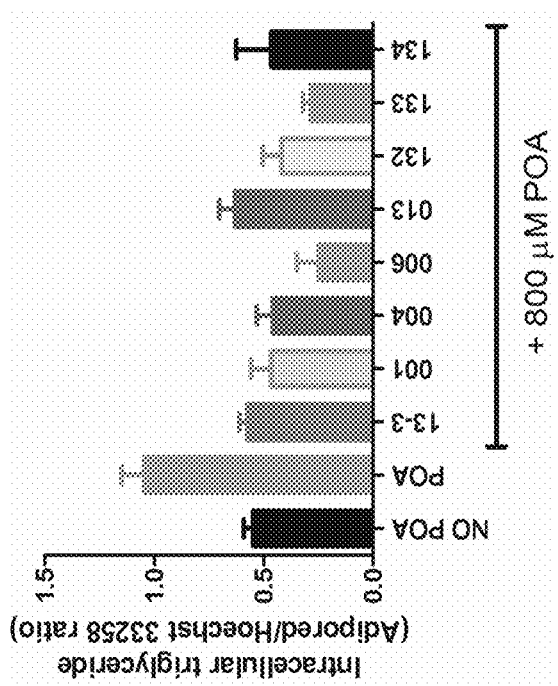

And the effects of Compound 001, Compound 004, Compound 006, Compound 013, Compound 132, Compound 133 and Compound 134, as further exemplary compounds of the invention, were also tested. Human HepG2 liver cells were incubated with 0.8 mM palmitoleic acid in EMEM medium for 48 hours in the presence of 0.1 µM compounds of the invention or control vehicle, DMSO. Subsequently, the cells were washed with PBS and the intracellular fat content was measured by AdipoRed/Hoechst 33258 double staining, which was assessed by flourometry. As shown in the figure (FIG. 1C), the palmitoleic acid treatment substantially increased the intracellular triglyceride content in the HepG2 cells, yet this event was markedly suppressed by the seven deuterides respectively, showing a comparable or greater inhibitory effect on fat accumulation in human liver cells as compared to Compound 13-3.

This observation led to a hypothesis that compounds of the invention may have an intrinsic hepatotropic effect; by directly affecting hepatic fatty acid metabolism, it may alleviate hepatic steatosis and subsequent liver injury in a murine model of NAFLD. To test this hypothesis, the therapeutic efficacy of Compound 13-3 in a high-fat diet (HFD)-induced NAFLD model was assessed.

Example 2: Compound 13-3 Treatment Decreases Body Weight Gain in HFD-Fed Mice without Curbing Daily Caloric or Water Intake, and Markedly Improves NAFLD Symptoms in a Mouse Model In order to assess the in vivo efficacy of Compound 13-3 in improving obesity, and ameliorating NAFLD/NASH, a previously used modified high-fat diet (HFD) was employed to induce obesity and severe fatty liver disease in mice (Derdak et al. *Journal of Hepatology* 2013; 58(4):785-91).

Five-week-old male, C57Bl/6J mice (12-18 per group, Jackson Laboratory, Bar Harbor, Me.) were fed ad libitum with a modified high fat or control diet (Bioserv, Frenchtown, N.J.) for 15 weeks. The calorie profile of the modified HFD (60% of calories from fat) resembled the composition of a previously published diet that effectively induced obesity, steatosis and insulin resistance in this mouse strain (Cong et al. *Life Sci* 2008; 82:983-990). We had verified the efficacy of this diet to induce obesity and NAFLD in various pilot studies. At the end of the 15-week long feeding regimen, this diet caused substantial ALT elevation—indicative of liver injury—in these mice.

After 15 weeks on the modified HFD, the mice were put on a Compound 13-3 (or control vehicle) dosing regimen, in which the introductory 5 mg/kg (p.o., t.i.w. for the first 3 weeks) dose was followed by the administration of 10 mg/kg (p.o., t.i.w. for additional 5 weeks) therapeutic dose. During the course of the drug treatment, the animals were monitored daily for changes in body weight, food/water intake, and adverse effects.

Figures 2A, 2B:
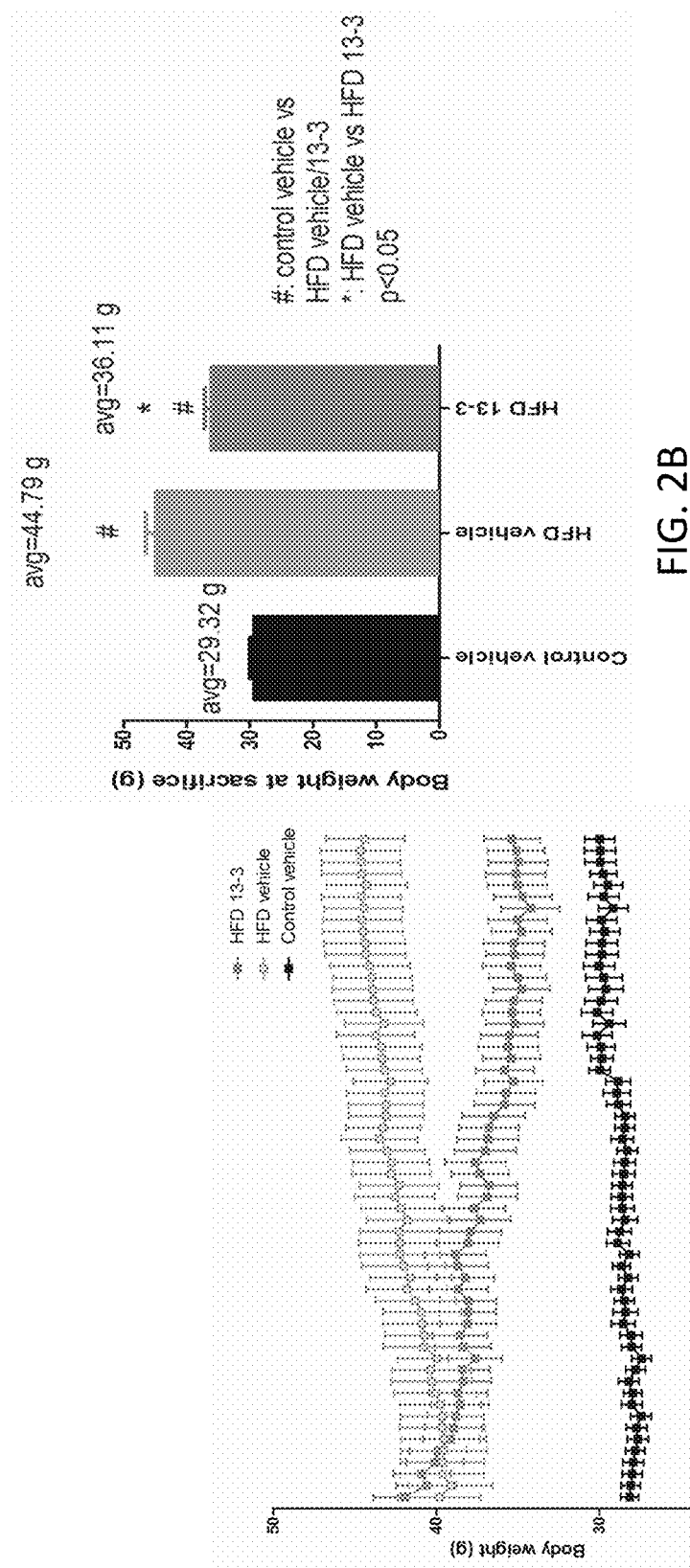
FIGS. 2A-2E present in vivo animal data on: (2A) change in body weight during Compound 13-3 treatment; (2B) body weight at the time of euthanasia; and that Compound 13-3-induced weight loss in HFD-fed (High Fat Diet-fed) mice was not linked to decreased food intake (2C) or water intake (2D); and (2E) macroscopic overview of the liver at the time of euthanasia with or without Compound 13-3 treatment.
Figures 2C, 2D:
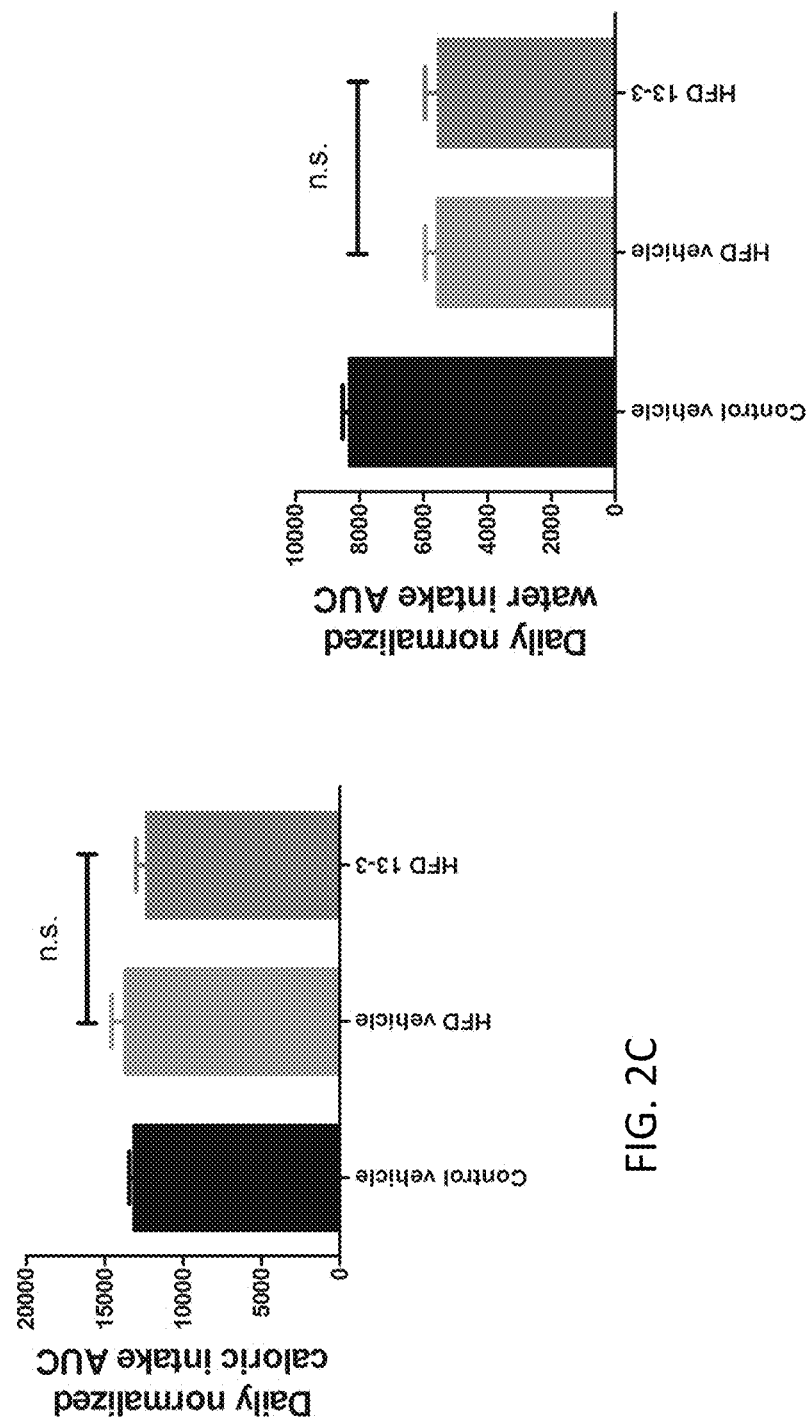

As shown in FIG. 2A, the Compound 13-3 treatment not only prevented additional weight gain in the mice on HFD, but also triggered a gradual weight loss. As FIG. 2B demonstrates, there was a marked, about-20% difference in body weight between the Compound 13-3-treated and control-vehicle-treated mice on HFD at the time of euthanasia. Moreover, the Compound 13-3-induced weight loss in HFD-fed mice was not linked to decreased food intake or water intake (FIGS. 2C & 2D), indicating that a pharmaceutical composition comporising the compound of the invention should generally be very safe with little negative side effect.

Figure 2E:
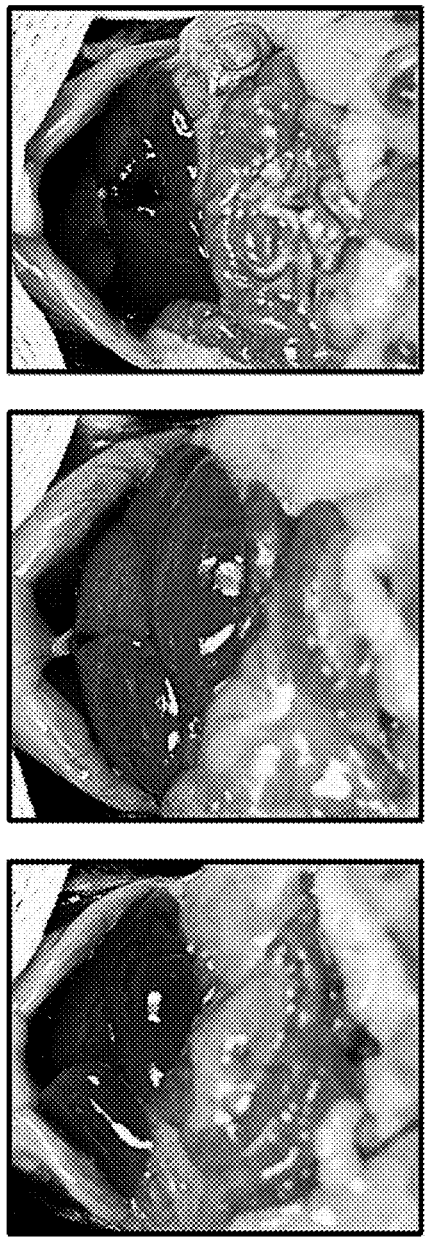

More importantly, the Compound 13-3 treatment markedly improved NAFLD/NASH symptoms, as macroscopic overview of the livers of treated animal indicated at the time of euthanasia (FIG. 2E). The high-fat feeding in the vehicle-treated mice promoted liver enlargement due to ectopic fat accumulation in this organ. The enlarged liver appeared pale yellow consistent with fatty metamorphosis. In sharp contrast, Compound 13-3 markedly decreased the size of the liver in the HFD-fed mice and helped to maintain a healthier, darker brown appearance (far right panel). The beneficial effect on liver size and appearance is consistent with the hypothesized anti-NAFLD/NASH effect of Compound 13-3, an exemplary compound of the invention.

Example 3: Compound 13-3 Treatment Decreases Hepatic Steatosis in HFD-Fed Mice

In agreement with intrinsic hepatotropic effect of Compound 13-3 indicated by the above test examples, dramatic changes in the liver of Compound 13-3-treated HFD-fed mice were observed at the time of euthanasia.

Figure 3A:
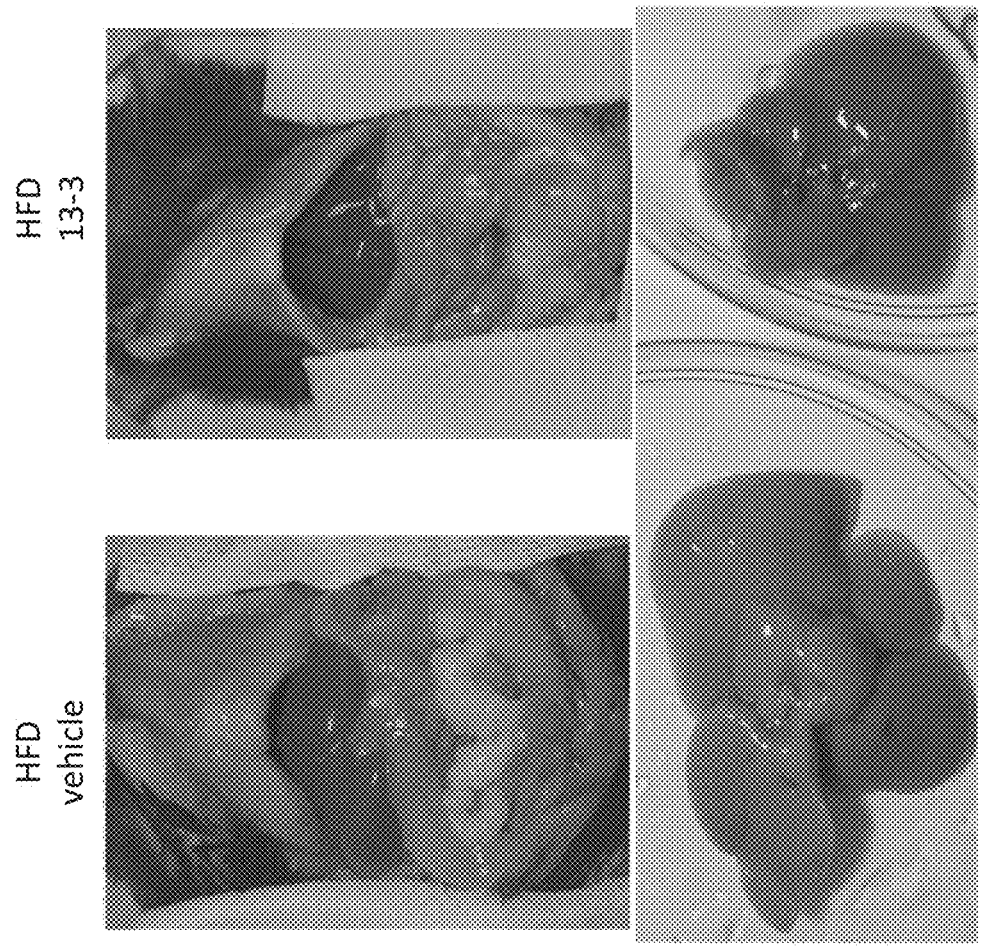

HFD feeding in the vehicle-treated mice promoted liver enlargement due to ectopic fat accumulation in this organ. FIG. 3A provides the macroscopic observation that Compound 13-3 was able to profoundly decrease liver weight and mitigate fatty metamorphosis in the livers of HFD-fed mice in comparison with their vehicle-treated littermates. This observation was further confirmed by measuring the liver weights (FIG. 3B) and expressing it in proportion to the body weight (FIG. 3C). The size of the liver of Compound 13-3-treated, HFD-fed mice was essentially comparable to the lean animals, indicating that the compound markedly decreased or prevented ectopic fat accumulation, inducing a drastic regression or inhibition of NASH symptoms in HFD-fed mice.

Figure 4:
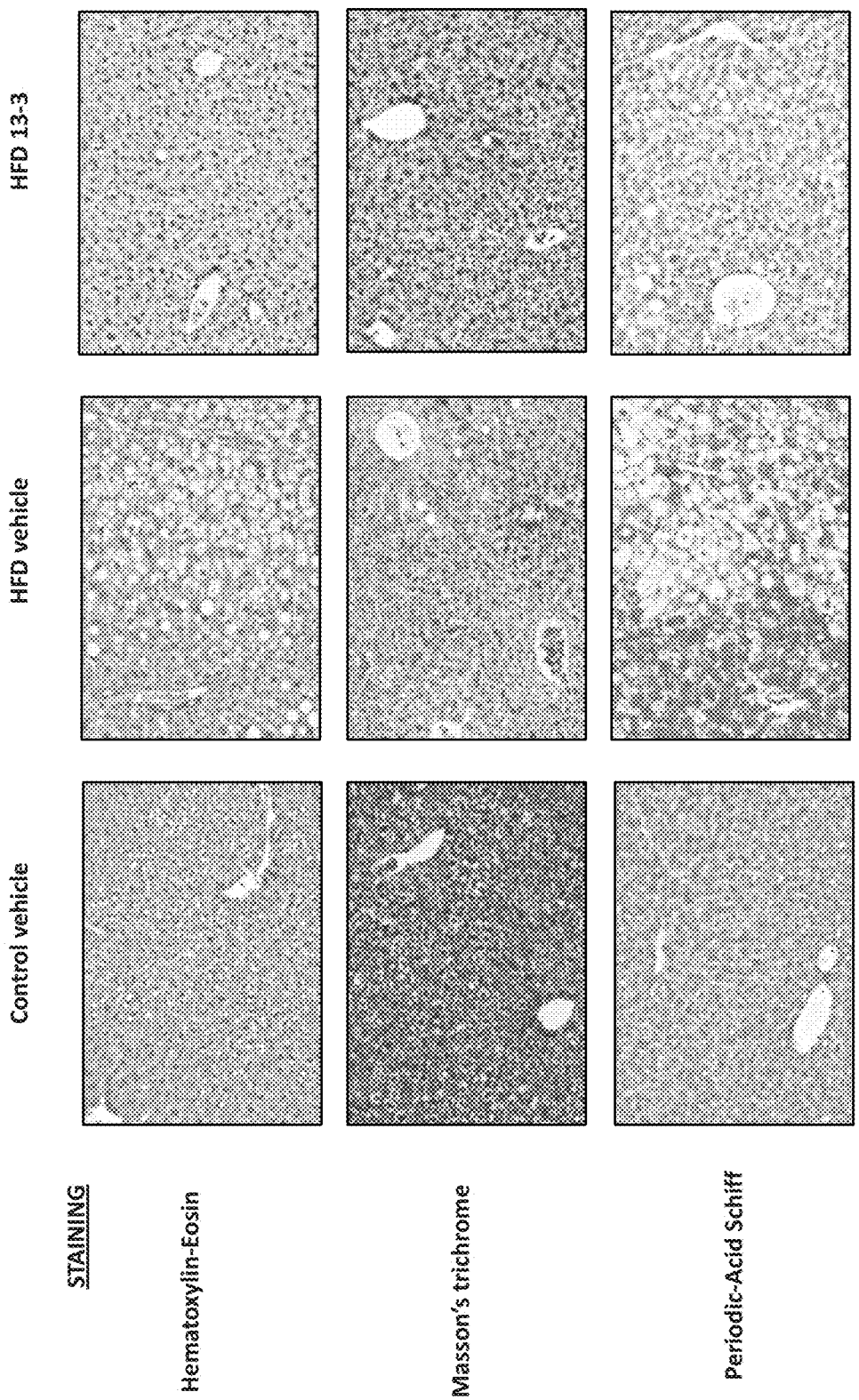
FIG. 4 presents microscopic views of harvested mice liver samples with: (top row) hematoxylin-eosin staining; (middle row) Masson's trichrome staining; (bottom row) Periodic Acid Schiff staining. Left column shows negative control samples; middle column shows HFD-fed and vehicle-treated mice; and right column shows HFD-fed mice treated with Compound 13-3.

Example 4: Compound 13-3 Treatment Decreases Micro- and Macrovesicular Steatosis in HFD-Fed Mice The pronounced efficacy of Compound 13-3 in improving NAFLD was further supported by microscopical analysis of the harvested liver samples (FIG. 4). The hematoxylin-eosin (H&E) staining (top row) revealed a disorganized liver architecture, severe micro- and macrovesicular steatosis with hepatocyte ballooning and inflammation in the livers of HFD-fed vehicle-treated mice in the middle column, all symptoms of NASH. All these pathological changes were markedly suppressed by the Compound 13-3 treatment, as the histological image in the right column was remarkly similar to the negative control in the left column, both showing none of these NASH symptoms.

Additionally, Masson's trichrome staining (middle row) revealed stage 1 fibrosis in the HFD-fed vehicle-treated mice. However, evidence for mild portal and perisinusoidal fibrosis was only found in the HFD-fed vehicle-treated group, while the Compound 13-3-treated HFD-fed mice did not exhibit any signs of fibrosis.

Finally, by using Periodic Acid Schiff (PAS) staining, it was demonstrated that the hepatic glycogen was depleted from zones 2 & 3 and was replaced by fat in the HFD-fed vehicle-treated group, in agreement with the onset of hepatic insulin resistance. In contrast, evidence for hepatic depletion of glycogen was not present in the livers of HFD-fed Compound 13-3-treated mice.

Example 5: Compound 13-3 Markedly Decreases the NAFLD Activity Score (NAS) and Collagen Production In this Example, the effect of Compound 13-3 on the liver was further investigated.

Figure 5A:
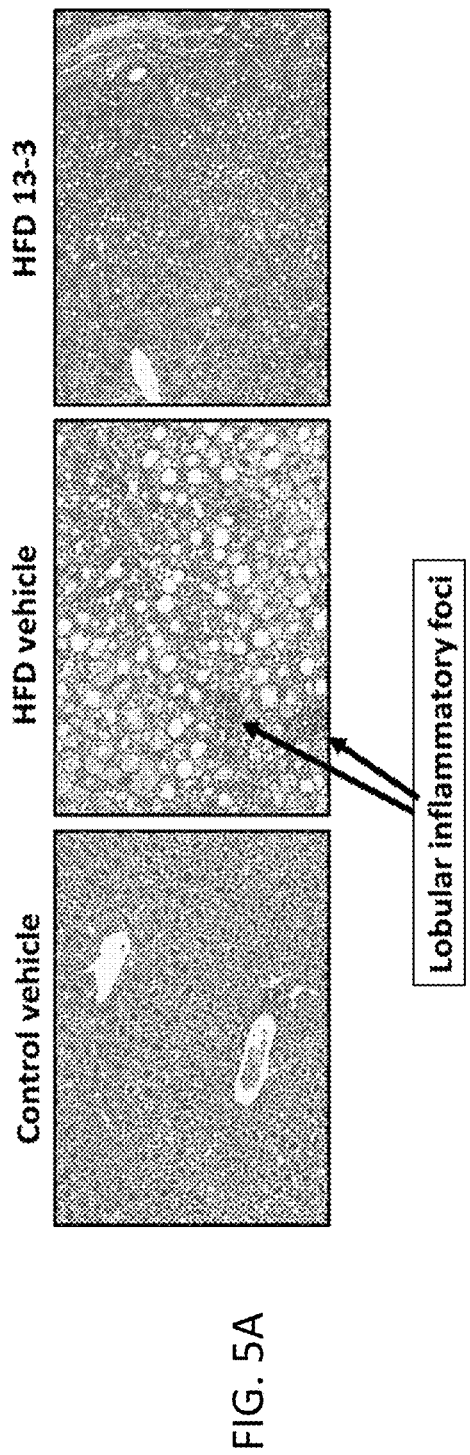
FIGS. 5A-5D present in vivo animal data on: (5A) HFD-induced steatosis and lobular inflammation being suppressed by a compound of the invention, Compound 13-3; (5B) HFD-induced hepatocellular ballooning being eliminated by Compound 13-3; (5C) NAS score being lowered by Compound 13-3; and (5D) collage type I, alpha 1 gene expression being inhibited in the liver by Compound 13-3.
Figure 5B:
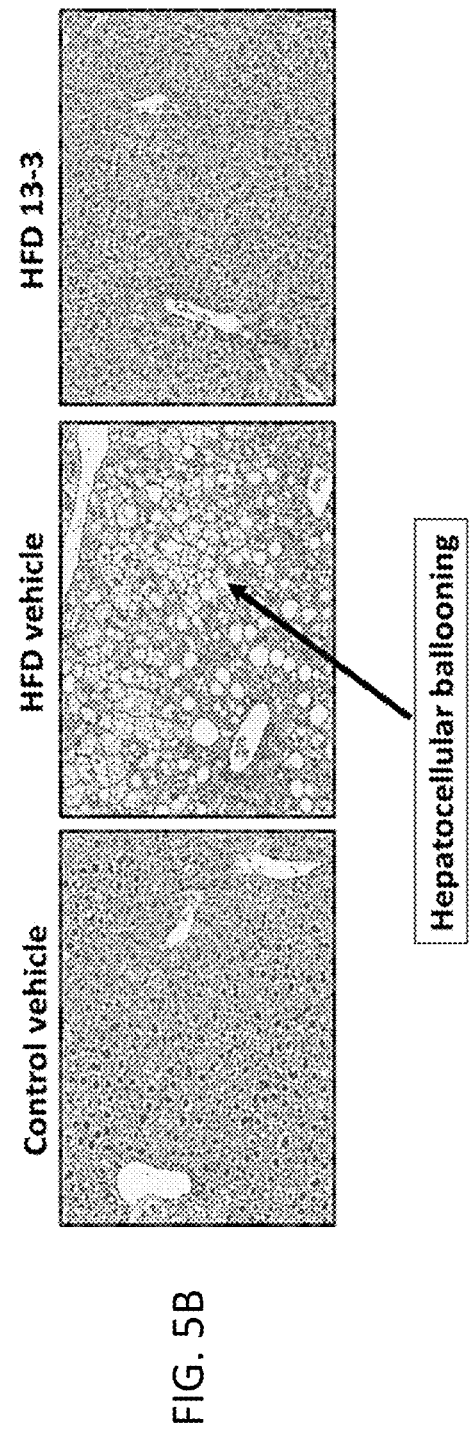

Microscopic evaluation of hematoxylin-eosin (H&E) stained liver slides was performed by an expert pathologist to determine the effect of the drug treatment on the NAFLD Activity Score (NAS), as a primary read-out for the anti-NAFLD efficacy of Compound 13-3. The composite NAS score is frequently used to describe the severity of the characteristic pathological changes seen in NAFLD/NASH (Kleiner D E et al. *Hepatology.* 2005; 41(6):1313-21), including steatosis, lobular inflammation (FIG. 5A), and hepatocellular ballooning (FIG. 5B).

Figure 5C:
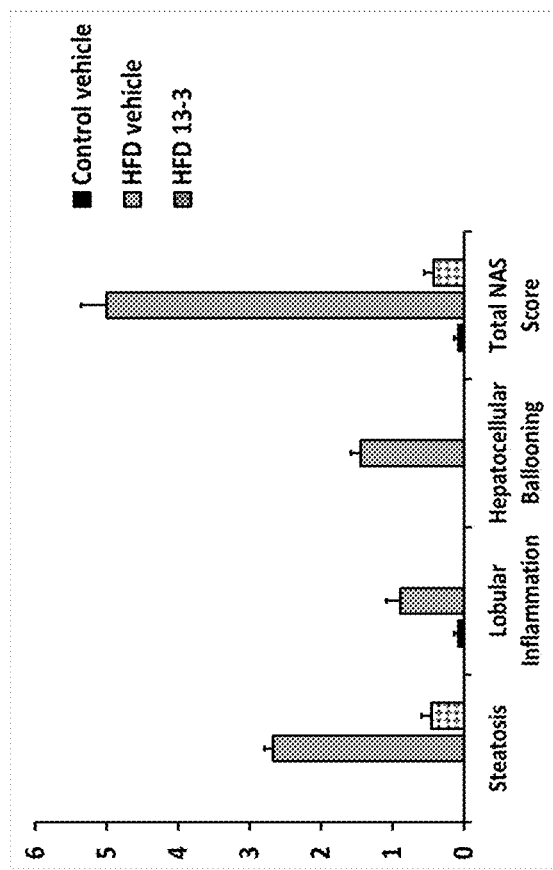
Figure 5D:
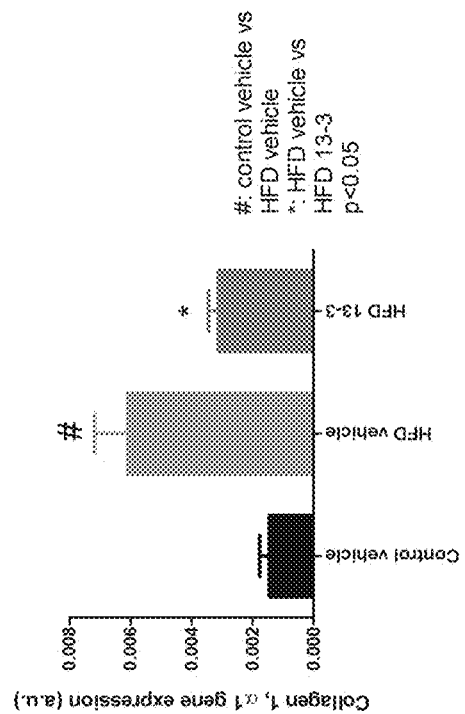

Importantly, the NAS score was substantially lower in the Compound 13-3-treated HFD-fed mice than in their vehicle-treated littermates (FIG. 5C). This drastic improvement in the NAS score was also coupled with a marked decrease in the hepatic production of collagen type I, alpha 1 (FIG. 5D) as measured by quantitative real-time PCT with commercially available probes (Thermo Fisher Scientific Inc., Waltham, Mass.). The inhibition of collagen production in liver indicates that Compound 13-3 may also have anti-fibrotic properties, which is very favorable for purpose of treating or preventing NAFLD/NASH. In conclusion, Compound 13-3 treatment improves every single important aspect of NAFLD/NASH, including steatosis, inflammation, hepatocyte ballooning, and fibrosis. Therefore, pharmaceutical compositions based on Compound 13-3 and other compounds of the invention will likely provide a viable treatment of NAFLD and especially NASH.

Example 6: Compound 13-3 Markedly Reduces the Hepatic Triglyceride Content and Liver Injury The above conclusions of the microscopic findings were also supported by biochemical assays characterizing the hepatic triglyceride content (FIG. 6A) and serum ALT/AST levels (FIGS. 6B-6D).

Figure 6A:
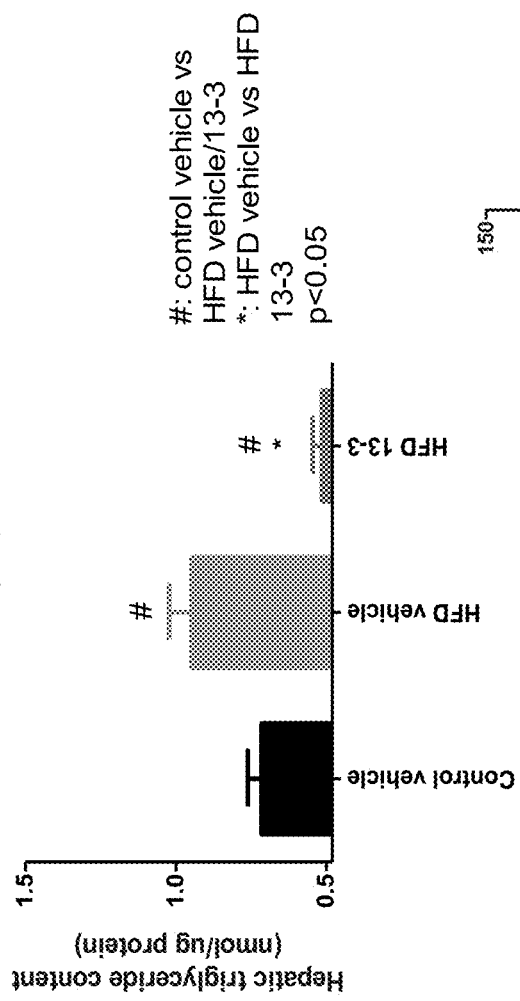
Figure 6B:
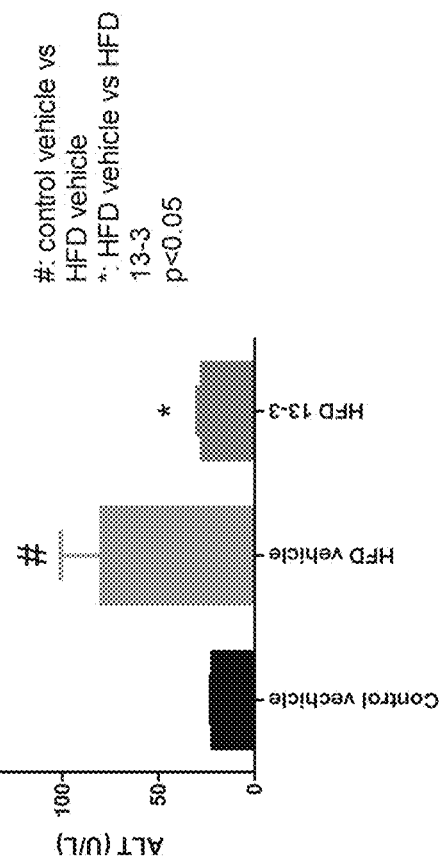

By using a standard biochemical assay to measure hepatic triglyceride (Biovision, Mountain View, Calif.), it was shown that the Compound 13-3 treatment prevented the HFD-induced steatosis (FIG. 6A). This biochemical change is very important, as ectopic fat accumulation has been linked to lipotoxicity and hepatocellular injury. The extent of liver injury has been characterized by measuring serum levels of two liver enzymes ALT (FIG. 6B) and AST (FIG. 6C) (UMASS Mouse Phenotyping Center Analytical Core, Worcester, Mass.) at the time of euthanasia. The observation that in HFD-fed and vehicle-treated mice, the increase in AST levels were not as marked as in the increase in ALT levels indicates that the severity of NAFLD in this animal model might have been modest (FIGS. 6B and 6C). Nonetheless, the fact that Compound 13-3 treatment was able to largely prevent the drastic decrease in the serum AST:ALT ratio in HFD-fed vehicle-treated mice (an indication of ALT elevation brought by HFD feeding) (FIG. 6D), highlights the profound hepatoprotective effect of the compound of the invention.

Figure 7A:
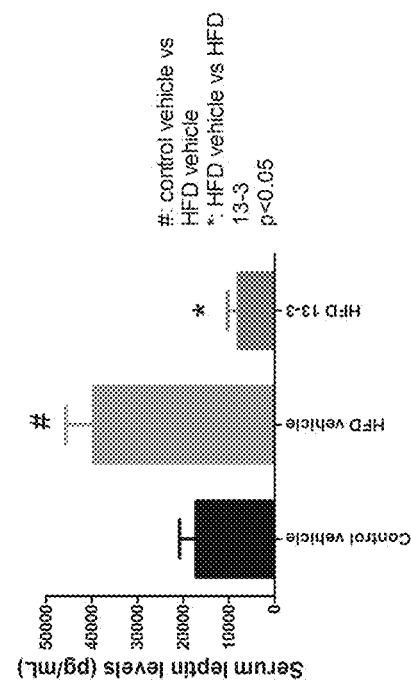
FIGS. 7A-7E present in vivo animal data on: gene expression levels of CPT1a (7A), ACOX1 (7B) and FGF21 (7C); serum FGF21 level (7D) and serum leptin level (7E).
Figure 7B:
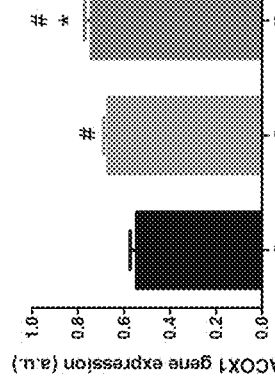
Figure 7C:
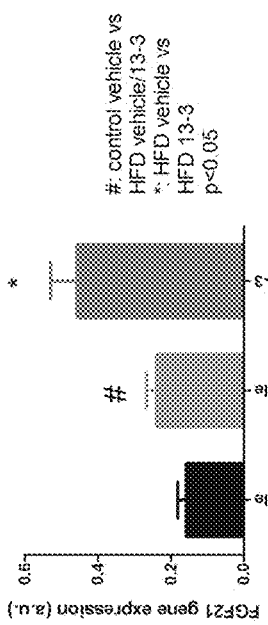
Figure 7D:

Example 7: Compound 13-3 Increases the Expression of Mediators of Fatty Acid Oxidation, and Improves Leptin Resistance in High Fat Diet-Fed Mice To study the effect of Compound 13-3 on the mediators of fatty acid metabolism, we employed quantitative real-time PCR using commercially available probes to assess mediators of fatty acid metabolism in HFD-fed mice treated with Compound 13-3. As shown in FIGS. 7A-7E, gene expression of some key mediators of fatty acid oxidation such as CPT1a (FIG. 7A), an enzyme that catalyzes the rate-limiting step of fatty acid oxidation in the mitochondrion, of peroxisomal ACOX1 (FIG. 7B) and of FGF21 (FIG. 7C), a recently described hepatokine with pronounced anti-NAFLD and hepatoprotective efficacy (see, Maratos-Flier E *Exp Cell Res* (2017) 360(1): 2-5; Sonoda J, et al. *Horm Mol Biol Clin Investig* (2017) 30(2); Xu J, et al. *Diabetes* (2009) 58(1):250-259; Li H, et al. *Diabetes* (2012) 61(4): 797-806; Desai B N, et al. *Mot Metab* (2017) 6(11):1395-1406), were increased by Compound 13-3 treatment in HFD-fed mice. Note especially the pronounced elevation in FGF21 gene expression shown in FIG. 7C. Many of the beneficial metabolic effects are linked to FGF21, and FGF21 itself may further enhance fatty acid oxidation (Xu J, et al. *Diabetes* (2009) 58(1):250-259; Li H, et al. *Diabetes* (2012) 61(4): 797-806). We, therefore, also measured serum levels of FGF21 using a commercially available ELISA kit. We found that treatment of HFD-fed mice with Compound 13-3 increased serum FGF21 levels as well (FIG. 7D). These findings suggest that Compound 13-3 can activate intrinsic mechanisms that promote fatty acid oxidation.

Figure 7E:
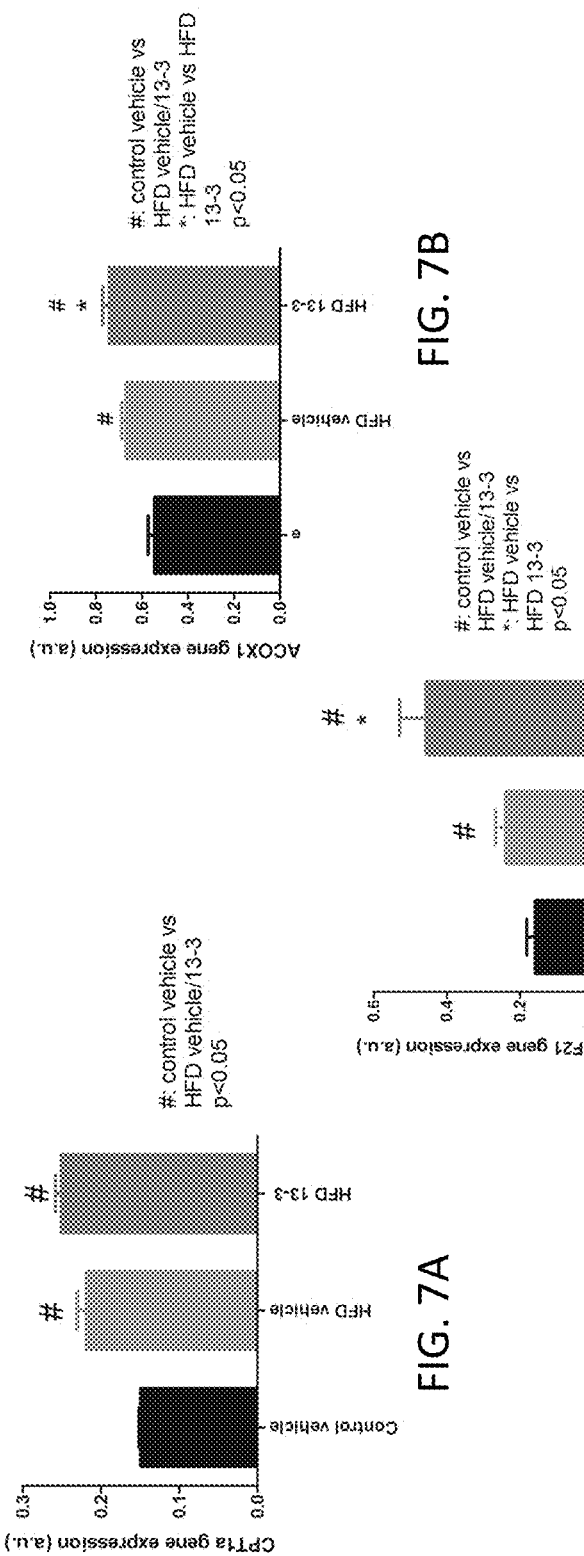

A suppressive effect of exogenous FGF21 on circulating leptin levels has been previously observed in non-human primates. Accordingly, we also measured serum leptin levels using a commercially available ELISA kit. We found that Compound 13-3 significantly decreased HFD-induced increases in leptin levels, indicating improved leptin resistance that results from treatment with a compound of the invention (FIG. 7E).

Example 8: Compound 13-3 Decreases the Expression of Key Adipogenic Targets in the Fatty Livers of High Fat Diet-Fed Mice Our data suggest that Compound 13-3 may increase the expression of PPAR-α downstream targets that are directly involved in fatty acid oxidation (CPT1a, ACOX1) and the expression of FGF21 that can itself further enhance fatty acid oxidation (Xu J, et al. *Diabetes* (2009) 58(1):250-259; Li H, et al. *Diabetes* (2012) 61(4): 797-806). FGF21 has also been linked to the suppression of adipogenesis by suppressing hepatic PPAR-γ, FABP4 and CD36 (Xu J, et al. *Diabetes* (2009) 58(1):250-259). In view of this, we next assessed the expression of these mediators of adipogenesis in the livers of Compound 13-3-treated, HFD-fed mice. We found that Compound 13-3 suppressed the expression of the PPAR-γ gene (FIG. 8A) and protein—the latter was assessed by Western-blotting followed by densitometry (FIG. 8B)—in the liver, and also decreased the gene expression of FABP4 (FIG. 8C), and CD36 (FIG. 8D), indicative of increased FGF21 signaling. These findings suggest that increased fatty acid oxidation and clearance, along with diminished adipogenesis, are key elements of the anti-NAFLD/NASH efficacy of the compound of the invention.

In sum, the compound of the invention, in a representative embodiment as Compound 13-3, is an attractive, novel agent in the treatment of NAFLD including NASH. The compound of the invention exhibits an intrinsic hepatotropic effect that was observed both in human liver cell culture and in a mouse model in vivo. The compound of the invention specifically showed the capacity for promoting fatty acid oxidation and inhibiting de novo fatty acid synthesis. Collectively, these events would lead to decreased hepatic steatosis, inflammation, fibrosis, and liver injury. Therefore, the compound of the invention is an exceedingly strong candidate in the treatment of NAFLD including NASH.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes, to the full extent allowed by the law. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

The invention claimed is:

1. A method for treating nonalcoholic fatty liver disease (NAFLD) in a mammal, comprising administering to a mammalian subject in need thereof:
   (a) a therapeutically effective amount of a pharmaceutical composition comprising a compound of Formula I:

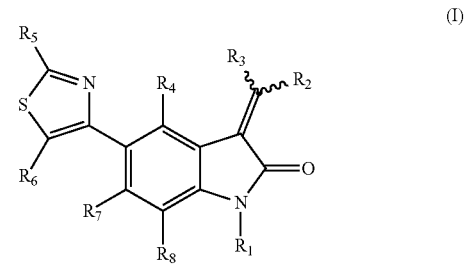

or an enantiomer, diastereomer, tautomer, or pharmaceutically acceptable salt, solvate, ester or pro-drug thereof, and wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_E$, $NR_bBR_c$, $NR_bS(=O)_2R_e$, $NR_b P(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ is hydrogen, halogen, cyano, nitro, $CF_3$, $OCF_3$, alkyl or substituted alkyl, heterocycle or substituted heterocycle, aryl or substituted aryl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and (b) a pharmaceutically acceptable excipient, carrier, or diluent.

2. The method of claim 1, wherein the compound of Formula I is further a compound of Formula II:

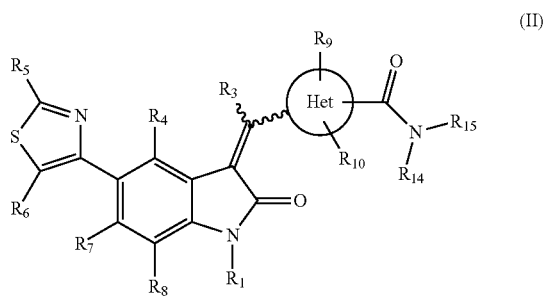

or an enantiomer, diastereomer, tautomer, or pharmaceutically acceptable salt, solvate, ester or pro-drug thereof, and wherein the symbols have the following meanings and are, for each occurrence, independently selected:

Het is a 5- or 6-membered aromatic ring containing at least one heteroatom selected from N, O and S;

$R_3$ and $R_{10}$ are each independently hydrogen, alkyl or substituted alkyl, cycloalkyl or substituted cycloalkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$; and $R_{14}$ and R15 are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle.

3. The method of claim 2, wherein the compound of Formula II is further a compound of Formula III:

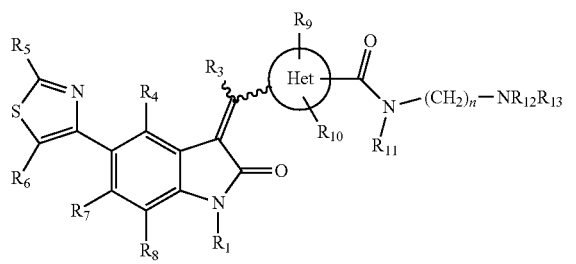

or an enantiomer, diastereomer, tautomer, or pharmaceutically acceptable salt, solvate, ester or pro-drug thereof, and wherein the symbols have the following meanings and are, for each occurrence, independently selected:

$R_{11}$ is hydrogen or $C_{1-4}$ alkyl;

$R_{12}$ and $R_{13}$ are independently hydrogen, alkyl or substituted alkyl, cycloalkyl or substituted cycloalkyl, heterocycle or substituted heterocycle, or aryl or substituted aryl, or said $R_{12}$ and $R_{13}$ together with the N to which they are bonded optionally form a heterocycle or substituted heterocycle; and n is an integer selected from 2, 3, 4, 5 and 6.

4. The method of claim 2, wherein the compound of Formula II is further a compound of Formula IV:

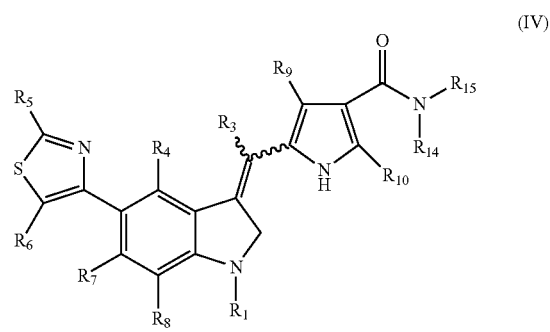

or an enantiomer, diastereomer, tautomer, or pharmaceutically acceptable salt, solvate, ester or pro-drug thereof.

5. The method of claim 3, wherein the compound of Formula III is further a compound of Formula V:

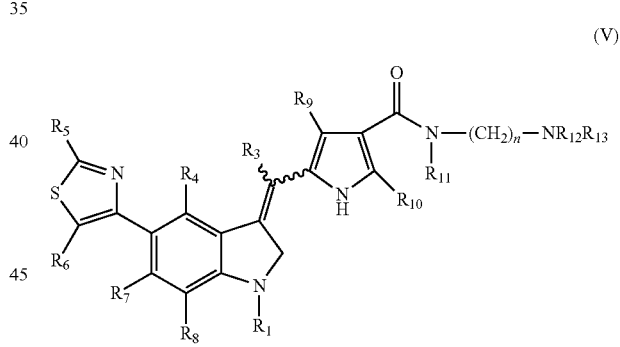

or an enantiomer, diastereomer, tautomer, or pharmaceutically acceptable salt, solvate, ester or pro-drug thereof.

6. The method of claim 1, wherein the NAFLD is non-alcoholic steatohepatitis (NASH).

7. The method of claim 1, wherein the NAFLD is simple steatosis.

8. The method of claim 1, further comprising administering an additional agent selected from the group consisting of: a vitamin, a lipid-lowering medication, an insulin-sensitizing medication, an anti-inflammation medication, a cholesterol-lowering medication, a diabetes medication, an experimental anti-NASH agent, and a weight-loss medication.

9. The method of claim 8, wherein the vitamin is vitamin D or E.

10. The method of claim 8, wherein the anti-inflammation medication is selected from the group consisting of an anti-oxidant medication, anti-apoptotic medication, and anti-cytokine medication.

11. The method of claim 8, wherein experimental anti-NASH agent is selected from the group consisting of farnesoid x receptor agonists, PPAR agonists, Acetyl-CoA carboxylase (ACC), C—C chemokine ligands type 2 and type 5 antagonists, apoptosis signal-regulating kinase (ASK1) inhibitors, lysyl oxidase-like 2 antibody, an anti-hepatofibrotic agent, and galectin-3 inhibitors.

12. The method of claim 1, wherein the mammal is a human.

13. The method of claim 1, wherein the compound of Formula I is selected from the group consisting of:

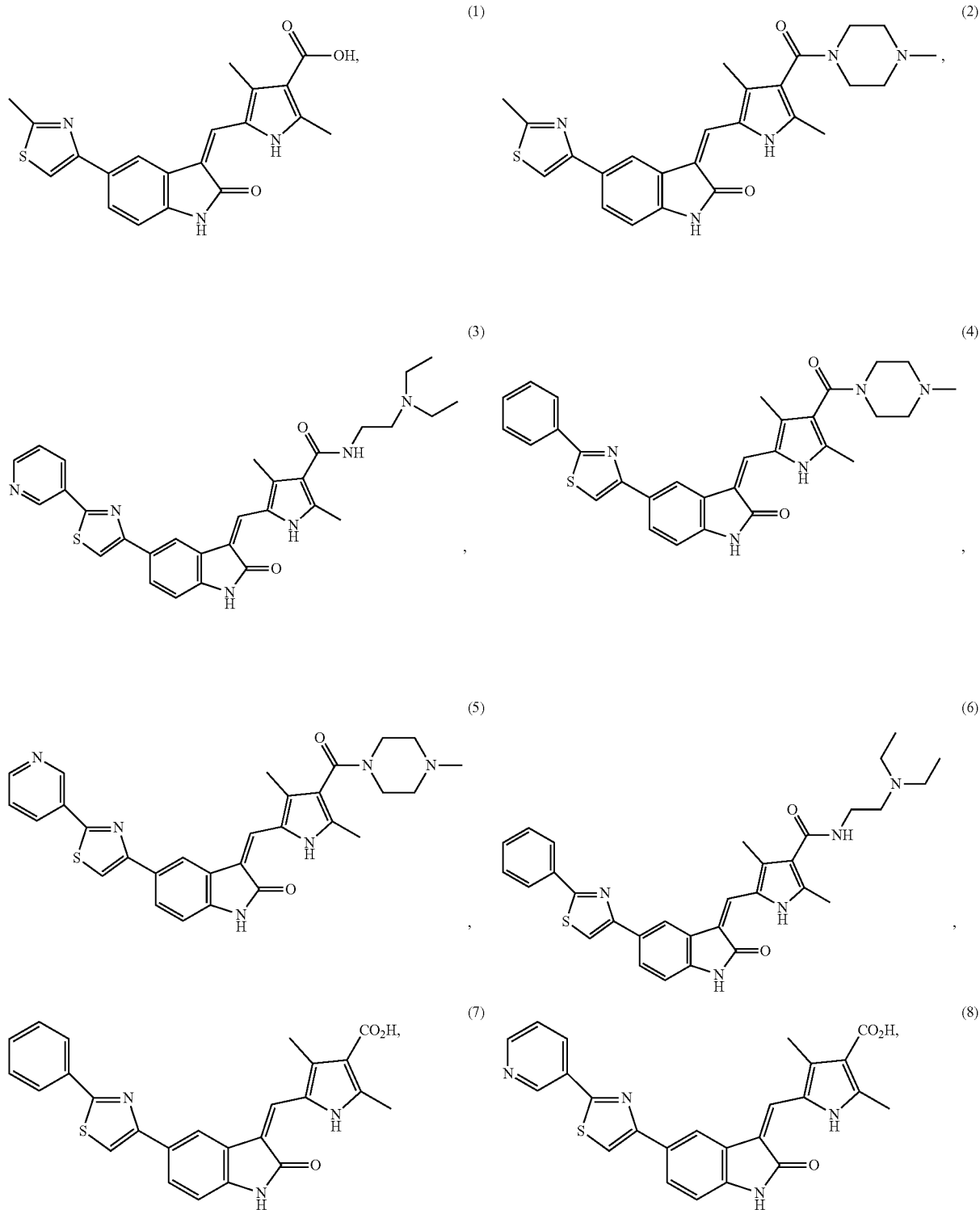

-continued
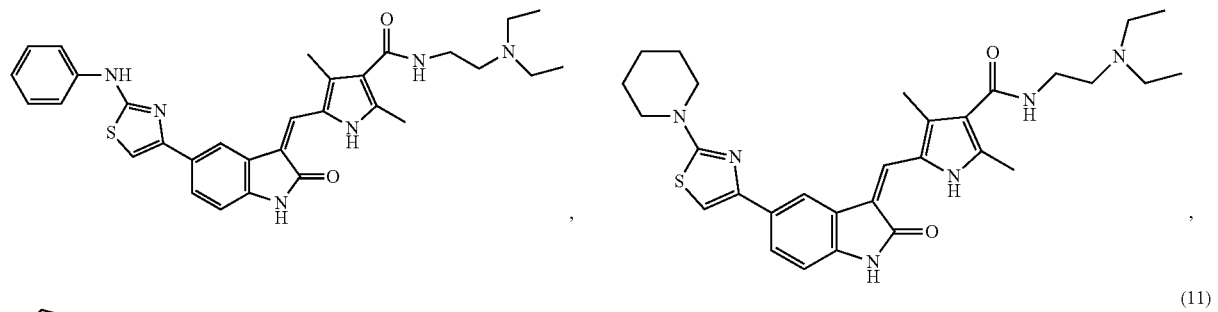
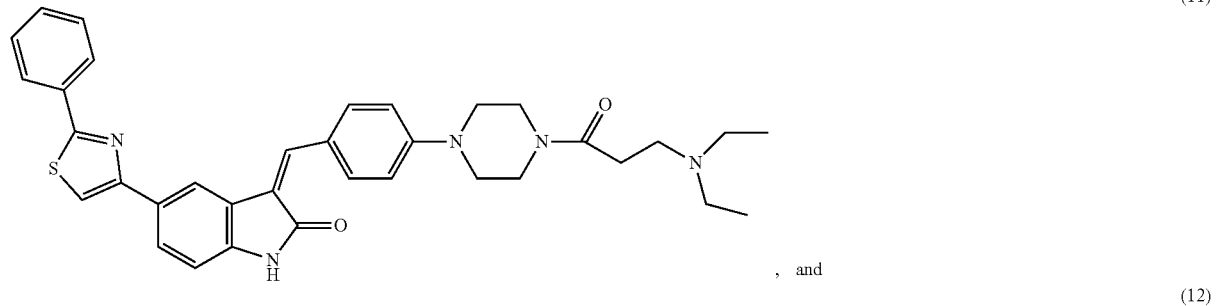
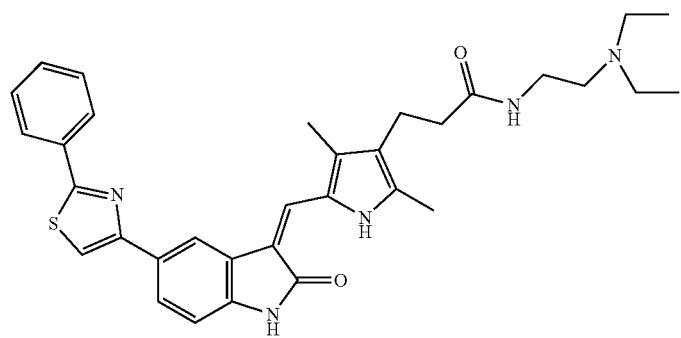
14. The method of claim 1, wherein the compound of Formula I comprises at least one deuterium, and is selected from the group consisting of:
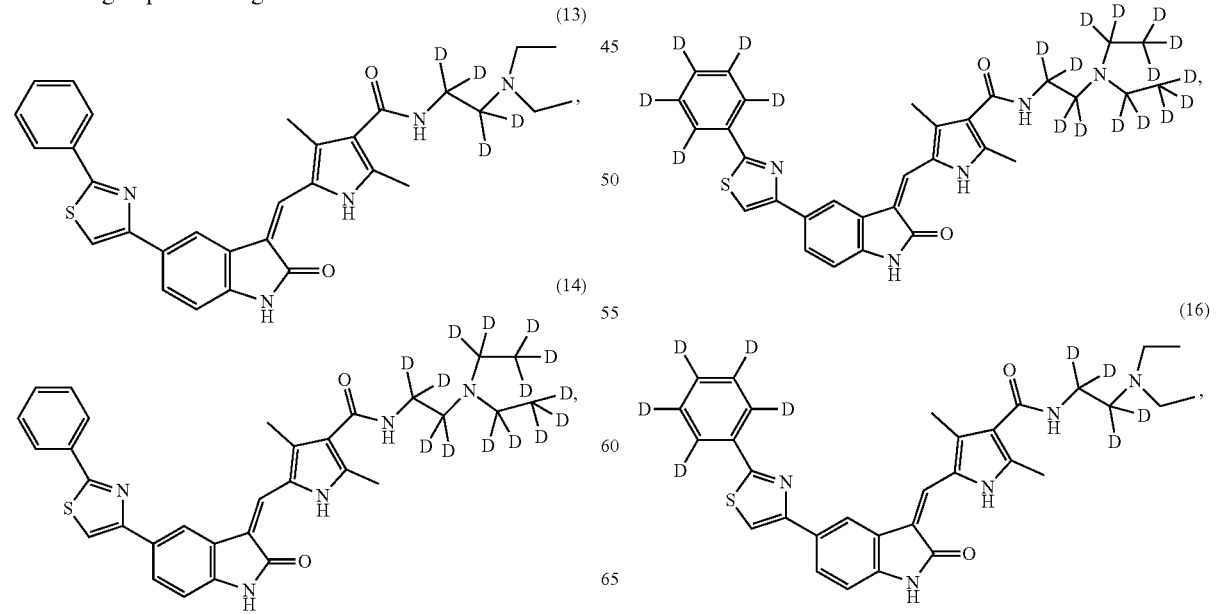

-continued

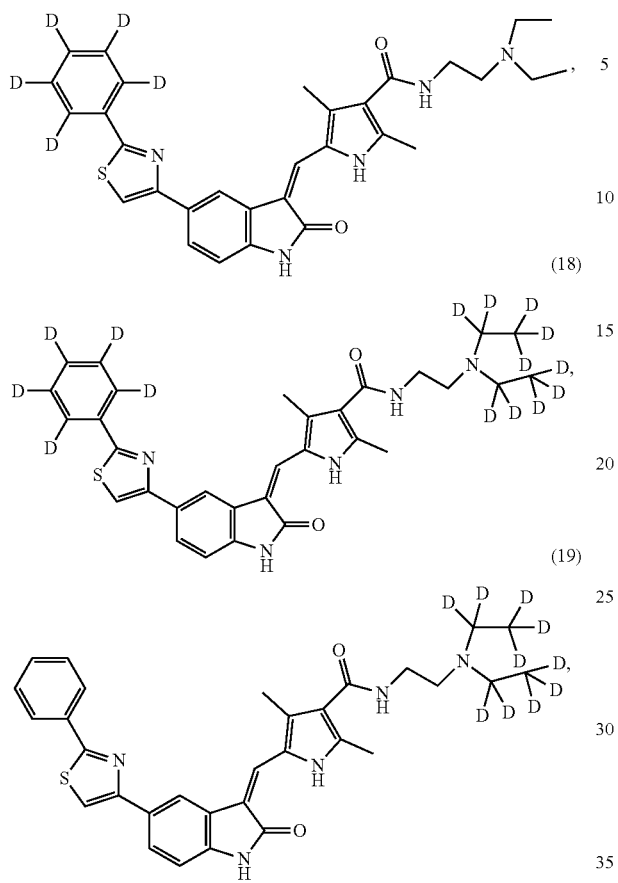

and an enantiomer, diastereomer, tautomer, or pharmaceutically acceptable salt, solvate, ester or pro-drug thereof.

15. A method for reducing or ameliorating a symptom or indication known to be associated with nonalcoholic fatty liver disease (NAFLD) in a mammal, wherein the symptom or indication known to be associated with NAFLD is selected from the group consisting of: accumulation of liver fat, elevated level of hepatic triglyceride, hepatic fibrosis, hepatocyte ballooning, elevated levels of liver enzymes aspartate aminotransferase (AST) and/or alanine aminotransferase (ALT), and an NAFLD Activity Score (NAS) greater than 3, the method comprising administering to a mammalian subject in need thereof:

a therapeutically effective amount of a pharmaceutical composition comprising a compound of Formula I:

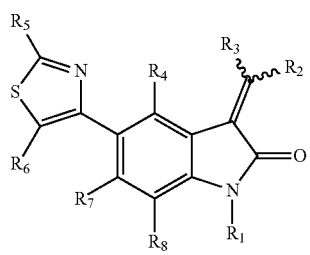

(I)

or an enantiomer, diastereomer, tautomer, or pharmaceutically acceptable salt, solvate, ester or pro-drug thereof, and wherein the symbols have the following meanings and are, for each occurrence, independently selected:

$R_1$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)_2R_e$, $S(=O)_2OR_e$, $C(=O)OR_d$, $C(=O)R_a$, or $C(=O)NR_bR_c$;

$R_2$ is heterocycle or substituted heterocycle, aryl or substituted aryl;

$R_3$ is hydrogen, alkyl or substituted alkyl, cycloalkyl or substituted cycloalkyl, heterocycle or substituted heterocycle, aryl or substituted aryl;

$R_4$, $R_7$, and $R_8$ are each independently hydrogen, halogen, cyano, nitro, $CF_3$, $OCF_3$, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_bP(=O)_2NR_bR_c$, $NR_bC(=O)R_a$, or $NR_bP(=O)_2R_e$;

$R_5$ is alkyl or substituted alkyl, heterocycle or substituted heterocycle, aryl or substituted aryl, amino or substituted amino;

$R_6$ is hydrogen, halogen, cyano, nitro, $CF_3$, $OCF_3$, alkyl or substituted alkyl, heterocycle or substituted heterocycle, aryl or substituted aryl, or $OR_a$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and (b) a pharmaceutically acceptable excipient, carrier, or diluent.

16. The method of claim 15, wherein the compound of Formula I is further selected from the group consisting of:

(1) 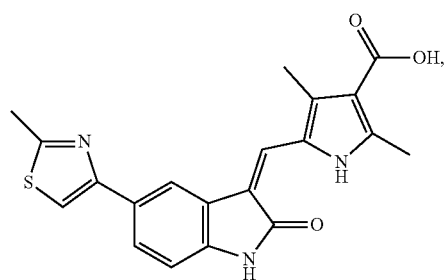
(2) 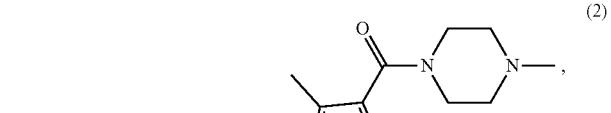
(3) 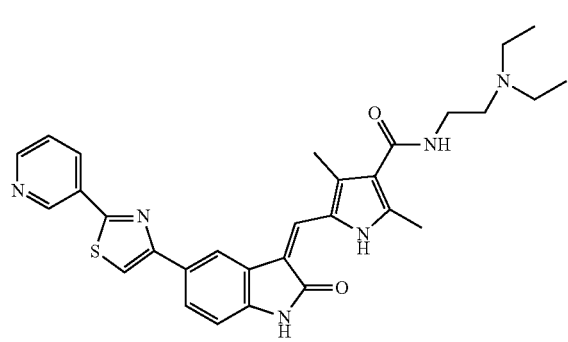
(4) 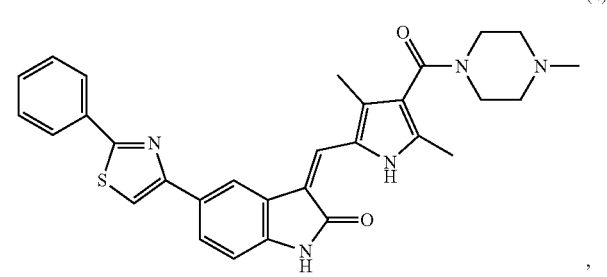
(5) 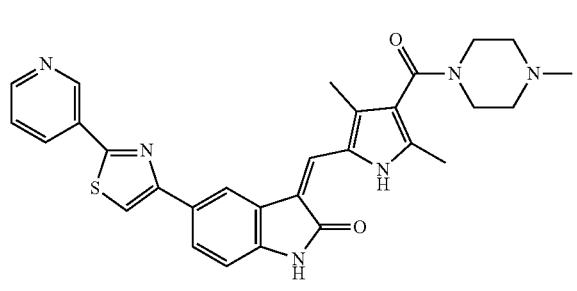
(6) 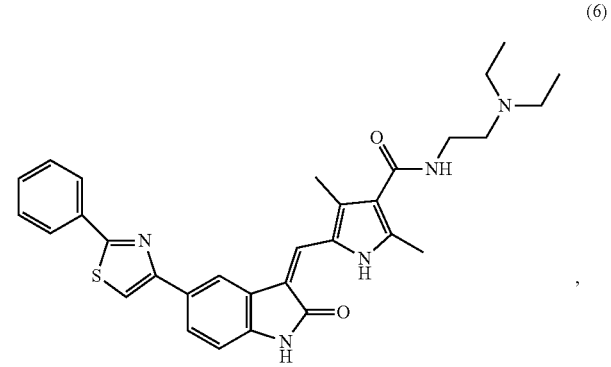
(7) 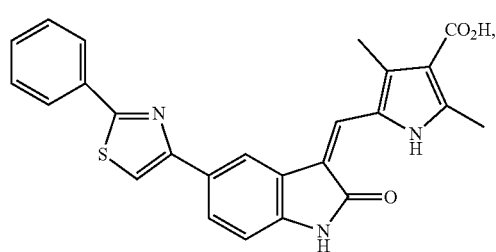
(8) 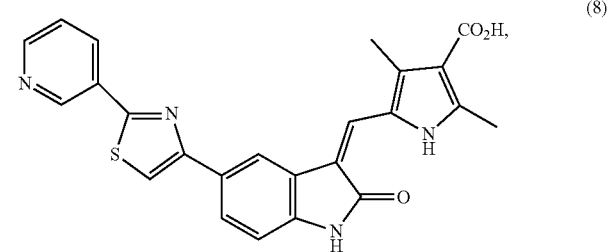
(9) 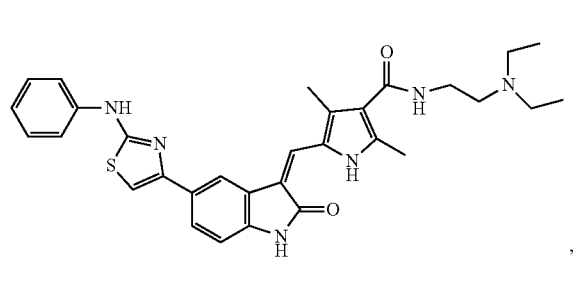
(10) 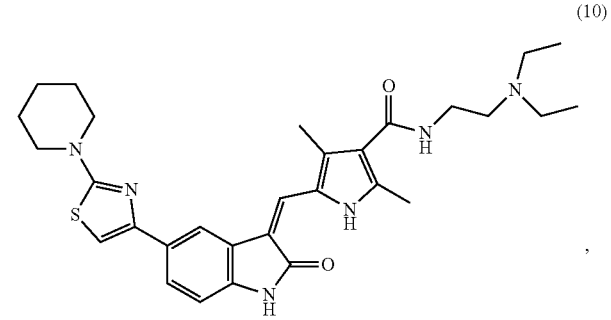

(11)
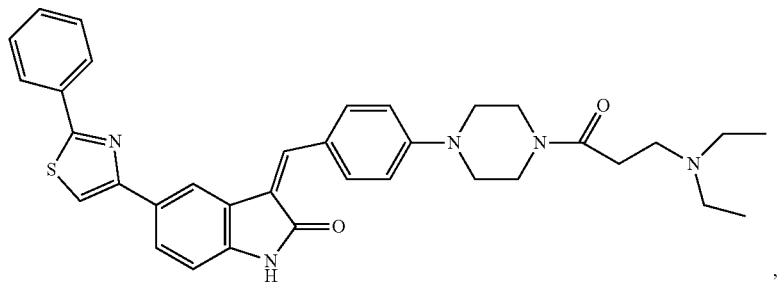
,
(12)
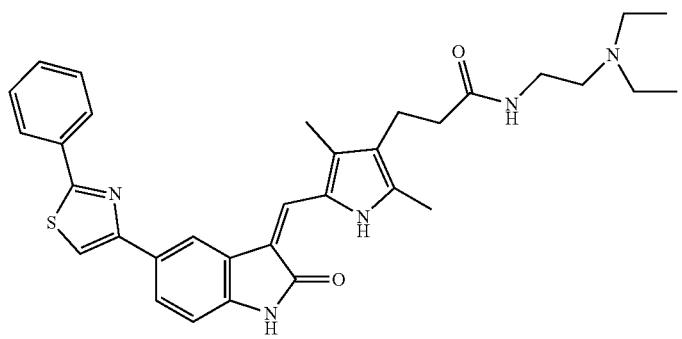
;
and an enantiomer, diastereomer, tautomer, or pharmaceutically acceptable salt, solvate, ester or pro-drug thereof.
17. The method of claim 15, wherein the compound of Formula I comprises at least one deuterium, and is selected from the group consisting of:
(13)
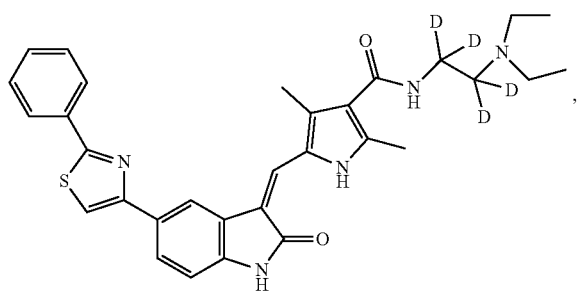
,
(14)
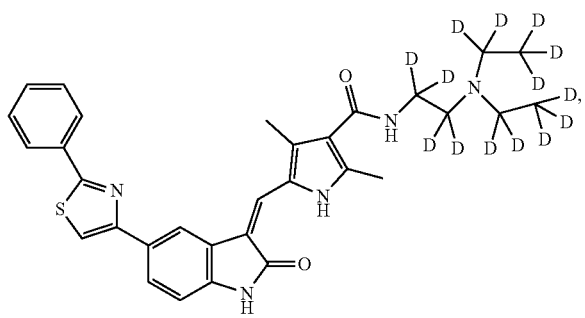
,
(15)
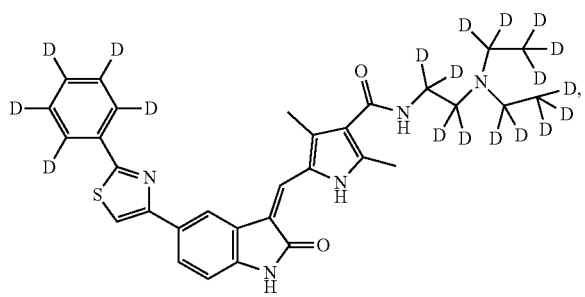
(16)
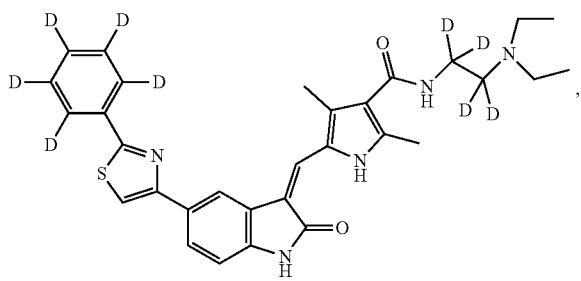
, (17)

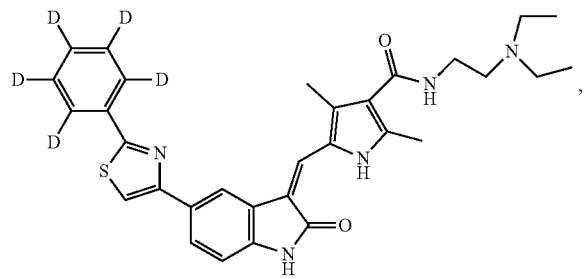

(18)

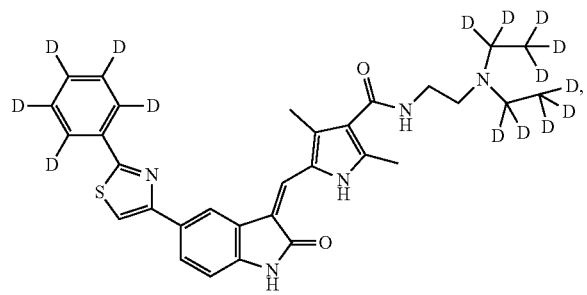

(19)

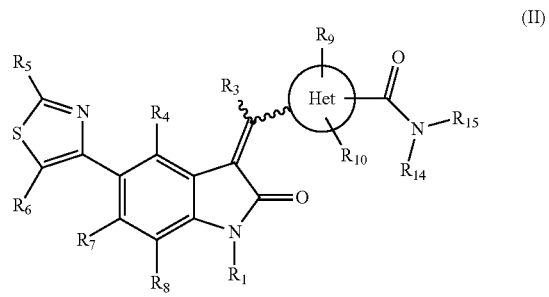

and an enantiomer, diastereomer, tautomer, or pharmaceutically acceptable salt, solvate, ester or pro-drug thereof.

18. The method of claim 15, wherein the compound of Formula I is further a compound of Formula II:

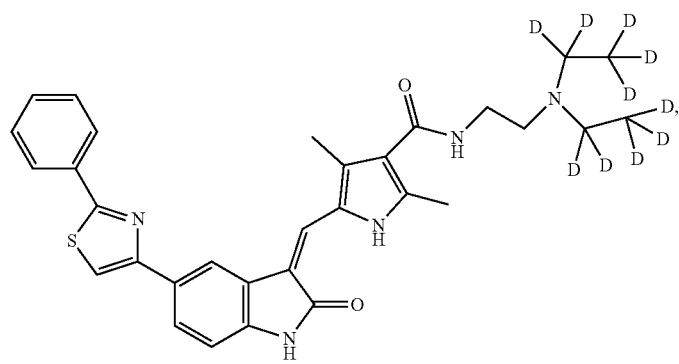

(II)

or an enantiomer, diastereomer, tautomer, or pharmaceutically acceptable salt, solvate, ester or pro-drug thereof, and wherein the symbols have the following meanings and are, for each occurrence, independently selected:

Het is a 5- or 6-membered aromatic ring containing at least one heteroatom selected from N, O and S;

$R_3$ and $R_{10}$ are each independently hydrogen, alkyl or substituted alkyl, cycloalkyl or substituted cycloalkyl, heterocycle or substituted heterocycle, aryl or substituted aryl;

$R_6$ and $R_9$ are each independently hydrogen, halogen, cyano, nitro, $CF_3$, $OCF_3$, alkyl or substituted alkyl, heterocycle or substituted heterocycle, aryl or substituted aryl, or $OR_a$; and $R_{14}$ and $R_{15}$ are independently hydrogen, alkyl or substituted alkyl, cycloalkyl or substituted cycloalkyl, heterocycle or substituted heterocycle, or aryl or substituted aryl, or said $R_{14}$ and $R_{15}$ together with the N to which they are bonded optionally form a heterocycle or substituted heterocycle.

\* \* \* \* \*